US011445996B2

(12) United States Patent
Qi et al.

(10) Patent No.: US 11,445,996 B2
(45) Date of Patent: *Sep. 20, 2022

(54) ENDOVASCULAR NAVIGATION SYSTEM AND METHOD

(71) Applicant: TELEFLEX LIFE SCIENCES LIMITED, Valletta (MT)

(72) Inventors: Wenkang Qi, Cupertino, CA (US); Bradley Hill, Santa Clara, CA (US)

(73) Assignee: TELEFLEX LIFE SCIENCES LIMITED, Valletta (MT)

(*) Notice: Subject to any disclaimer, the term of this patent is extended or adjusted under 35 U.S.C. 154(b) by 411 days.

This patent is subject to a terminal disclaimer.

(21) Appl. No.: 16/531,366

(22) Filed: Aug. 5, 2019

(65) Prior Publication Data
US 2019/0357875 A1 Nov. 28, 2019

Related U.S. Application Data

(60) Continuation of application No. 14/811,923, filed on Jul. 29, 2015, now Pat. No. 10,368,830, which is a
(Continued)

(51) Int. Cl.
*A61B 8/06* (2006.01)
*A61B 8/00* (2006.01)
(Continued)

(52) U.S. Cl.
CPC ............... *A61B 8/06* (2013.01); *A61B 5/026* (2013.01); *A61B 5/065* (2013.01); *A61B 5/283* (2021.01);
(Continued)

(58) Field of Classification Search
CPC ......... A61B 5/026; A61B 5/065; A61B 5/283; A61B 5/349; A61B 5/389; A61B 5/7264;
(Continued)

(56) References Cited

U.S. PATENT DOCUMENTS 3,565,062 A 2/1971 Kuris et al.
4,143,650 A 3/1979 Hatke
(Continued)

FOREIGN PATENT DOCUMENTS

EP 0917069 A1 5/1999
EP 1181895 A2 2/2002
(Continued)

OTHER PUBLICATIONS

Benchimol et al.; Right atrium and superior vena cava flow velocity in man measured with the doppler-catheter flowmeter-telemetry system; The Amer. J of Med.; vol. 48; pp. 303-309; 1970.
(Continued)

*Primary Examiner* — Michael T Rozanski
(74) *Attorney, Agent, or Firm* — BakerHostetler

(57) ABSTRACT

A method of navigating and positioning an endovascular device in a vasculature is disclosed. Initially, a system including an endovascular device and at least one transducer is inserted into the lumen of a patient. An acoustic signal is then transmitted within the lumen. A reflected signal is pre-processed to extract one or more acoustic features. The one or more acoustic features are processed using a computer readable set of rules to produce an output related to guidance of the instrument within a blood vessel or a position of the instrument within the blood vessel.

20 Claims, 22 Drawing Sheets

Related U.S. Application Data division of application No. 13/292,010, filed on Nov. 8, 2011, now Pat. No. 9,119,551.

(60) Provisional application No. 61/411,412, filed on Nov. 8, 2010.

(51) Int. Cl.

| | |
|---|---|
| *A61B 5/0452* | (2006.01) |
| *A61B 5/06* | (2006.01) |
| *A61B 8/08* | (2006.01) |
| *A61B 8/12* | (2006.01) |
| *A61B 5/042* | (2006.01) |
| *A61B 5/0488* | (2006.01) |
| *A61B 5/026* | (2006.01) |
| *A61B 5/283* | (2021.01) |
| *A61B 5/349* | (2021.01) |
| *A61B 5/389* | (2021.01) |
| *A61M 25/01* | (2006.01) |
| *A61B 5/00* | (2006.01) |

(52) U.S. Cl.
CPC .............. *A61B 5/349* (2021.01); *A61B 5/389* (2021.01); *A61B 8/0841* (2013.01); *A61B 8/12* (2013.01); *A61B 8/445* (2013.01); *A61B 8/463* (2013.01); *A61B 8/5223* (2013.01); *A61B 5/7264* (2013.01); *A61B 8/465* (2013.01); *A61M 25/01* (2013.01); *A61M 25/0133* (2013.01); *A61M 2025/0166* (2013.01); *A61M 2205/50* (2013.01); *A61M 2210/12* (2013.01); *A61M 2230/00* (2013.01)

(58) Field of Classification Search
CPC ........... A61B 8/06; A61B 8/0841; A61B 8/12; A61B 8/445; A61B 8/463; A61B 8/465; A61B 8/5223; A61M 2025/0166; A61M 2205/50; A61M 2210/12; A61M 2230/00; A61M 25/01; A61M 25/0133; G16H 50/30

See application file for complete search history.

(56) References Cited

U.S. PATENT DOCUMENTS

| | | |
|---|---|---|
| 4,324,258 A | 4/1982 | Huebscher et al. |
| 4,354,502 A | 10/1982 | Colley et al. |
| 4,503,861 A | 3/1985 | Entrekin |
| 4,549,879 A | 10/1985 | Groshong et al. |
| 4,637,401 A | 1/1987 | Johnston |
| 4,644,960 A | 2/1987 | Johans |
| 4,667,679 A | 5/1987 | Sahota |
| 4,692,148 A | 9/1987 | Kantrowitz et al. |
| 4,706,681 A | 11/1987 | Breyer et al. |
| 4,790,831 A | 12/1988 | Skribiski |
| 4,819,652 A | 4/1989 | Micco |
| 4,849,172 A | 7/1989 | Yafuso et al. |
| 4,856,529 A | 8/1989 | Segal |
| 4,896,677 A | 1/1990 | Kaneko et al. |
| 4,966,148 A | 10/1990 | Millar |
| 4,967,753 A | 11/1990 | Haase et al. |
| 4,979,510 A | 12/1990 | Franz et al. |
| 5,038,789 A | 8/1991 | Frazin |
| 5,046,497 A | 9/1991 | Millar |
| 5,047,930 A | 9/1991 | Martens et al. |
| 5,058,597 A | 10/1991 | Onoda et al. |
| 5,078,148 A | 1/1992 | Nassi et al. |
| 5,078,678 A | 1/1992 | Katims |
| 5,107,841 A | 4/1992 | Sturgill |
| 5,125,410 A | 6/1992 | Kazuhiro et al. |
| 5,174,295 A | 12/1992 | Christian et al. |
| 5,190,045 A | 3/1993 | Frazin |
| 5,207,226 A | 5/1993 | Bailin et al. |
| 5,220,924 A | 6/1993 | Frazin |
| 5,269,289 A | 12/1993 | Takehana et al. |
| 5,271,404 A | 12/1993 | Corl et al. |
| 5,311,871 A | 5/1994 | Yock |
| 5,313,947 A | 5/1994 | Micco |
| 5,431,628 A | 7/1995 | Millar |
| 5,477,858 A | 12/1995 | Norris et al. |
| 5,492,125 A | 2/1996 | Kim et al. |
| 5,546,949 A | 8/1996 | Frazin et al. |
| 5,566,674 A | 10/1996 | Weng |
| 5,575,286 A | 11/1996 | Weng et al. |
| 5,588,432 A | 12/1996 | Crowley |
| 5,640,961 A | 6/1997 | Verdonk |
| 5,657,760 A | 8/1997 | Ying et al. |
| 5,666,958 A | 9/1997 | Rothenberg et al. |
| 5,669,389 A | 9/1997 | Rotteveel et al. |
| 5,693,032 A | 12/1997 | Bierman |
| 5,697,377 A | 12/1997 | Wittkampf |
| 5,722,959 A | 3/1998 | Bierman |
| 5,733,323 A | 3/1998 | Buck et al. |
| 5,749,364 A | 5/1998 | Sliwa, Jr. et al. |
| 5,782,766 A | 7/1998 | Weng et al. |
| 5,785,657 A | 7/1998 | Breyer et al. |
| 5,795,298 A | 8/1998 | Vesely et al. |
| 5,803,083 A | 9/1998 | Buck et al. |
| 5,857,973 A | 1/1999 | Ma et al. |
| 5,860,951 A | 1/1999 | Eggers et al. |
| 5,876,342 A | 3/1999 | Chen et al. |
| 5,878,746 A | 3/1999 | Lemelson et al. |
| 5,891,036 A | 4/1999 | Izumi |
| 5,897,488 A | 4/1999 | Ueda |
| 5,908,385 A | 6/1999 | Chechelski et al. |
| 5,935,143 A | 8/1999 | Hood |
| 5,938,603 A | 8/1999 | Ponzi |
| 5,999,846 A | 12/1999 | Pardey et al. |
| 6,007,491 A | 12/1999 | Ling et al. |
| 6,059,731 A | 5/2000 | Seward et al. |
| 6,083,170 A | 7/2000 | Ben-Haim |
| 6,120,445 A | 9/2000 | Grunwald |
| 6,179,781 B1 | 1/2001 | Phillips |
| 6,179,782 B1 | 1/2001 | Cuce |
| 6,196,972 B1 | 3/2001 | Moehring |
| 6,213,947 B1 | 4/2001 | Phillips |
| 6,246,898 B1 | 6/2001 | Vesely et al. |
| 6,251,073 B1 | 6/2001 | Imran et al. |
| 6,264,611 B1 | 7/2001 | Ishikawa et al. |
| 6,364,838 B1 | 4/2002 | Freiburger et al. |
| 6,500,130 B2 | 12/2002 | Kinsella et al. |
| 6,520,916 B1 | 2/2003 | Brennen |
| 6,524,249 B2 | 2/2003 | Moehring et al. |
| 6,542,626 B1 | 4/2003 | Brouwer et al. |
| 6,547,736 B1 | 4/2003 | Moehring et al. |
| 6,551,244 B1 | 4/2003 | Gee |
| 6,556,695 B1 | 4/2003 | Packer et al. |
| 6,561,979 B1 | 5/2003 | Wood et al. |
| 6,591,144 B2 | 7/2003 | Pigott |
| 6,594,524 B2 | 7/2003 | Esteller et al. |
| 6,612,992 B1 | 9/2003 | Hossack et al. |
| 6,638,243 B2 | 10/2003 | Kupiecki |
| 6,685,648 B2 | 2/2004 | Flaherty et al. |
| 6,689,119 B1 | 2/2004 | Di Caprio et al. |
| 6,695,785 B2 | 2/2004 | Brisken et al. |
| 6,704,590 B2 | 3/2004 | Haldeman |
| 6,719,756 B1 | 4/2004 | Muntermann |
| 6,733,454 B1 | 5/2004 | Bakircioglu et al. |
| 6,740,590 B1 | 5/2004 | Yano et al. |
| 6,749,606 B2 | 6/2004 | Keast et al. |
| 6,814,702 B2 | 11/2004 | Redano |
| 6,842,639 B1 | 1/2005 | Winston et al. |
| 6,866,677 B2 | 3/2005 | Douk et al. |
| 6,896,658 B2 | 5/2005 | Ji et al. |
| 6,931,269 B2 | 8/2005 | Terry |
| 6,934,358 B2 | 8/2005 | Ritt et al. |
| 6,973,352 B1 | 12/2005 | Tsutsui et al. |
| 7,037,290 B2 | 5/2006 | Gardeski et al. |
| 7,043,293 B1 | 5/2006 | Baura |
| 7,081,092 B2 | 7/2006 | Schutt |
| 7,150,716 B2 | 12/2006 | Jones et al. |
| 7,200,435 B2 | 4/2007 | Ricci et al. |

(56) References Cited

U.S. PATENT DOCUMENTS

| | | | |
|---|---|---|---|
| 7,204,798 B2 | 4/2007 | Zdeblick et al. |
| 7,225,013 B2 | 5/2007 | Geva et al. |
| 7,302,285 B2 | 11/2007 | Fuimaona et al. |
| 7,346,393 B2 | 3/2008 | Spinelli et al. |
| 7,367,949 B2 | 5/2008 | Korhonen et al. |
| 7,393,501 B2 | 7/2008 | Zumeris et al. |
| 7,422,563 B2 | 9/2008 | Roschak et al. |
| 7,433,853 B2 | 10/2008 | Brockway et al. |
| 7,485,095 B2 | 2/2009 | Shusterman |
| 7,599,730 B2 | 10/2009 | Hunter et al. |
| 7,627,386 B2 | 12/2009 | Mo et al. |
| 7,640,055 B2 | 12/2009 | Geva et al. |
| 7,668,579 B2 | 2/2010 | Lynn |
| 7,684,850 B2 | 3/2010 | Govari et al. |
| 7,689,268 B2 | 3/2010 | Marshik-Geurts et al. |
| 7,697,972 B2 | 4/2010 | Verard et al. |
| 7,708,696 B2 | 5/2010 | Ritter et al. |
| 7,733,224 B2 | 6/2010 | Tran |
| 7,794,407 B2 | 9/2010 | Rothenberg |
| 7,833,221 B2 | 11/2010 | Voegele et al. |
| 7,857,763 B2 | 12/2010 | Tai |
| 7,966,061 B2 | 6/2011 | Al-Abed et al. |
| 7,967,830 B2 | 6/2011 | Ayala et al. |
| 7,981,038 B2 | 7/2011 | Kanade et al. |
| 7,991,458 B2 | 8/2011 | Hardahl et al. |
| 8,046,052 B2 | 10/2011 | Verard et al. |
| 8,052,648 B2 | 11/2011 | Dikeman et al. |
| 8,060,185 B2 | 11/2011 | Hunter et al. |
| 8,070,684 B2 | 12/2011 | Dala-Krishna |
| 8,126,241 B2 | 2/2012 | Zarkh et al. |
| 8,180,440 B2 | 5/2012 | McCombie et al. |
| 8,238,639 B2 | 8/2012 | Silver |
| 8,409,103 B2 | 4/2013 | Grunwald et al. |
| 8,594,776 B2 | 11/2013 | McCombie et al. |
| 8,636,659 B2 | 1/2014 | Alpert et al. |
| 8,688,210 B2 | 4/2014 | Burnes et al. |
| 8,718,346 B2 | 5/2014 | Isaacs et al. |
| 8,798,357 B2 | 8/2014 | Sinha et al. |
| 8,830,224 B2 | 9/2014 | Zhao et al. |
| 9,119,551 B2 * | 9/2015 | Qi | A61B 8/06 |
| 10,368,830 B2 * | 8/2019 | Qi | A61B 5/026 |
| 2002/0045810 A1 | 4/2002 | Ben-Haim |
| 2002/0055680 A1 | 5/2002 | Miele et al. |
| 2002/0087156 A1 | 7/2002 | Maguire et al. |
| 2002/0091319 A1 | 7/2002 | Moehring et al. |
| 2002/0111548 A1 | 8/2002 | Swanson et al. |
| 2002/0151790 A1 | 10/2002 | Abend |
| 2002/0156363 A1 | 10/2002 | Hunter et al. |
| 2002/0168618 A1 | 11/2002 | Anderson et al. |
| 2002/0188257 A1 | 12/2002 | Bierman |
| 2003/0083717 A1 | 5/2003 | Mlynski et al. |
| 2003/0109785 A1 | 6/2003 | Buck et al. |
| 2004/0011358 A1 | 1/2004 | Smaldone et al. |
| 2004/0024298 A1 | 2/2004 | Marshik-Geurts et al. |
| 2004/0039436 A1 | 2/2004 | Spenser et al. |
| 2004/0102719 A1 | 5/2004 | Keith et al. |
| 2004/0116809 A1 | 6/2004 | Chow et al. |
| 2004/0116969 A1 | 6/2004 | Owen et al. |
| 2004/0120557 A1 | 6/2004 | Sabol et al. |
| 2004/0158143 A1 | 8/2004 | Flaherty et al. |
| 2004/0254523 A1 | 12/2004 | Fitzgerald et al. |
| 2005/0085718 A1 | 4/2005 | Shahidi |
| 2005/0148836 A1 | 7/2005 | Kleen et al. |
| 2005/0159738 A1 | 7/2005 | Visram et al. |
| 2006/0079868 A1 | 4/2006 | Makin et al. |
| 2006/0084883 A1 | 4/2006 | Linker |
| 2006/0094923 A1 | 5/2006 | Mate |
| 2006/0100530 A1 | 5/2006 | Kliot et al. |
| 2006/0173311 A1 | 8/2006 | Hao et al. |
| 2006/0229594 A1 | 10/2006 | Francischelli et al. |
| 2006/0241459 A1 | 10/2006 | Tai |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0167738 A1 | 7/2007 | Timinger et al. |
| 2007/0167794 A1 | 7/2007 | Dala-Krishna |
| 2007/0265526 A1 | 11/2007 | Govari et al. |
| 2007/0276334 A1 | 11/2007 | Bierman et al. |
| 2008/0015440 A1 | 1/2008 | Shandas et al. |
| 2008/0058607 A1 | 3/2008 | Watrous |
| 2008/0061961 A1 | 3/2008 | John |
| 2008/0071314 A1 | 3/2008 | John |
| 2008/0161669 A1 | 7/2008 | Hauck et al. |
| 2008/0188740 A1 | 8/2008 | Diaz et al. |
| 2008/0221438 A1 | 9/2008 | Chen et al. |
| 2009/0005675 A1 | 1/2009 | Grunwald et al. |
| 2009/0118612 A1 | 5/2009 | Grunwald et al. |
| 2009/0143740 A1 | 6/2009 | Bierman et al. |
| 2009/0156926 A1 | 6/2009 | Messerly et al. |
| 2009/0177089 A1 | 7/2009 | Govari et al. |
| 2009/0177090 A1 | 7/2009 | Grunwald et al. |
| 2009/0182283 A1 | 7/2009 | Sloan |
| 2009/0234328 A1 | 9/2009 | Cox et al. |
| 2009/0259124 A1 | 10/2009 | Rothenberg |
| 2009/0262977 A1 | 10/2009 | Huang et al. |
| 2009/0270712 A1 | 10/2009 | Raghavan et al. |
| 2009/0287070 A1 | 11/2009 | Baker, Jr. |
| 2009/0287191 A1 | 11/2009 | Ferren et al. |
| 2010/0022886 A1 | 1/2010 | Ayati et al. |
| 2010/0036227 A1 | 2/2010 | Cox et al. |
| 2010/0198346 A1 | 8/2010 | Keogh et al. |
| 2010/0204569 A1 | 8/2010 | Burnside et al. |
| 2010/0210947 A1 | 8/2010 | Burcher et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2011/0087114 A1 | 4/2011 | Moulder |
| 2011/0125023 A1 | 5/2011 | Palti et al. |
| 2011/0196248 A1 | 8/2011 | Grunwald |
| 2011/0257600 A1 | 10/2011 | Kessler |
| 2011/0282187 A1 | 11/2011 | Harlev et al. |
| 2011/0317006 A1 | 12/2011 | Kuboyama et al. |
| 2012/0035434 A1 | 2/2012 | Ferren et al. |
| 2012/0083702 A1 | 4/2012 | Ingold, Jr. et al. |
| 2012/0101381 A1 | 4/2012 | Palti |
| 2012/0190949 A1 | 7/2012 | McCombie et al. |
| 2012/0197128 A1 | 8/2012 | Palti |
| 2013/0296693 A1 | 11/2013 | Wenzel et al. |

FOREIGN PATENT DOCUMENTS

| | | |
|---|---|---|
| JP | 62500703 A | 3/1987 |
| JP | 62236532 A | 10/1987 |
| JP | 4017843 A | 1/1992 |
| JP | 08229044 A | 9/1996 |
| JP | H09168519 A | 6/1997 |
| JP | 09253084 A | 9/1997 |
| JP | 10277039 A | 10/1998 |
| JP | H11511666 A | 10/1999 |
| JP | 3205040 B2 | 9/2001 |
| JP | 2004500210 A | 1/2004 |
| JP | 2004033673 A | 2/2004 |
| JP | 2004130114 A | 4/2004 |
| JP | 2006504483 A | 2/2006 |
| JP | 2006513731 A | 4/2006 |
| JP | 2006181363 A | 7/2006 |
| JP | 2007500539 A | 1/2007 |
| JP | 2008043735 A | 2/2008 |
| JP | 2008534071 A | 8/2008 |
| JP | 2008541799 A | 11/2008 |
| JP | 2009160397 A | 7/2009 |
| JP | 2010503421 A | 2/2010 |
| JP | 2010520780 A | 6/2010 |
| JP | 2010532227 A | 10/2010 |
| WO | WO9625095 A1 | 8/1996 |
| WO | WO1998008440 | 3/1998 |
| WO | WO2001070303 | 9/2001 |
| WO | WO2004041083 A1 | 5/2004 |
| WO | WO2006051523 A2 | 5/2006 |

(56) References Cited

FOREIGN PATENT DOCUMENTS

| WO | WO2006102511 A2 | 9/2006 |
|---|---|---|
| WO | WO2007047360 A2 | 4/2007 |
| WO | WO2009003138 A1 | 12/2008 |

OTHER PUBLICATIONS

Benchimol et al.; Bidirectional blood flow velocity in the cardiac chambers and great vessels studied with the doppler ultrasonic flowmeter; The Amer. J of Med.; vol. 52; pp. 467-473; 1972.

Bidoggia et al.; Transseptal left heart catheterization: usefulness of the intracavitary electrocardiogram in the localization of the fossa ovalis; Catheterization and Cardiovascular Diagnosis; New York, NY; vol. 24; No. 3; pp. 221-225; Nov. 1, 1991.

Bossert et al.; Swan-Ganz catheter-induced severe complications in cardiac surgery: right ventricular perforation, knotting, and rupture of a pulmonary artery; J. Car. Surg.; vol. 21; No. 3; pp. 292-295; May/Jun. 2006.

Brunner, Eberhard; Ultrasound system considerations and their impact on front-end components; Anolog Devices, Inc.; pp. 1-19; May-Jun. 2002.

Fearon et al.; Evaluating intermediate coronary lesions in the cardiac catheterization laboratory; Rev Cardiovasc Med; vol. 4; No. 1; pp. 1-7; 2003.

Hellerstein et al.; Recording of intracavity potentials through a single lumen, saline filled cardiac catheter; P.S.E.B.M.,; vol. 71; pp. 58-60; 1949.

Kalmanson et al.; Letter to the Editor; "Directional vs bidirectional doppler velocimeter"; Am. Heart J.; vol. 83; No. 3; pp. 437; Mar. 1972.

Lewis et al.; A Study of Normal and abnormal femoral venous flow velocity using a directional doppler; Br. J. Surg: vol. 59, No. 4; pp. 303; Apr. 1972.

McGee, et al.; Accurate placement of central venous catheters: A prospecitve, randomized, multicenter trial; Critical Care Medicine, vol. 21, No. 8, pp. 1118-1123, Aug. 1993.

Naylor; Reduction of malposition in peripherally inserted central catheters with tip location system; JAVA; vol. 12; No. 1; pp. 29-31; 2007.

Pittiruti et al.; The EKG method for positioning the tip of PICCs; results from two preliminary studies;JAVA; vol. 13; No. 4; pp. 112-119; 2008.

Radke et al.; Control of the placement of a central venous catheter using doppler ultrasound; Der Anaesthesist 1990-05; vol. 39; No. 5; pp. 283-287; May 1990.

Starr, et al.; EKG guided placement of subclavian CVP catheters using J-wire; Ann. Surg.; vol. 204, No. 6, pp. 673-676, Dec. 1986.

Stas et al.; Peroperative intravasal electrographic control of catheter tip position in access ports placed by venous cut-down technique;EJSO; vol. 27; pp. 316-320; 2001.

Schummer et al.; Central venous catheters-the inability of 'intra-atrial ECG' to prove adequate positioning; British Jour. of Anaesthesia, vol. 93, No. 2; pp. 193-198, 2004.

Bowers et al.; Respiratory rate derived from principal component analysis of single lead electrocardiogram; Conference Proc.; Computers in Cardiology; Bologna, IT; 2008; vol. 35; pp. 437-440; Sep. 14-17, 2008.

Grunwald et al.; U.S. Appl. No. 13/844,408 entitled "Apparatus and method for endovascular device guiding and positioning using physiological parameters," filed Mar. 15, 2013.

Wenzel et al.; U.S. Appl. No. 13/829,522 entitled "Right atrium indicator," filed Mar. 14, 2013.

Lee et al.; U.S. Appl. No. 13/829,650 entitled "Systems and methods for detection of the superior vena cava area and the cavoatrial junction," filed Mar. 14, 2013.

* cited by examiner

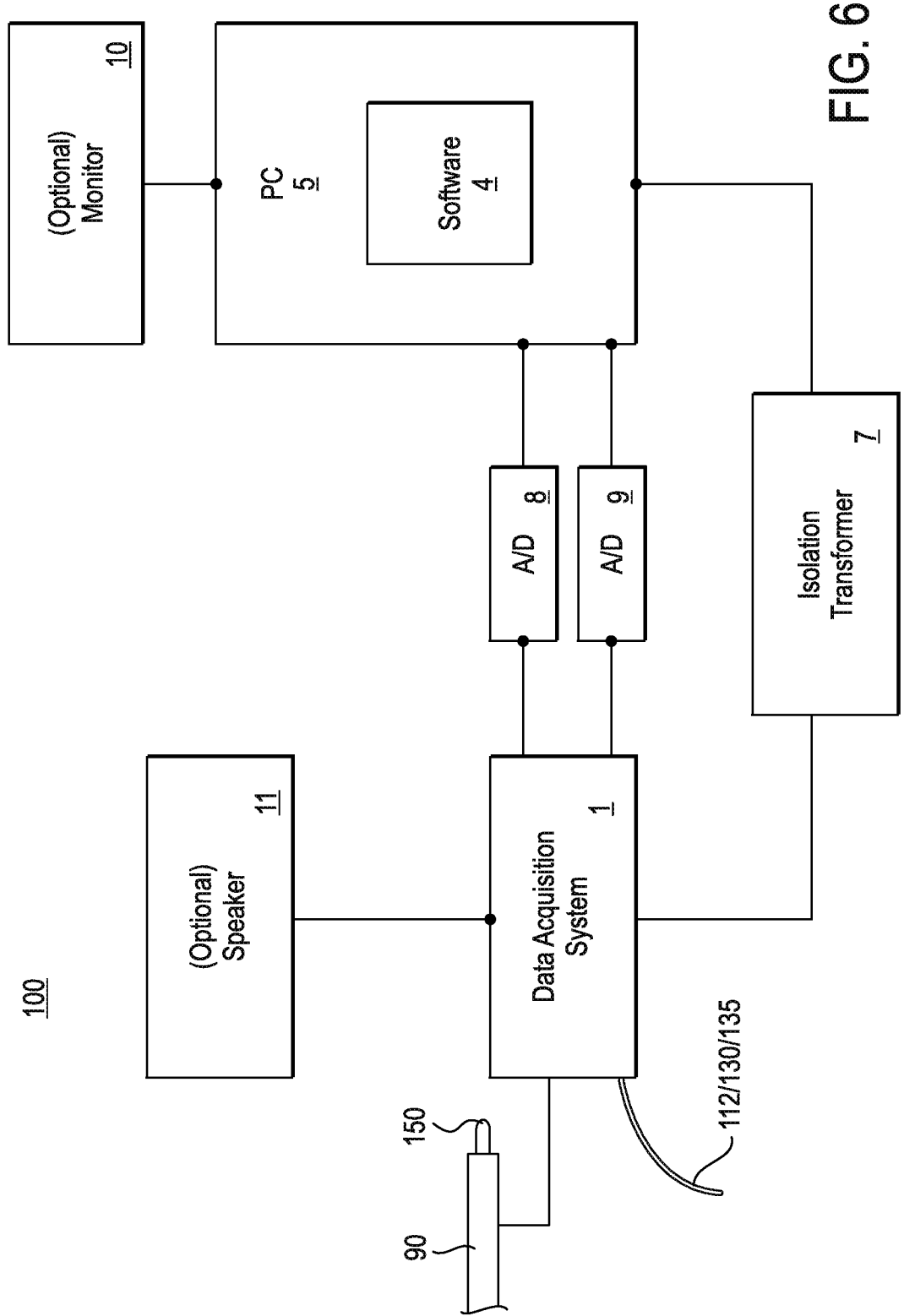

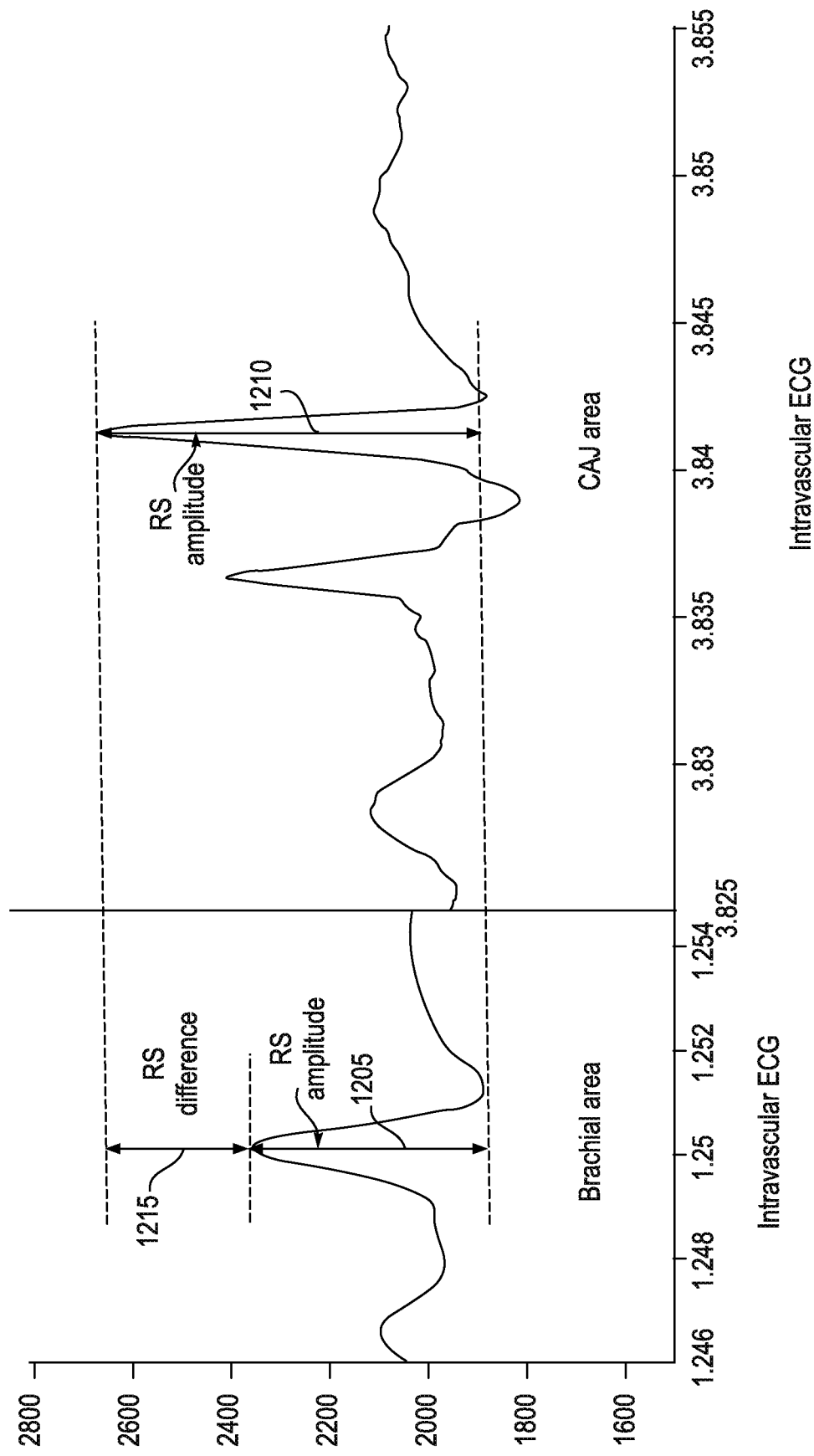

| State | ECG signal | System output displayed on console | Description | Clinical operator's action | Doppler signal |
|---|---|---|---|---|---|
| State 0 | Weak or low usefulness | (Yellow) | The Doppler signal is too weak, or any other unkown scenario | Wait for about 5~10 sec, or push in/push out the catheter, and see if the sign changes | Doppler power is relatively weak |
| State 1 | ECG p wave is not elecated | (Green) | The optimal location is ahead | Advance the catheter | Antegrade flow is dominant over retrograde flow |
| State 2 | ECG p wave is elevated | (Blue Bull's Eye) | The catheter tip location is at the optimal location | Stop and keep the tip location in the area, ready to wrap up the procedure | Dominant low frequency in both antegrade and retrograde flow |
| State 3 | ECG signal is not elevated or ECG p wave is elevated, and ECG p wave shows biphasic | (Red) | Either the trip location is too deep in atrium, or in wrong places, such as subclavian, azygos, IJ, or the stylet is coiled | Pull back the catheter untill red sign changes to other signs | Retrograde flow is dominant over antegrade flow |

FIG. 23

ENDOVASCULAR NAVIGATION SYSTEM AND METHOD

CROSS REFERENCE TO RELATED APPLICATIONS

This application is a continuation of U.S. patent application Ser. No. 14/811,923, filed Jul. 29, 2015 and issued as U.S. Pat. No. 10,368,830, which is a divisional of U.S. patent application Ser. No. 13/292,010 and issued as U.S. Pat. No. 9,119,551, filed Nov. 8, 2011, which claims the benefit of U.S. Provisional Patent Application No. 61/411,412, filed Nov. 8, 2010, the entirety of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates, in general, to an endovascular navigation system and methods for guiding and positioning an endovascular device using an algorithm-based pattern recognition processor.

BACKGROUND OF THE INVENTION

This invention provides a method to substantially increase the accuracy and reduce the need for imaging related to placing an intravascular catheter or other device. Aspects of the invention relate to the guidance, positioning and placement confirmation of intravascular devices, such as catheters, stylets, guidewires and other elongate bodies that are typically inserted percutaneously into the venous or arterial vasculature, including flexible elongate bodies. Currently, these goals are suboptimally achieved using x-ray imaging, fluoroscopy, and in some cases ultrasound imaging. ECG alone is used but has severe limitations with accuracy, navigation along the entire venous pathway, and is of minimal value in the presence of arrhythmia or abnormal heart cardiac activity. Reduced imaging reduces the amount of radiation that patients are subjected to, reduces the time required for the procedure, and decreases the cost of the procedure by reducing the time needed in the radiology department. The degree of accuracy provided by the invention is critical because there are patient consequences to a catheter in a location that is not precisely correct.

The vasculature of mammals has long been accessed to provide therapy, administer pharmacological agents, and meet other clinical needs. Numerous procedures exist in both venous and arterial systems and are selected based on patient need. One challenge common to all vascular-based therapies is health care provider access to the specific location or section of the vascular tree.

One common venous access procedure is central venous access. Central venous access is the placement of a venous catheter in a vein that leads directly to the heart. Central venous catheters are ubiquitous in modern hospital and ambulatory medicine, with up to 8 million insertions per year in the U.S. and a similar number outside the U.S.

Venous access devices are most often used for the following purposes:

Administration of medications, such as antibiotics, chemotherapy drugs, and other IV drugs
Administration of fluids and nutritional compounds (hyperalimentation)
Transfusion of blood products
Hemodialysis
Multiple blood draws for diagnostic testing Consequences of cather tip placement inaccuracies include, among other things:
Increased risk of thrombis formation
Venous damage due to drug toxicity
Increased risk of infection
Additional radiation exposure Central venous access devices are typically small, flexible tubes placed in large veins for people who require frequent access to their bloodstream. The devices typically remain in place for long periods: week, months, or even longer.

Central venous access devices are usually inserted in one of three ways:
a) Directly. Catheters are inserted by tunneling under the skin into either the subclavian vein (located beneath the collarbone) or into the internal jugular vein (located in the neck). The part of the catheter where medications are administered or blood is drawn remains outside of the skin.
b) Through a port. Unlike catheters, which exit from the skin, ports are placed completely below the skin. With a port, a raised disk about the size of a quarter or half dollar is felt underneath the skin. Blood is drawn or medication delivered by placing a tiny needle through the overlying skin into the port or reservoir.
c) Indirectly via a periphal vein. Peripherally inserted central catheter (PICC) lines, unlike central catheters and ports, are not inserted directly into the central vein. A PICC line is inserted into a large vein in the arm and advanced forward into the larger subclavian vein.

Central catheters and ports are usually inserted by a surgeon or surgical assistant in a surgical suite. A PICC line can be put in at bedside, usually by a specially-trained nurse. In this latter case, confirmation by X-ray is currently required for assessing the success of the PICC placement. Therefore PICC procedures as currently practiced involve exposure to X-ray, and manipulation of the catheter increases the risks of infection.

Traditional, surgically-placed central catheters are increasingly being replaced by peripherally inserted central venous access devices. PICC lines usually cause fewer severe complications than central venous access devices. The PICC line placement procedure is performed by interventional radiologists to deliver long-term drug delivery, chemotherapy procedures, delivery of intravenous medications or intravenous nutrition (hyperalimentation) and taking blood samples. Insertion of PICC lines is a routine procedure in that it is carried out for a variety of treatments, and more than once in the same patient when the catheter is to be left in place for any length of time. Even though it is routine, it is a very time and labor-intensive procedure for the hospital staff, which also makes it expensive. During the procedure the physician or nurse places the catheter into a superficial arm vein such as the cephalic, basilic, antecubital, median cubital, or other superficial vein with the goal of having the distal end of the catheter reach the superior vena cava. After entering the superficial vein around the area where the arm bends (elbow), the catheter is advanced up the subclavian vein, then the brachiocephalic vein and finally it enters the superior vena cava. One caveat is to make sure that the PICC line does not enter and remain in the jugular vein.

In addition to guiding the catheter through the vasculature, the final location of the catheter tip is very important to the success of the procedure. Catheters will generally function equally well for pressure measurement and fluid infusion if the tip is situated in any major vein, above the heart, or below the heart. For dialysis or the infusion of irritant/hypertonic fluids, a high rate of blood flow past the catheter tip is desirable and this requires the placement of the luminal opening in as large a vessel as possible. However, central venous catheter instructions for use give strong warnings about the requirement for catheter tips to lie outside the heart to avoid perforation and subsequent pericardial tamponade. Likewise positioning the catheter tip away from small peripheral veins is important to avoid damaging the vein wall or occluding the vein due the caustic effects of the infusing solution. An interventional radiologist may use a fluoroscopic agent to delineate the veins in the body and subsequently verify the correct positioning of the catheter tip using a post-operative X-ray. Currently, a post-operative X-ray is performed routinely while some studies have shown that only 1.5% of the cases are subject to complications that would indeed require X-ray imaging.

Current methods for guiding PICC lines include the legacy landmark measurement technique, X-ray guidance, external electromagnetic sensors, and intravascular sensors (e.g. ECG sensor). In the case of external electromagnetic sensors, the endovascular device is guided by assessing the distance between an electromagnetic element at the tip of the device (e.g. a coil) and an external (out of body) receiver. This method is inaccurate because it does not actually indicate location in the vascular but instead indicates only relative position to an external reference. In the case of ECG-guided catheters, the classic increase in P-wave size, known as 'P-atriale", is a widely accepted criterion for determining location of central venous catheter tips in the proximity of the sino-atrial node. Current methods include using a catheter filled with saline and an ECG adaptor at the proximal end connected to an ECG system. This method is inaccurate because it does not indicate location in the blood vessel but instead indicates the proximity of the sino-atrial node (SA node).

Because of known inaccuracies, all the current methods in use explicitly require the use of a confirmatory chest X-ray to verify and confirm location of the tip of the endovascular device at the desired target in the vasculature.

Additional approaches based on the use of non-imaging ultrasound are described in U.S. Patent Pub. Nos. 2007/0016068, 2007/0016069, 2007/0016070, and 2007/0016072, incorporated herein for all purposes. Limitations of an approach based exclusively on measuring right-atrial electrocardiograms have been described in the literature, for example, in [1]: W. Schummer et al., Central venous catheters—the inability of 'intra-atrial ECCG' to prove adequate positioning, *British Journal of Anaesthesia*, 93 (2): 193-8, 2004.

What is needed is a guidance system and method that overcome the above and other disadvantages of known systems and methods.

In view of the variable nature of physiological signal information used during endovascular positioning and guidance, what is needed are methods and apparatuses to optimize the use of physiological signal information and take into account the variable accuracy and usefulness of the signal information.

What is needed is a guidance system and method that can accurately position a device in irregular vascular environments such as the vasculature of patients with an aneurysm or arrhythmia.

What is needed is increased accuracy of the catheter tip placement without additional X-rays and manipulation of the catheter.

SUMMARY OF THE INVENTION

An aspect of the invention includes an endovenous access and guidance system enabled with artificial intelligence capabilities. The system includes a transducer on a distal end of an endovascular instrument, a control system connected to the transducer, the control system being configured to generate and receive at least one acoustic signal using the transducer, a pre-processor containing computer-readable instructions for manipulating the acoustic signal input to extract information related to one or more desired parameters, a processor configured to evaluate the acoustic features to generate an output related to guidance of the instrument, and an output device for displaying an indication of the output generated by the processor. The processor may evaluate the information using artificial intelligence and inference rules, comparisons to information in a database, probabilities, among others. The system may use an electrical signal from, for example, the heart as a confirmation input. Further disclosed is a method of navigating and positioning an endovascular device in a vasculature, and more specifically, in a blood vessel. In various embodiments, the acoustic signal comprises a non-imaging ultrasound signal.

In various embodiments, the positioning system further includes a sensing electrode mounted on the instrument, the sensing electrode being connected to the control system and configured to measure and/or detect electrical signals from the heart. The control system may be configured to receive an electrical signal from the sensing electrode. The pre-processor may contain instructions for manipulating the received electrical signal to extract information related to one or more desired electrical features. The computer-readable set of inference rules may contain an inference rule to evaluate the one or more electrical features. In various embodiments, the processor evaluates the one or more electrical features to confirm the output related to the guidance or a position of the instrument within a blood vessel.

In various embodiments, the computer-readable set of rules comprises a rule to evaluate whether a power level of the acoustic signal is below a threshold. In various embodiments, the computer-readable set of rules comprising a rule to evaluate whether an antegrade flow in the blood vessel is dominant over a retrograde flow in the blood vessel. Antegrade flow in the blood vessel is flow in the normal direction of flow, which is generally away from the heart in the arterial system and towards the heart in the venous system. Retrograde flow in the blood vessel is flow in the opposite direction of normal flow, i.e. towards the heart in the arterial system or away from the heart in the venous system. In various embodiments, the computer-readable set of rules comprises a rule to evaluate whether a retrograde flow in the blood vessel is dominant over an antegrade flow in the blood vessel. In various embodiments, the computer-readable set of rules comprises a rule to evaluate whether a low frequency signal dominates both an antegrade flow in the blood vessel and a retrograde flow in the blood vessel.

In various embodiments, the control system is configured to synchronize the acoustic signal and the electrical signal.

In various embodiments, the computer-readable set of rules comprises a rule to evaluate a P-wave relative to a reference.

In various embodiments, the output is related to the guidance or position comprises an indication of the most probable condition selected from the group consisting of: instrument moving in a desired direction, instrument moving in an undesired direction, and instrument positioned in a desired location.

In yet another embodiment, the system is configured such that the processor incorporates a predetermined set of processing rules or inference statements to process in vivo non-image based ultrasound information and intravascular electrocardiogram signals of the vasculature system of the patient provided by the sensors to indicate in the output information the location or proximity of the sensors to a structure within the vasculature of the patient.

In various embodiments, the processor contains a member selected from rules, functions, relationships, and combinations of the same used to determine the probable location and/or movement of the device within the body.

In various embodiments, the system includes a pre-processor configured to pre-process physiological signals to provide feature information as inputs to the processor. Exemplary features useful in the positioning schemes described herein include: in vivo non-image based ultrasound information at a particular frequency, energy level, or timing within a portion of a cardiovascular cycle; a portion of an intravascular electrocardiogram signal, a blood flow direction, a blood flow velocity, e.g., the highest, the lowest, the mean or the average velocity, a blood flow signature pattern, a blood flow characteristic at a particular frequency, a pressure signature pattern, A-mode information, a preferential non-random direction of flow, the shape of the different waveforms and complexes charactering the intravascular electrocardiogram, e.g., P-wave, QRS complex, T-wave, the peak-to-peak amplitudes, the absolute and relative amplitude changes and other distinctive elements of the intravascular ECG. Such parameters can be pre-processed as a feature for use in the fuzzy controller either individually or in combination. In one specific example, the signals are pre-processed to provide inputs to the processor based on P-wave changes indicative of the proximity of the sinoatrial node near the caval-atrial junction and together with the venous blood flow signature pattern indicative of the caval-atrial junction. In another specific example, the signals may be pre-processed to identify behavior of a feature in time indicative of location in the vasculature, e.g. evident pulsatile variations of the blood flow signature pattern may be indicative of a location in the internal jugular vein.

Another aspect of the invention includes a method for positioning an instrument in the vasculature of a body. The method includes inserting a system including an endovascular device and at least one transducer into the lumen of a patient, transmitting an acoustic signal, pre-processing the reflected signal to extract information related to one or more desired features, and processing the information as an input to produce an output related to guidance of the instrument within a blood vessel or a position of the instrument within the blood vessel. The system may include any of the features and configurations described above. In various embodiments, the method includes displaying an output comprising an indication of the most probable condition selected from the group consisting of: instrument moving in a desired direction, instrument moving in an undesired direction, and instrument positioned in a desired location. In various embodiments, the method includes advancing the instrument in a blood vessel based on the output.

Another aspect of the invention includes a positioning system. The positioning system includes a transducer for mounting on a distal end of an endovascular instrument; a control system connected to the transducer, the control system being configured to generate and receive an acoustic signal using the transducer; a pre-processor receiving the acoustic signal as an input, the pre-processor containing computer-readable instructions for manipulating the signal input to extract one or more acoustic features from the signal input; a processor configured to receive the one or more extracted features, the processor containing a computer-readable set of rules to evaluate the extracted features using the rules to generate an output related to guidance of the instrument within a blood vessel or a position of the instrument within the blood vessel; and an output device for displaying an indication of the output generated by the processor.

In some embodiments, the positioning system further includes a sensing electrode for mounting on the instrument, the sensing electrode being connected to the control system; wherein the control system is further configured to receive an electrical signal from the sensing electrode, and wherein the pre-processor further contains instructions for manipulating the received electrical signal to extract one or more features related to the electrical signal; and/or wherein the computer-readable set of rules contains a rule to evaluate the one or more electrical features.

In some embodiments, the acoustic signal includes a non-imaging ultrasound signal. In some embodiments, the processor evaluates the one or more electrical features to confirm the output related to the guidance or a position of the instrument within a blood vessel.

In some embodiments, the electrical signal comprises an ECG signal, an EMG signal, and/or an EEG signal.

In some embodiments, the computer-readable set of rules contained in the processor includes artificial intelligence programming; evaluates the extracted features based on at least one of inference rules, an expert system, a neural network, and logic; includes a rule to evaluate whether a power level of the acoustic signal is below a threshold; includes a rule to evaluate whether an antegrade flow in the blood vessel is dominant over a retrograde flow in the blood vessel; includes a rule to evaluate whether a retrograde flow in the blood vessel is dominant over an antegrade flow in the blood vessel; and/or includes a rule to evaluate whether a low frequency signal dominates both an antegrade flow in the blood vessel and a retrograde flow in the blood vessel.

In some embodiments, the control system is configured to synchronize the acoustic signal and the electrical signal.

In some embodiments, the computer-readable set of rules further includes a rule to evaluate a P-wave in the received electrical signal relative to a reference. In some embodiments, the rule to evaluate a P-wave in the received electrical signal relative to a reference further includes providing an output when the P-wave in the received electrical signal is elevated above the reference; providing an output when the P-wave in the received electrical signal is at or below the reference; and/or providing an output when the P-wave in the received electrical signal is biphasic.

In some embodiments, the output related to the guidance or a position includes one of a plurality of states, each state related to a predetermined set of conditions of instrument movement or position; and an indication of the most probable condition selected from the group consisting of: instrument moving in a desired direction, instrument moving in an undesired direction, and/or instrument positioned in a desired location. In some embodiments, the indication of the instrument moving in a desired direction is different from the indication of the instrument positioned in a desired location.

In some embodiments, the one or more features related to the electrical signal corresponds to a pre-selected portion of a regular electrical wave produced by the body; a pre-selected portion of an irregular electrical wave produced by the body; and/or a pre-selected portion of an electrical wave produced by a body having arrhythmia. In some embodiments, the electrical wave is an electrocardiogram and the pre-selected portion is an RS amplitude; an electrocardiogram and the pre-selected portion is an electrocardiogram segment; and/or an electrocardiogram and the pre-selected portion is an electrocardiogram interval.

In some embodiments, the one or more acoustic features corresponds to a ratio of a retrograde power of the flow in the blood vessel to an antegrade power of the flow in the blood vessel during a single ECG cycle; a ratio of a low frequency flow power to a high frequency flow power; an acoustic signal obtained during a portion of a heart beat; the portion of a heart beat during the occurrence of retrograde flow produced by atrial contraction; the portion of a heart beat during the occurrence of antegrade flow during systole; the portion of a heart beat during the occurrence of retrograde flow at the end of systole; and/or the portion of a heart beat during the occurrence of antegrade flow during diastole.

In some embodiments, the one or more features related to the electrical signal corresponds to a portion of an QRS complex; a ratio of a magnitude of a P-wave measured by the sensing electrode and a magnitude of a P-wave measured by an external electrode; and/or an indication of the presence of a biphasic P-wave.

Another aspect of the invention includes a method of positioning an endovascular instrument in a vasculature. The method includes inserting the system of any one of the embodiments discloses herein into the lumen of a patient and advancing the device based on the output.

Another aspect of the invention includes a method of positioning an endovascular instrument in a vasculature. The method includes inserting a system including an endovascular device and at least one transducer into the lumen of a patient; transmitting an acoustic signal within the lumen; pre-processing a reflected signal to extract one or more acoustic features; and processing the one or more acoustic features using a computer readable set of rules to produce an output related to guidance of the instrument within a blood vessel or a position of the instrument within the blood vessel.

In some embodiments, the processing is performed based on a predefined set of inference rules related to one of a set of navigation states; based on a predefined set of probabilities related to one of a set of navigation states; and/or based on a comparison of the one or more parameters to a predefined set of parameters in a database.

In some embodiments, the method further includes displaying the output related to guidance of the device within the blood vessel or a position of the instrument within the blood vessel.

In some embodiments, the output comprises an indication of the most probable condition selected from the group consisting of: instrument moving in a desired direction, instrument moving in an undesired direction, and instrument positioned in a desired location. In some embodiments, the desired direction is towards the heart and/or with a flow of blood returning to the heart, and the undesired direction is away from the heart and/or is against a flow of blood returning to the heart. In some embodiments, the desired location is within a lower third of the superior vena cava; proximate to the caval atrial junction; and/or within the superior vena cava proximate to the caval atrial junction.

In some embodiments, the method further includes manipulating the device in the blood vessel in response to the output. In some embodiments, the manipulating step further includes withdrawing the instrument and/or advancing the instrument.

Another aspect of the invention includes a computer readable storage medium. The computer readable medium includes a program that can be executed by a processor to perform a method for positioning an endovascular instrument in a vasculature. The method includes manipulating a reflected acoustic signal from a sensor on the instrument positioned within a blood vessel to extract one or more acoustic features from the acoustic signal; manipulating an electrical signal from a lead on the instrument positioned within a blood vessel to extract one or more electrical features from the electrical signal; generating an output related to guidance or a position of the instrument within the blood vessel using a computer readable set of rules to evaluate the one or more extracted features; and displaying one of a predetermined number of indications of guidance or position corresponding to the output.

In some embodiments, the computer readable set of rules to evaluate the one or more extracted features includes one or more predefined membership functions that indicate one or more positional states of the instrument.

In some embodiments, the method further includes inputting the extracted features into the one or more predefined membership functions and for generating one or more scores that indicate the likelihood of membership in one or more positional states; weighting the extracted features or one or more membership functions before generating one or more scores; selecting the highest score and determining the positional state based on the highest score. In some embodiments, weighting the extracted features or one or more membership functions includes applying weighting factors to the extracted features or one or more membership functions. In some embodiments, the weighting factors apply less weight to an extracted feature or one more membership function based on a weak acoustic or electrical signal. In some embodiments, the weighting factors apply more weight to an extracted feature or one more membership function based on a strong acoustic or electrical signal.

In some embodiments, one score of the one or more scores relates extracted acoustic features to the direction of movement of the instrument relative to flow in the vasculature; to the overall flow energy in the vasculature measured by the sensor; and/or to the overall flow velocity in the vasculature measured by the sensor.

In some embodiments, the one or more acoustic features corresponds to a ratio of a low frequency flow power to a high frequency flow power; to an acoustic signal obtained during a portion of a heart beat; to the portion of a heart beat during the occurrence of retrograde flow produced by atrial contraction; to the portion of a heart beat during the occurrence of retrograde flow at the end of systole; and/or to the portion of a heart beat during the occurrence of antegrade flow during diastole.

In some embodiments, the one or more electrical features corresponds to a portion of an QRS complex; to a ratio of a magnitude of a P-wave measured by the sensing electrode and a magnitude of a P-wave measured by an external electrode; and/or to an indication of the presence of a biphasic P-wave.

Another aspect of the invention includes a method of determining a position of a medical device in the vasculature of a patient. The method includes transmitting a signal in the vasculature comprising an ultrasound signal from a distal end of a device; receiving a reflected ultrasound signal; extracting an ultrasound feature from the reflected ultrasound signal; receiving an electrical signal from a lead on the device; extracting an ECG feature from the received electrical signal; calculating a plurality of indicator scores using the extracted features; and identifying a positional state by comparing the indicator scores. In some embodiments, each feature infers a distinct position in the vasculature.

In some embodiments, the calculating step further includes inputting the extracted features into a plurality of indicator equations representing positioning probabilities. In some embodiments, the indicator equations correspond to membership functions. In some embodiments, the indicator equations further include applying a weighting factor related to the extracted feature used in the indicator equation.

In some embodiments, the identifying step further includes selecting the positional state that corresponds to the highest indicator score.

In some embodiments, the calculating step further includes solving preset equations based on a correlation between an extracted feature and a probability of a particular position or state of navigation of the device.

In some embodiments, one indicator score in the plurality of indicator scores relates extracted acoustic features to the direction of movement of the device relative to flow in the vasculature; acoustic features to the overall flow energy in the vasculature measured by the sensor; and/or acoustic features to the overall flow velocity in the vasculature measured by the sensor.

Although certain aspects or features of the invention have been disclosed in connection with certain embodiments, it is understood that these aspects or features can be incorporated with any of the other embodiments disclosed herein, as appropriate.

The systems and methods of the present invention have other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 is a block diagram of the software/processing system of FIG. 1.

FIG. 7 also illustrates the use of A-mode imaging for clot identification inside the blood stream or inside an endovascular member.

FIG. 12B illustrates an intravascular ECG signal indicating the amplitude of the RS portion of the signal in a brachial vein portion and in the portion of the caval atrial junction (CAJ).

FIG. 23 illustrates exemplary states of navigation and system outputs.

DETAILED DESCRIPTION OF THE INVENTION

Figure 1:
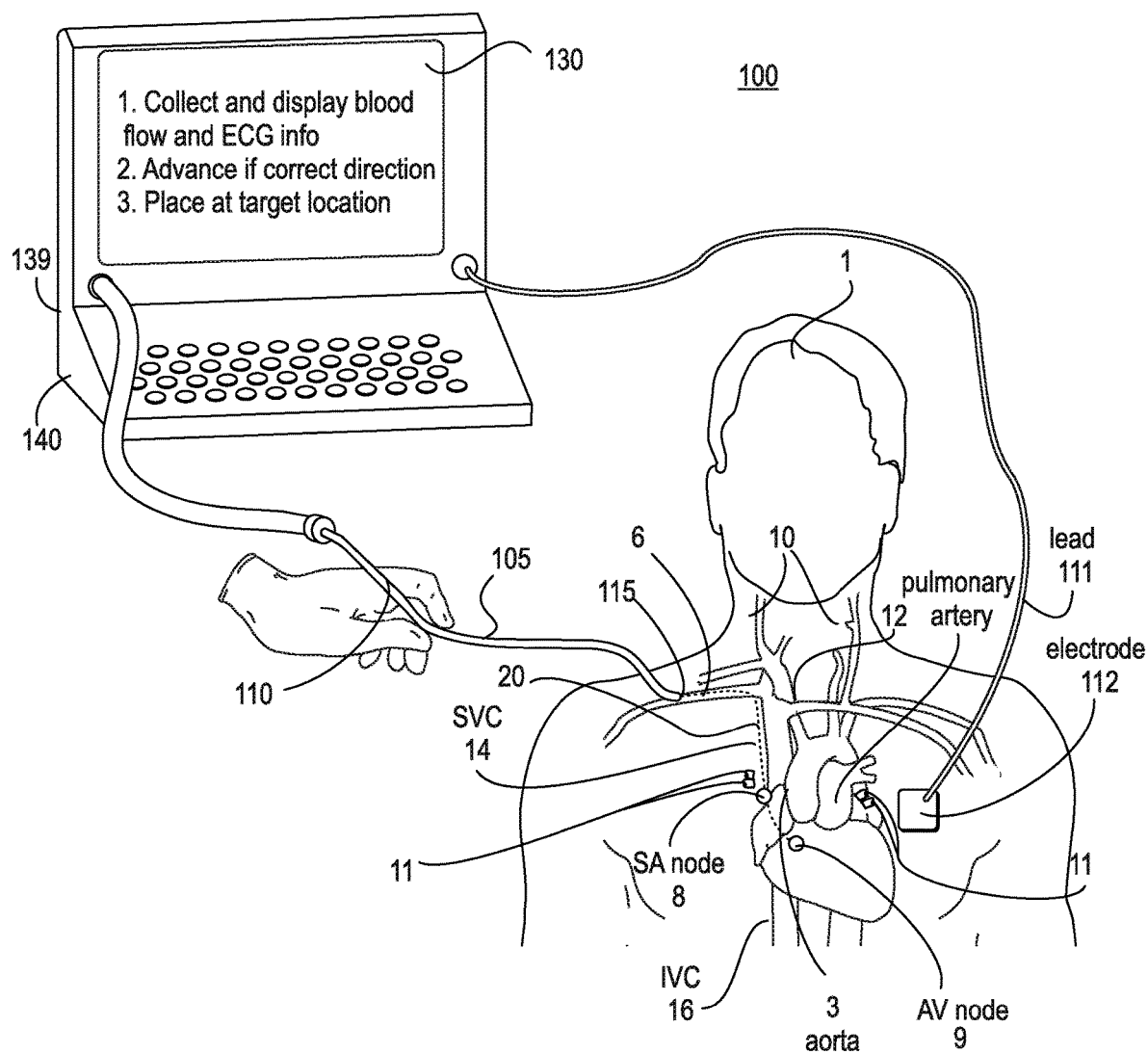
FIG. 1 illustrates an overview of an endovascular device guiding system and method disclosed in accordance with the invention.

For convenience in explanation and accurate definition in the appended claims and following description, the terms "up" or "upper", "down" or "lower", "inside" and "outside" are used to describe features of the present invention with reference to the positions of such features as displayed in the figures.

Patient data has long been used for diagnostic and therapeutic techniques. Various features may be measured, monitored, and analyzed for myriad purposes such as identifying a medical condition or performing a medical procedure. Improvements in medical technology have led to the use of patient monitoring for far more applications. The advance of computer technology and its integration into the medical field has significantly expanded the applications for analysis of patient data. For example, U.S. Pat. No. 6,179,782 to Cuce, incorporated herein for all purposes by reference, discloses a system for classifying a patient and identifying a medical indication by coupling a fuzzy logic processor to a conventional blood pressure cuff monitoring arterial pressure.

The broad class of systems and methods for monitoring and collecting patient data can be categorized based on several distinctions. For one, the system may either collect data for analysis at least somewhat contemporaneously or store the data for analysis later. For another, the system may use the patient data for therapeutic, surgical, or diagnostic purposes. Of course, some system and methods can be used for multiple purposes and in multiples ways.

Various aspects of the invention relate to a system and methods for navigating and positioning a device in the body. Various aspects of the invention relate to a system and methods for navigating and positioning a device in the vasculature. The use of patient data for navigating and positioning devices in the vasculature has long been used. A conventional technique involves placing a device in the superior vena cava (SVC) just short of the right atrium. In a typical procedure, the device is inserted into the body (e.g. percutaneously) and moved towards the heart. An ECG signal is displayed on a monitor as the device moves. The user compares the P-wave on the monitor and identifies a particular location by identifying changes to the P-wave. An example of this method is disclosed by U.S. Pat. No. 5,078,678 entitled "Method and Apparatus for Locating a Catheter Adjacent to a Pacemaker Node of the Heart," to Katims, the entire contents of which are incorporated herein for all purposes.

Conventional methods for navigating and positioning devices in the vasculature have several drawbacks. A significant limitation is the fact that the system relies on the user to notice even minute changes to the P-wave. The user must recognize specific and nuanced P-wave shapes, amplitudes, and trends, all while busy performing the actual procedure. Additionally, the technique is useful for identifying a specific location—the SVC at an entrance to the right atrium—but does not generally provide for the general positioning of devices in other locations. This is a problem in that the lower third of the SVC is considered to be more optimal for many applications (e.g. dilation and drug delivery) than the bottom of the SVC. The system also does not provide navigation. The user has no indication of location. The user merely recognizes a shift when a target is passed and then has to withdraw the device back to the target.

Various aspects of the invention relate to use of a plurality of input variables related to the body and its functioning for therapy and diagnosis. In the context of the cardiovascular system, for example, many inputs can be used for a single application. Many inputs used by the system in accordance with aspects of the invention are considered as noise or useless by conventional systems and techniques. The system generally makes use of sophisticated processing techniques to read, interpret, and analyze complicated information for specific purposes. For example, conventional systems typically cannot be used in the venous vasculature because the blood flow is so turbulent and complicated as to be wholly indecipherable by a user.

Various aspects of the invention are directed to collecting the huge amounts of data long considered as an impediment (e.g. noise) and advantageously using the data to improve performance and/or accomplish tasks previously considered impossible. For example, various aspects of the invention relate to a non-imaging system and methods for navigating and positioning a device in the venous vasculature as opposed to the arterial vasculature. The system may make use of intravenous information without the use an X-ray, fluoroscopy, and conventional methods. Various aspects of the invention relate to a system and methods for navigating and positioning a device in the body using a plurality of information related to the patient, and more specifically, related to the patient's cardiovascular system.

In various respects, the present invention provides new methods, devices and systems for intravascular guidance and placement of endovascular devices based on the recognition of patterns in the signals for different physiological features and correlation of those signal patterns.

Aspects of the current invention overcome the above described limitations and provided accuracy by applying a guidance system to the obtained physiological signals. The guidance system of the invention takes into account the variable nature of the obtained physiological features, the relationship of one or more physiologic signals to specific locations in the vasculature, and the degree of accuracy provided during the different phases of endovascular navigation. The output of the positioning system provides indications to a user in the form of navigation instructions and/or position information.

The exemplary system will now be described generally with reference to FIGS. 1, 2, 3A, 3B, 4A-4C, 5A, 5B, 6, 7, and 8A-8D. Further details of the system will be provided below.

An exemplary device in accordance with various aspects of the invention is shown. Embodiments of the present invention include a pre-processor for obtaining one or more physiological signals and pre-processing the obtained signals to extract desired features and provide inputs to a processor. Various aspects of the pre-processor are similar to conventional signal processing and medical diagnostic systems. U.S. Pat. No. 6,007,491 to Ling et al., incorporated herein for all purposes by reference, discloses a cardiac output monitor. The system analyzes a blood pressure waveform in part by extracting desired feature parameters. The system receives the blood pressure waveform as an input, digitizes the input, and then extracts selected blood pressure features for use as inputs in a fuzzy logic model.

Figure 9:
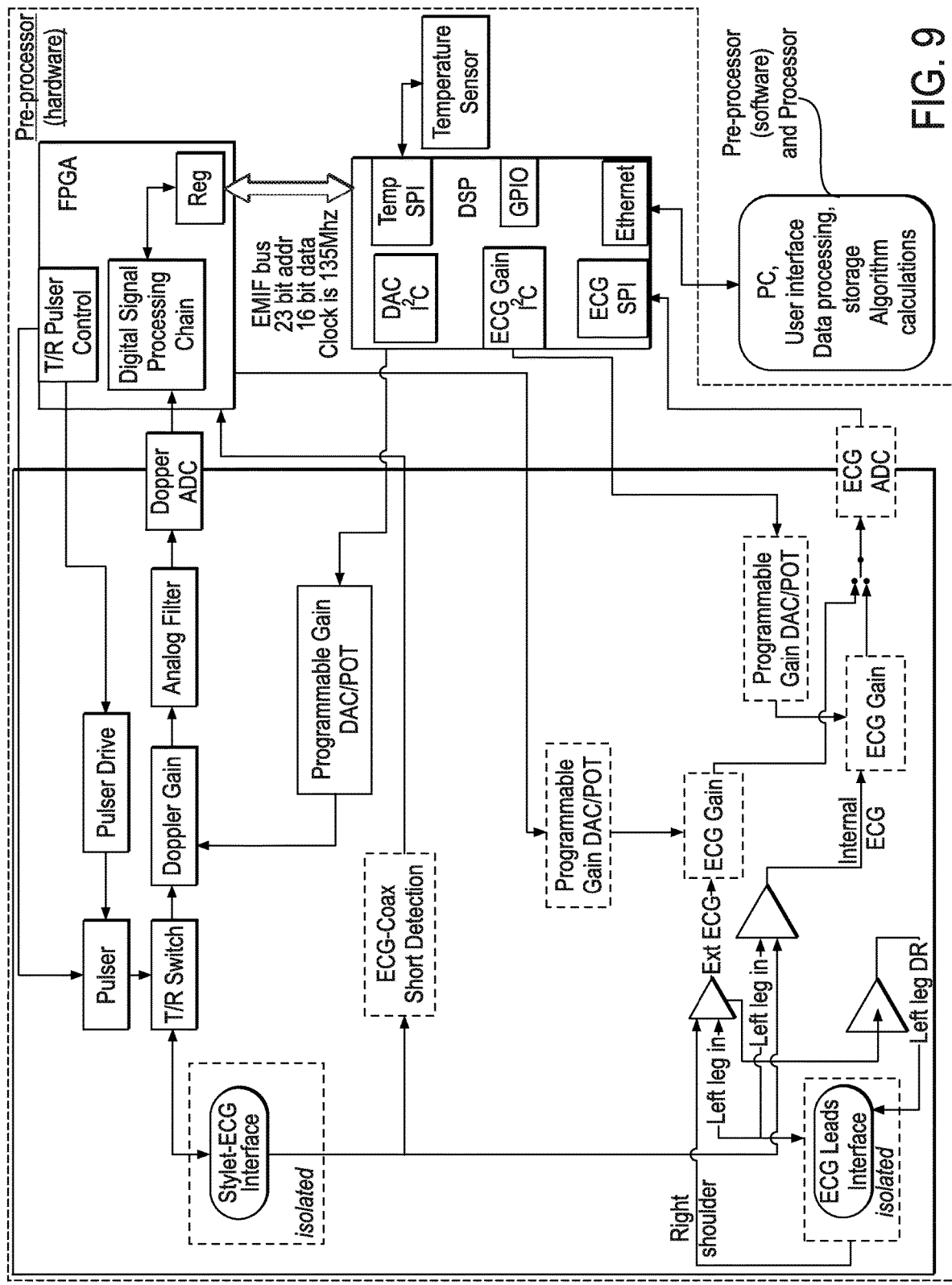
FIG. 9 is a block diagram of an endovascular guidance system in accordance with the invention, illustrating pre-processor and processor circuitry for manipulating a Doppler signal and optional ECG signal.

An exemplary pre-processor is shown in FIG. 9. The pre-processor includes hardware and software. The software may be implemented in the exemplary personal computer (PC). The other features shown in the figure generally relate to the hardware for the sensors and pre-processor hardware. The software may be configured to pre-process the raw data. The hardware may be configured to extract specified feature information from the signal data processed by the software.

The pre-processing may include, but is not limited to, conversion of a Doppler or an ECG signal from the time domain to the frequency domain, frequency to time domain, amplification, filtering, analog-to-digital conversion, and partitioning of an ECG waveform to extract one or more ECG features, partitioning of an acoustic waveform to extract one or more acoustic features. The pre-processing can be performed on any inputs or features or signal described herein, such as Doppler signals, ECG signals or other natural or artificial sources, for example.

The features are transmitted to the processor as inputs. The processor then evaluates the pre-processed inputs to obtain precise and accurate location and/or guidance information for output and display to the user. The processor may process the pre-processed inputs using artificial intelligence such as a predetermined set of processing rules, inference statements, and the like.

Various functions of the pre-processor and processor are similar to those employed by existing medical diagnostic devices. U.S. Pat. No. 7,627,386 to Mo et al., incorporated herein for all purposes by reference, discloses an ultrasound system making use of a neural network processor and fuzzy logic controller. The Mo system employs the different processors and controllers to optimize the ultrasound images for clinical diagnosis. U.S. Pat. No. 6,179,781 to Phillips, incorporated herein for all purposes by reference, discloses a processor that assigns weights to feature parameters to improve the accuracy of a medical diagnostic ultrasound apparatus. U.S. Pat. No. 6,179,782 to Cuce, incorporated herein for all purposes by reference, discloses use of a fuzzy logic processor to more accurately measure arterial pressure. U.S. Pat. No. 7,966,061 to Al-Abed et al., incorporated herein for all purposes by reference, discloses a system for detecting a sleep disorder. The Al-Abed system uses statistical analysis to formulate inference rules for a fuzzy logic processor which analyzes an external ECG waveform. These and other references are directed to different purposes, signal data, and patient populations than the invention; however, these references are representative of the integration of computer processing techniques into the medical diagnostics field. Various aspects of the invention are directed to improve processing techniques. Various aspects of the invention are directed analyzing hemodynamic data for navigation and positioning within the vascular system, and in some respects, the venous vasculature.

As will be discussed in greater detail below, the pre-processor and/or processor in accordance with the invention may employ artificial intelligence features. "Artificial intelligence" is used broadly to refer to a large collection of advanced processing techniques including, but not limited to, logic (e.g. fuzzy logic, Bayesian probability, two-valued logic, and sentential logic), probabilistic reasoning, an expert system, one or more pattern recognition technique, a neural network, an inference engine, classifiers, and combinations of the same.

An input signal is obtained from the body and used to determine the location or relative movement of a device positioned within the body. In various embodiments, two different input signals are obtained from the body. The input signals are typically amplified, filtered or converted as is typical in the digitalization of analog signals and other signal processing techniques. These collected signals are then pre-processed to produce one or more parameter inputs for use in a processor/controller.

In various embodiments, the system acquires two or more signals and at least one of the signals is used as a confirmation signal. For example, the system may acquire a Doppler signal and an ECG signal. The system may process one of the signals and output a result. The result may be confirmed by independent processing of the other signal. For example, the system may rely primarily on Doppler-based guidance but use the ECG signal to confirm the Doppler-based result. In this way the system may provide improved confidence levels.

One will appreciate from the description herein that the system may acquire and process signals over a variety of time periods. In one example, ECG and Doppler signals are analyzed over time intervals that range from less than one heart beat (i.e., during a portion of a QRS complex or during the same portion of a QRS complex on sequential heartbeats) to a heart beat during patient inspiration, expiration, or during a portion of a respiration cycle or sequential respiration cycles. Multiple time intervals could be analyzed together using various membership functions.

Endovascular Member with Sensors for Guidance

Figure 2:
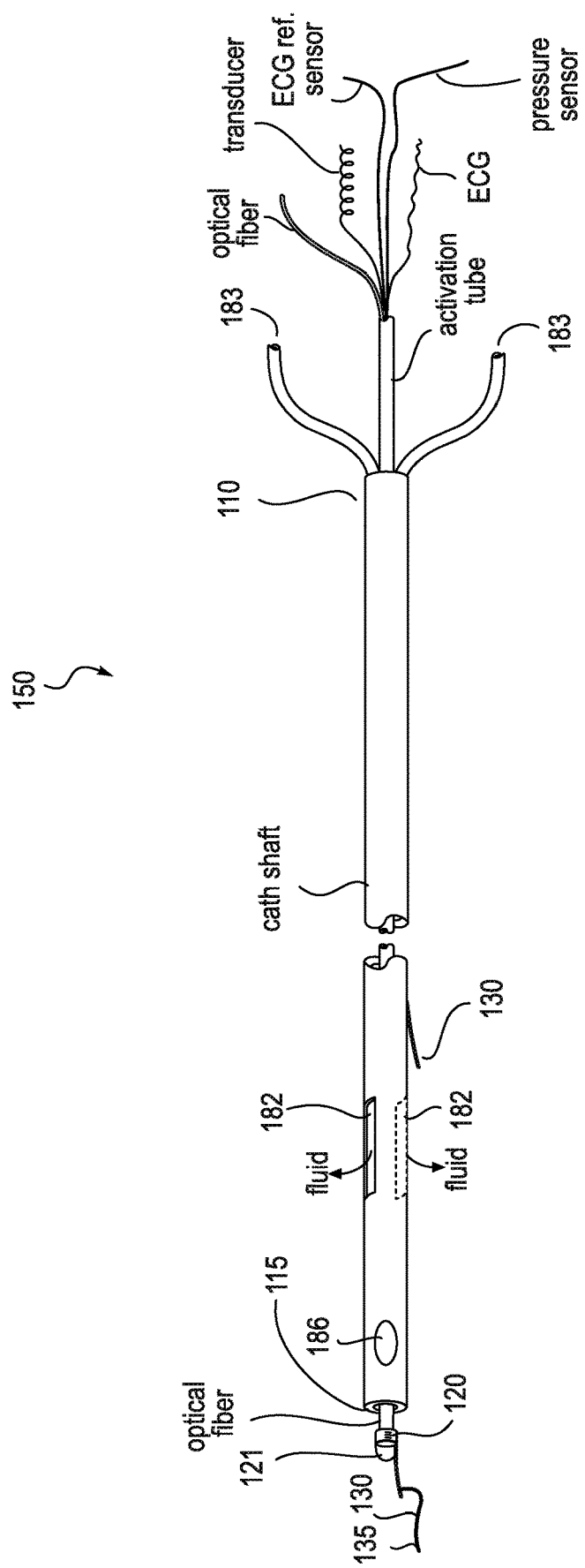
FIG. 2 illustrates an endovascular device with multiple sensors.

FIGS. 1-2 illustrate an exemplary endovascular access and guidance system 100 including a catheter is shown. The system and exemplary catheter are similar in many respects to those described in U.S. Patent Pub. No. 2009/0005675 to Grunwald et al., the entire contents of which is incorporated herein for all purposes.

The exemplary device is configured to obtain two different physiological signals from the body, in particular, a Doppler signal (an in vivo, non-image-based ultrasound signal) and an ECG signal. One will appreciate from the following description, however, that the system may operate using only a Doppler signal or only an ECG signal. One will further appreciate that the system is not limited to Doppler or ECG; other signals as will be understood by one of skill from the description herein may be used. Examples of other measurable information that may be useful in the invention include, but are not limited to, oxygen saturation, cardiac output, heart rate, blood pressure, temperature, and respiration rate.

The illustrated system 100 includes a peripherally inserted central catheter (PICC). One will appreciate that the system may be paired with other medical devices such as an endoscope. The exemplary catheter includes an elongate body 105 with a proximal end 110 and a distal end 115. The exemplary elongate body 105 is any of a variety of endovascular devices adapted for insertion into and navigation through the vasculature of the patient 1. FIG. 1 illustrates the distal end 115 inserted into the basilic vein 6, for example. The expected path of travel (dashed line 20) in this illustrative example is into a portion of the heart 20 or within the superior vena cava 14 in proximity to the sinoatrial node (SA node) 8. The aorta 3, the pulmonary arteries, the pulmonary veins 11, the jugular veins 10, the brachiocephalic vein 12, the inferior vena cava 16, and the atrioventricular node (AV node) 9 are also represented in this view.

Not shown in FIG. 1, but further described below, the exemplary elongate body 105 includes a first ultrasound sensor and one or more optional sensors for measuring physiological features in the body. In some embodiments, the first sensor is a non-imaging ultrasound transducer 120 on the elongate body 105 configured to provide in vivo non-image based ultrasound information of the vasculature of the patient 1. In some embodiments, the one or more optional sensors is an endovascular electrocardiogram lead on the elongate body 105 in a position such that, when the elongate body 105 is in the vasculature, the endovascular electrocardiogram lead electrical sensing segment provides an in vivo electrocardiogram signal of the patient 1. In various embodiments, the elongate body 105 includes two or more ultrasound sensors spaced apart by a specified distance. FIG. 1 illustrates the use of a second electrocardiogram sensor that is outside of the vasculature. The electrode 112 is positioned external to the vasculature of the patient 1. The electrode 112 detects electrocardiogram information that is transmitted via lead 111 to the processor 140. In various embodiments, the system includes a plurality of external ECG sensors. For example, although only a single lead or electrode is shown in shown in FIG. 1 for illustrative purposes, it is understood that a plurality of external ECG electrodes can be used, such as a 3 electrode system that is placed to form a triangle around the patient's heart. In other embodiments, a standard 5 electrode system can be used. Similarly, the signals may be generated by one or more structures in the body or external to the body.

In various embodiments, in place of the electrode 112, or in addition to the electrode 112, another electrocardiogram sensor may be placed on the elongate body 105. More than one electrocardiogram sensor may be provided on the elongate body. In this case, the processor 140 would also be configured to receive, process, compare and correlate the electrocardiogram information from the additional electrocardiogram sensor (or other sensors) provided by the elongate body 105.

The electrocardiogram leads or sensors on the elongate body 105 may also be placed relative to the elongate body 105 and to one another in order to obtain a target electrocardiogram signal and a baseline electrocardiogram signal in order to facilitate the position and location capabilities of the guidance system 100. The target and baseline electrocardiogram information may be related to one or more of: (a) electrical activity of the heart including all or a portion of an electrocardiogram (ECG); (b) electrical activity of the brain including all or part of an electroencephalogram (EEG); and (c) electrical activity of a muscle or muscle group including all or part of an electromyogram (EMG) related to that muscle or muscle group. Additional details of the sensors and the various alternative configurations of the elongate body 105 are described below with respect to at least FIGS. 2-5B.

The system 100 also includes an output device 130 configured to display a result of information processed by the processor 140. The display device may, like the processor 140, include capabilities found in conventional display devices among other capabilities. The display device 140 of the invention differs from the conventional display in that the display is configured to display information related to the unique processing and results determined by processor 140. In particular, rather than displaying acquired signal information, the output device displays straightforward indicators to the clinician based on the underlying processing of the signals. Unlike conventional displays, the user does not need to have considerable experience interpreting signal information nor engage in the time-consuming and complicated process of interpreting the signal information in real-time.

In one aspect, the output device 140 displays a result related to a position of the elongate body within the vasculature of the patient. In another aspect, a result of information processed by the processor includes an indication of a position or a movement of the elongate body 105 within the vasculature based on in vivo non-image based ultrasound information and in vivo electrocardiogram information. The display 130 would be configured to display this information for a user to perceive in any suitable manner such as visually, with colors, with pictograms, with sounds or in other appropriate manners.

FIGS. 7, 8A, 8B, 8C, and 8D illustrate an alternative output device whereby indicators having specific shapes, sizes, and/or colors relate to the user the exact position of the device in the vasculature. FIGS. 8A, 8B, 8C, and 8D illustrate the positions corresponding to each indicator. The indicators may be any color, icon, and sound, or any other kind of graphical, alphanumeric, and/or audible elements to indicate the tip location in an easy-to-understand manner.

The exemplary output device also displays a variety of other information to the user such as tracing of the received Doppler signals and a meter representing the relative contributions of antegrade and retrograde flow. The exemplary output device also includes a number of controls and instrument displays.

In an exemplary embodiment, Doppler and/or ECG signals are used to determine the catheter tip location. In various embodiments, the system makes use of the fact that, during the catheter insertion, the physiological characteristics of the input signals are different in different positions. In various embodiments, artificial intelligence is used to derive positional information from the sensor signals to guide the tip to and land at optimal desired position (e.g. the lower ⅓ of superior vena cava (SVC) and the catheter tip heading to atrium). The two signals are amplified, sampled, and filtered along with other appropriate pre-processing operations to render the signal information as one or more features. These features become inputs to a processor. The processor then processes the input and outputs a result indicative of the position and/or direction of the tip. Parameters associated with the feature and algorithms generally include constants, coefficients and weighing factors, for example, that can be adjusted to fine tune the algorithms.

In an exemplary Doppler channel, the transmitter center frequency is about 11.667 MHz, outputting a burst of about 8 pulses at a pulse repetition frequency (PRF) of approximately 30 kHz. The received Doppler signal may be amplified, sampled, down-converted or otherwise appropriately subjected to operations to yield features used as inputs to the guidance system, and in particular, the pre-processor.

The operating frequency and PRF typically depend on the hardware and the device environment. The exemplary system for insertion and navigation in the venous environment has a selected operating frequency of between about 8 MHz and about 15 MHz, and in various respects between about 10 MHz to about 12 MHz. In various embodiments, the operating frequency is about 12 MHz. The operating frequency may be higher or lower depending on the applications. For example, conventional coronary artery systems operate at around 20 MHz.

The PRF drives the signal generation and acquisition. Among other things, the PRF in combination with the operating frequency determines the resolution of the signal. For example, if the PRF is too low the system will not acquire useful data. Generally, a higher PRF provides more flow information but emits more energy into the patient. Thus, if the PRF is too high the system may present a health risk to the patient. In various embodiments, the PRF is between about 30 kHz to about 45 kHz. In various embodiments, the PRF is below 60 kHz, below 50 kHz, below 40 kHz, or below 30 kHz. In various embodiments, the PRF is about 30 kHz or about 40 kHz. By contrast, the PRF needs to be significantly higher for use in the arterial system. Typically, PRF must be around 100 kHz or higher in the arterial system.

During the insertion, the exemplary guidance system provides four different signs or output indications: a green arrow, the blue bull's eye, a red stop indicator, and yellow bar, to guide the clinical operator to reach the optimal position (shown in FIGS. 7, 8A, 8B, 8C, and 8D). As will be described in greater detail below, the exemplary processor is designed around the probability that the device is in one of four navigational states. State 0, state 1, state 2, and state 3 are used to represent yellow (i.e. caution and/or more data needed), green arrow (i.e. go forward), the blue bull's eye (i.e. landing zone achieved), and red circle (i.e. wrong direction, pull back), respectively. The exemplary four states will be described in greater detail below with respect to Tables 1-5. Note that the term "zone" can be used interchangeably with the term "state." The system described includes four states for illustration purposes. One will appreciate from the description herein that more or less states may be provided for in the processor.

Various aspects of the invention relate to the use of intravascularly-measured physiological parameters for locating, guiding, and placing catheters in the vasculature. Various aspects of the invention relate to an endovascular member assembly with built-in sensors for measuring of physiological parameters such as blood flow, velocity, and pressure. Various aspects of the invention relate to an assembly for further measuring intravascular ECG.

Various aspects of the invention relate to data processing algorithms that can identify and recognize different locations in the vasculature based on the pattern of physiological parameters measured at that location. FIG. 6 illustrates an exemplary software block diagram 4 for providing the processing capabilities used by embodiments of the present invention.

Various aspects of the present invention relate to data processing algorithms that can identify and recognize structures such as objects of interest in the vasculature or in endovascular members, for example, blood clots based on the pattern of parameters measured (e.g., A-mode and blood flow velocity). Various aspects of the invention relate to an instrument that has a user interface which shows guiding and positioning information and presents the objects of interest (e.g. blood clots). For example, in this aspect the processor is further configured to process a signal from the non-image ultrasound transducer and to indicate in the output device information related to the presence of a structure in the field of view of the non-imaging ultrasound transducer. In various embodiments, the system can draw conclusions from the location information and even make recommendations to the user.

Various aspects of the invention relate to a method of guiding and positioning an endovascular member within the vasculature by the user based on location information provided by the sensor-based endovascular member. Other various aspects of embodiments the invention relate to the use of intravascularly measured physiological parameters for locating, guiding, and placing catheters or stylets or guide wires for use as guides to particular locations within the vasculature that have been identified using the guided vascular access devices and systems described herein.

FIGS. 2, 3A, 3B, 4A and 4B illustrate an endovascular device 150 in accordance with various aspects of the invention having an elongate body 105 with a proximal end 110 and a distal end 115. A non-imaging ultrasound transducer 120 is provided on the elongate body 105. An atraumatic tip 121 is provided on the endovascular device 150. The atraumatic tip 121 may also include an ultrasound lens. The ultrasound lens may be used to shape the ultrasound signal produced by the ultrasound transducer 120. In one aspect, the ultrasound lens is a divergent lens.

The endovascular device 150 also has an opening 182 in the elongate body 105 and a lumen within the elongate body 105 in communication with the opening 182 and the elongate body proximal end 110. As illustrated, there may be one or more openings 182 in communication with one or more lumens or tubes 183. Also shown on the proximal end 110 are the various connections to the sensors and lumens in the endovascular device 150. These connections are conventional and may take any suitable form to connect the endovascular device to the other guidance system 100 components such as the processor, display or fluid delivery device. As such, by using additional lumens or other access features, the elongate body 105 or endovascular device 150 is adapted to deliver a therapy to the patient such as by delivering drugs, therapeutic or diagnostic agents through the openings 182 or between the inner and outer tubes. In yet another alternative configuration, the elongate body 105 or the endovascular device 150 is adapted to provide endovascular access for another device.

One will appreciate that other additional and optional sensors may be provided on the endovascular device 150. Embodiments of the endovascular device 150 may contain any of a number of different sensors. The sensor is selected based on the physiological parameter to be measured and used in the guidance, positioning and correlation methods described herein. By way of non-limiting example, the device may include an ultrasound sensor, a conductive wire, a pressure sensor, a temperature sensor, a sensor for detecting or measuring electrical potential and voltages and other sensors suited to collecting physiological information and providing information to the processor 140 for processing in an algorithm or for other suitable form of analysis based on the techniques described herein. The sensor-based endovascular device 150 can be used independently to deliver a payload into the vasculature, e.g., a drug or to draw blood or it can be inserted into the one of the lumens of another endovascular device, e.g., a catheter. Then the entire assembly can be inserted into the patient's body, e.g., for a PICC placement procedure, or through a catheter 90 (shown in FIG. 4C).

Additionally or alternatively, the endovascular device 150 can be configured as any type of catheter, stylet, guidewire, an introducer, a combination thereof or any other type of device which allows for vascular access. The endovascular device and the corresponding connection from the sensors to the proximal end can either be fixed in the endovascular device, or pre-inserted and removable after procedure, or reinsertable for location verification post placement. In one embodiment the endovascular device integrates a single lead electrode for electrical activity monitoring. In a different embodiment, the endovascular device may integrate several electrodes (leads), for example one at the very distal tip of the endovascular member and one more proximal such that the distal electrode can detect the electrical activity of the heart while the more proximal electrode can serve as a reference for measuring since the more proximal electrode is closer to the patient's skin and further away from the heart. In addition to providing electrical mapping, the lead/electrode can be used as a steering element to steer and position the endovascular device as illustrated in FIGS. 3A, 3B, 4A and 4B.

According to the embodiments of the present invention physiological information is acquired by sensors and transmitted to a processor. The processor uses algorithms which analyze and process the sensor data to provide information on the location of the sensor core assembly and of the corresponding endovascular device in the patient's vasculature. Since high degree of accuracy is desired, different types of physiological information, ideally independent from each other, such as blood flow information and electrocardiogram information are used to accurately characterize the direction of movement and location. In one aspect of the present invention, the described clinical need is met by gathering physiological information regarding blood flow using ultrasound and regarding the electrical activity of the heart by acquiring endovascular electrical signals.

By way of example, the endovascular device embodiments of FIGS. 3A, 3B, 5A, 5B, include an elongate body 105 that may be configured as any of a catheter, a stylet, or a guidewire that is configured for endovascular access. Moreover, the catheter, stylet or guidewire may be of the one part or two part construction described herein.

The endovascular device 150 may be configured as a single structure (shown, e.g., in FIGS. 3A, 3B, 4A, 4B, 5A and 5B). The device may be a removable device or sensor core assembly and may consist of a non-imaging ultrasound transducer mounted at the end of a piece of tubing. The tubing can be single or multi-lumen and can be made of any of a variety of polymeric or elastomeric materials. The lumens may be used to support the sensors on the tubing or may be used for delivery of therapeutic or diagnostic agents. One or more physiological parameter monitoring sensors may be positioned on the tubing as described herein. The endovascular device may have a two part construction as shown in the illustrative embodiment of FIG. 2 where the ultrasound transducer is on a tube (an inner tube) within another tube (an outer tube).

In the illustrative embodiment of FIG. 2, the inner tube carries the ultrasound transducer. The outer tube, possibly a multi-lumen tube, has a lumen for the inner tube. Additionally, lumens 183 are provided to correspond to the openings 182. The outer tube also supports the additional sensors (one sensor 186 is shown). The wiring or other connections for the additional sensors 186 or electrocardiogram lead may also be provided with their own lumen or lumens. The proximal end 110 and the various leads and lumens and other connections may be placed into a single connector used to attach the endovascular device 150 to the other components of the system 100.

Whether the endovascular device 150 is a single tube or a multiple tube construction, the device optionally includes an additional sensor 186 on the endovascular device for measuring a physiological parameter. In one aspect, the additional sensor is an optical sensor and the physiological parameter is related to an optical property detected within the vasculature. In another aspect, the additional sensor is a pressure sensor and the physiological parameter is related to a pressure measurement obtained within the vasculature. In another aspect, the additional sensor is an acoustic sensor and the physiological parameter is related to an acoustic signal detected within the vasculature.

The exemplary system includes an optional endovascular electrocardiogram lead 130 on the elongate body 105 in a position that, when the endovascular device 150 is in the vasculature, the endovascular electrocardiogram lead 130 is in contact with blood. There are two endovascular leads 130 in the illustrated embodiment of FIG. 2. As shown, there is an endovascular electrocardiogram lead 130 positioned at the elongate body distal end 115.

The electrocardiogram lead 130 contains at least one electrical sensing segment 135. The electrical sensing segment 135 is that portion of the electrocardiogram lead 130 that is used for detecting or sensing the electrical activity being measured. The electrical sensing segment 135 could be a portion of the lead 130 that is not insulated, it could be a separate structure, like an electrode, that is joined to the lead 130 or it could be a structure within the endovascular device (shown in FIG. 5B). In one aspect, the electrical sensing segment of an endovascular electrocardiogram lead is positioned within 3 cm of the elongate body distal end 115. In another aspect, the electrical sensing segment 135 of an endovascular electrocardiogram lead 130 is positioned within 3 cm of the non-imaging ultrasound transducer 120. As shown in FIG. 2, this aspect relates to the lead 130 that extends from the distal end or to the spacing of proximally positioned endovascular lead 130. Additionally or alternatively, the electrical sensing segment 135 of an endovascular electrocardiogram lead 130 is positioned proximal to the non-imaging ultrasound transducer 120.

Figure 3A:
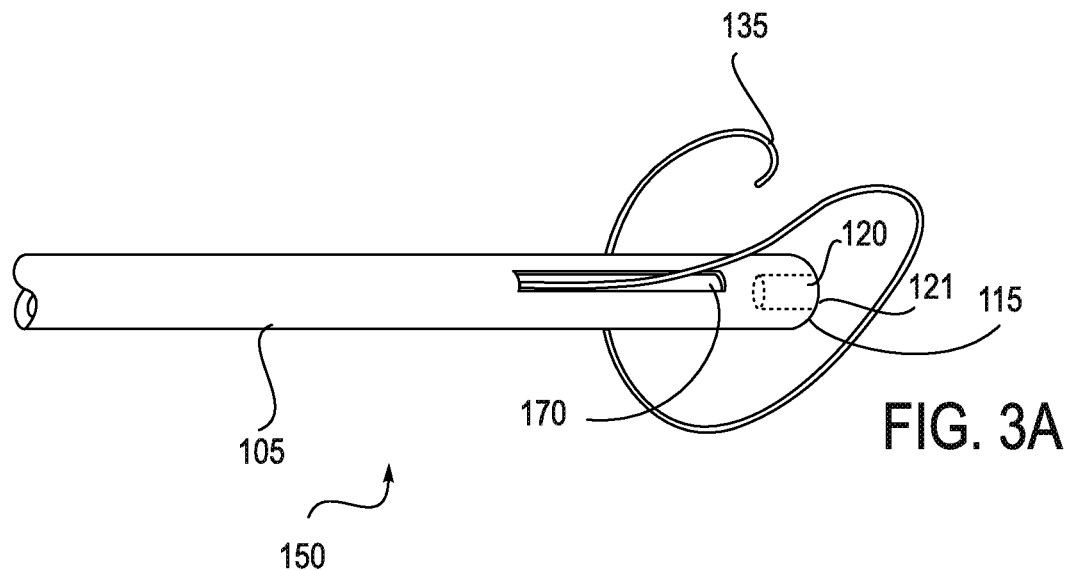
FIGS. 3A-3B illustrate an optional intravascular ECG electrode which can be used for steering and moving the endovascular member away from the vessel wall.
Figure 3B:
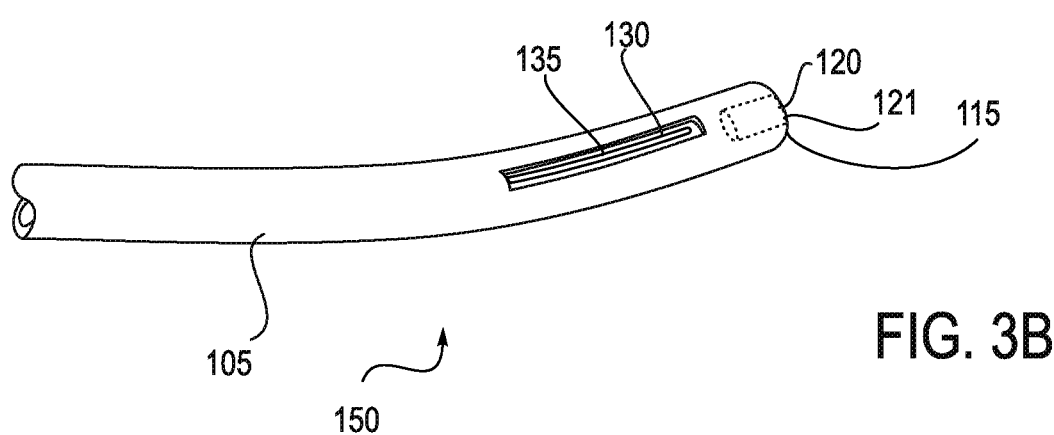
Figure 4A:
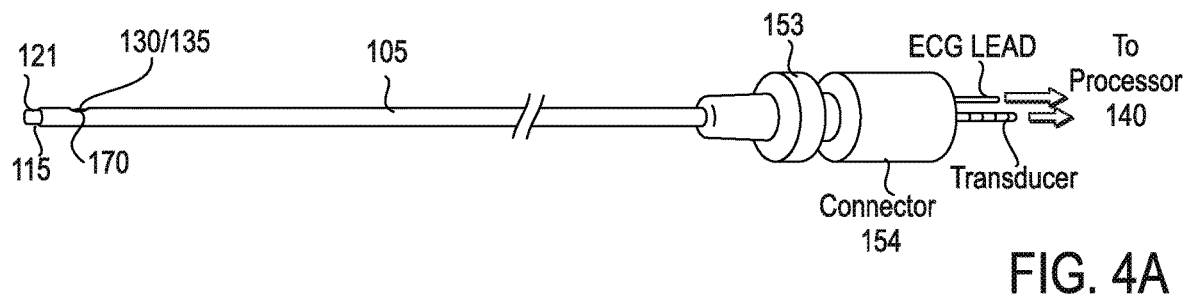
FIGS. 4A-4C illustrate the concept of a removable sensor core, whereby a stylet with integrated sensors can be inserted into and removed from an endovascular device like a catheter at any time.
Figure 4B:
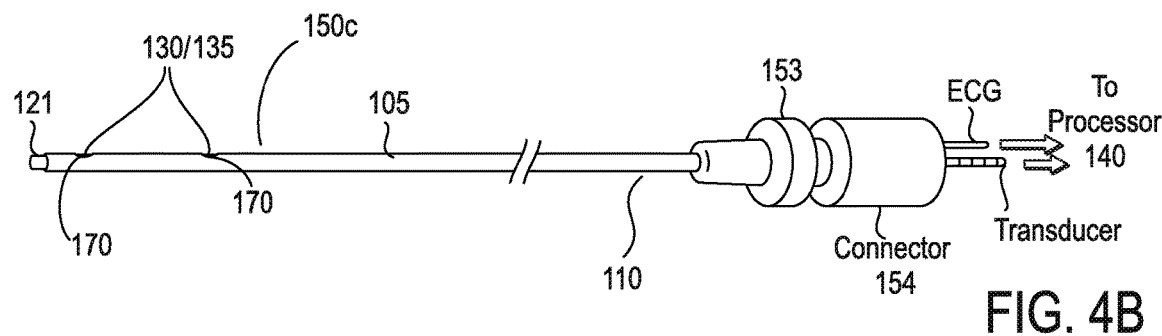
Figure 4C:
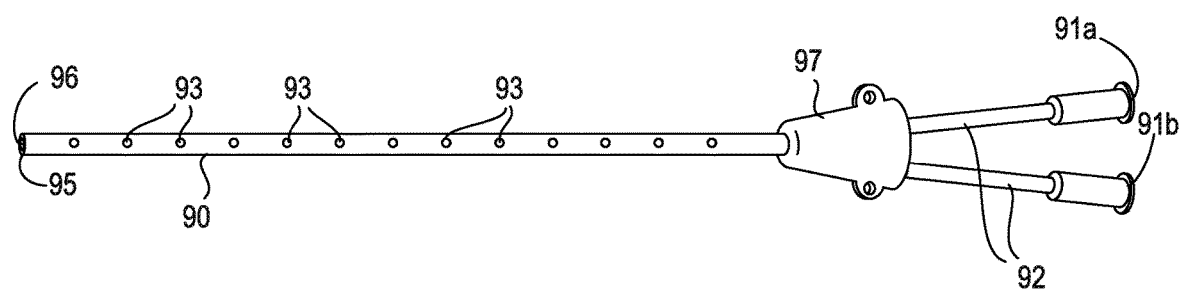
Figure 5A:
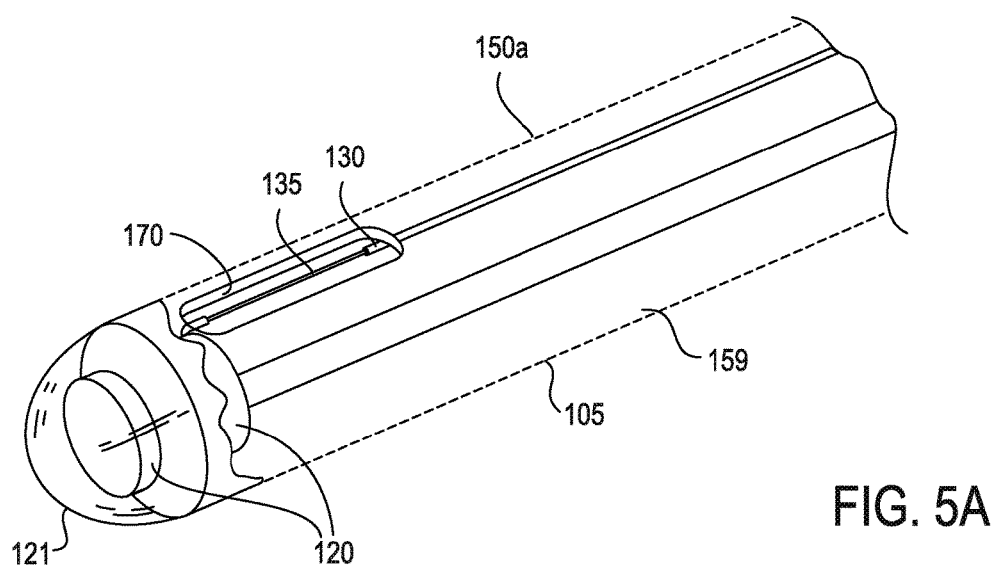
FIGS. 5A-5B illustrate an embodiment of integrated sensors in an endovascular device with a braided shaft and atraumatic tip.
Figure 5B:
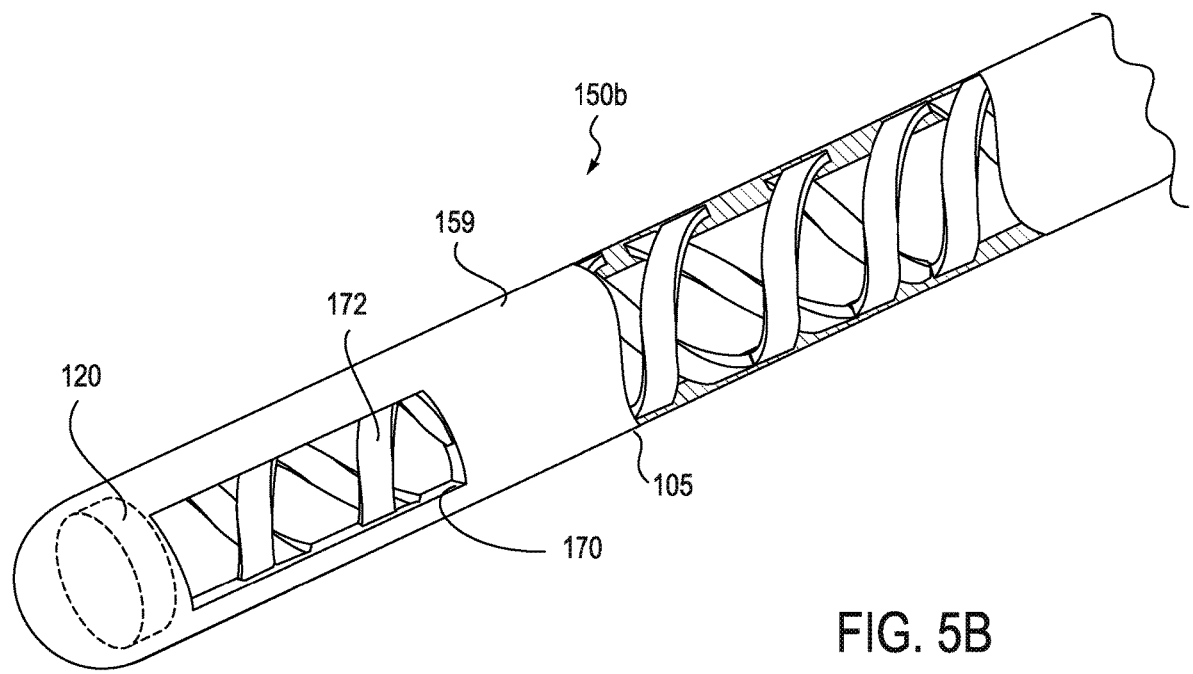
Figure 7:
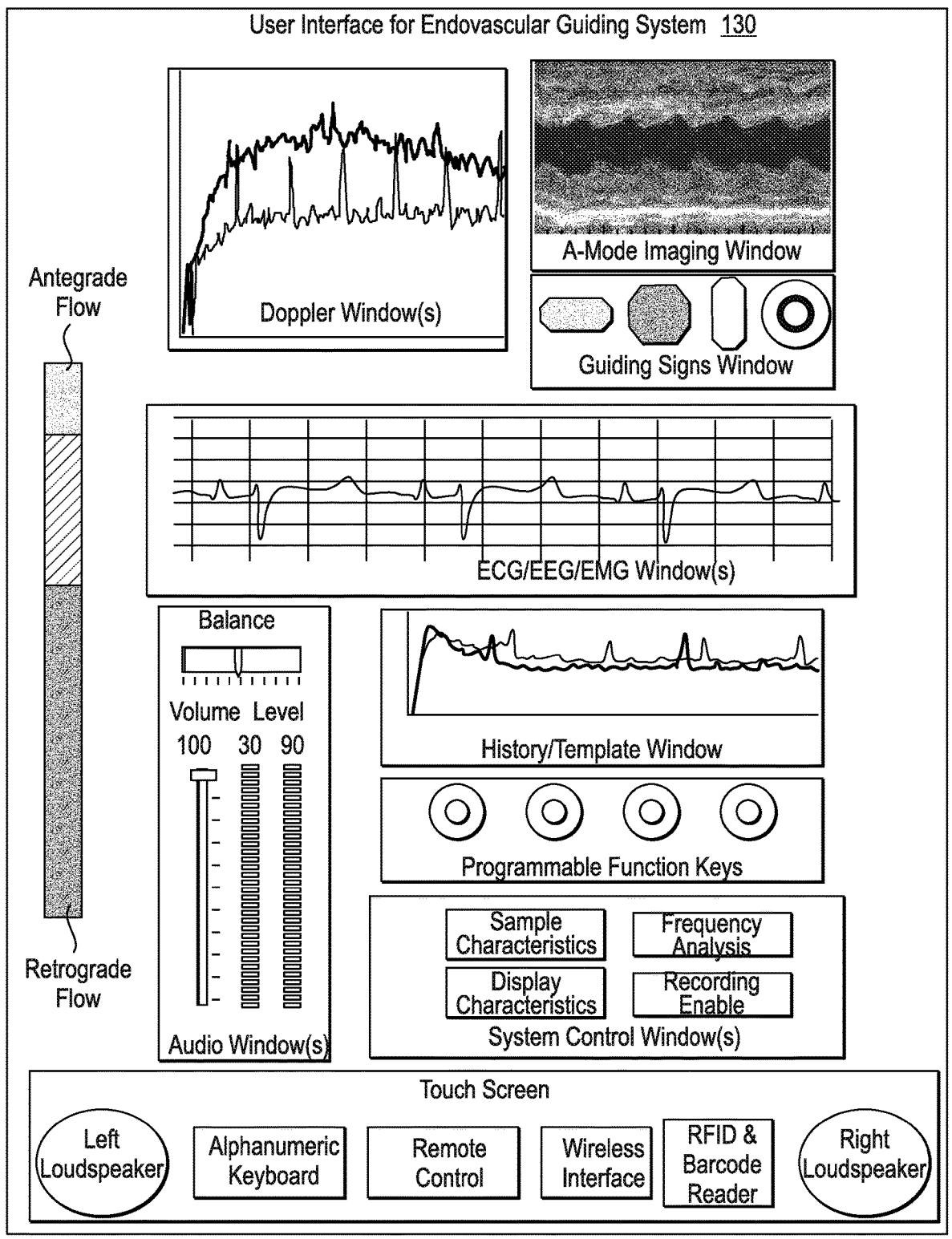
FIG. 7 illustrates a graphical user interface displaying blood flow information, intravascular ECG signals, their correlation, and catheter tip location information based on the processing method in accordance with the invention.
Figure 8A:
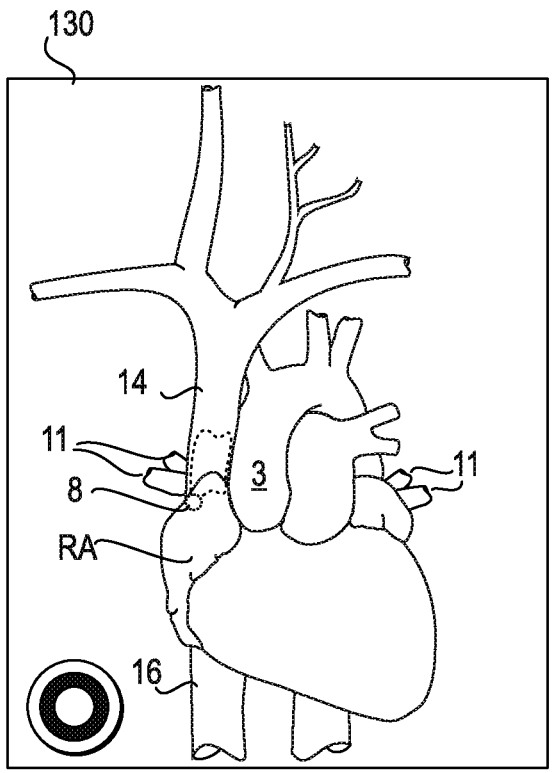
FIGS. 8A-8D illustrate a simplified user interface corresponding to the user interface of FIG. 7 and using blood flow information, optional intravascular ECG signals, and their correlation to display if the endovascular member is advancing towards the caval-atrial junction and sinoatrial node, if the endovascular member is advancing away from the caval-atrial junction and sinoatrial node, or if the endovascular member is at the caval-atrial junction proximal to the sinoatrial node.
Figure 8B:
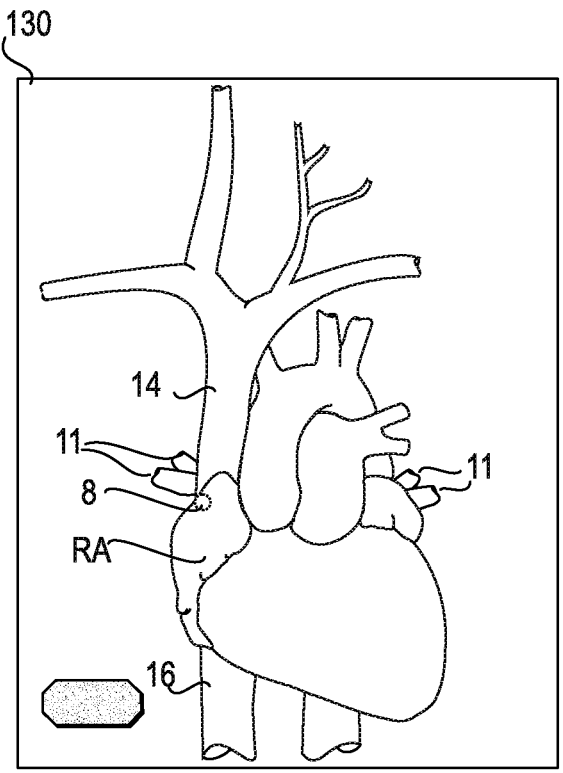
Figure 8C:
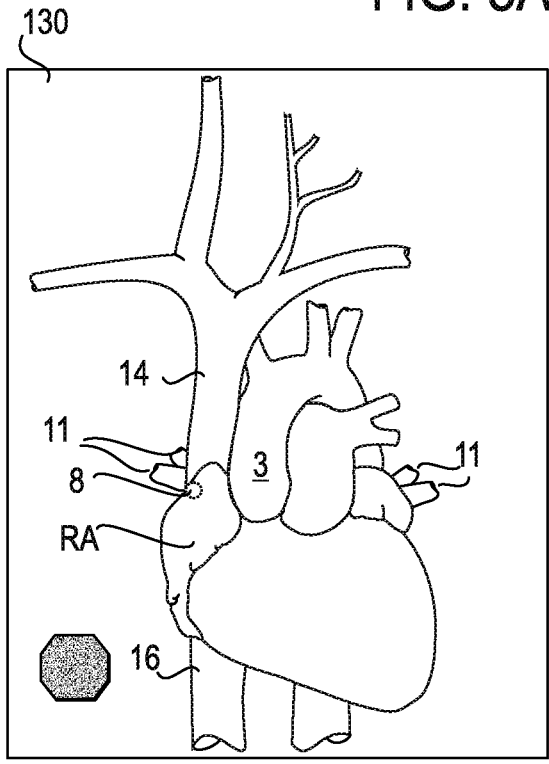
Figure 8D:
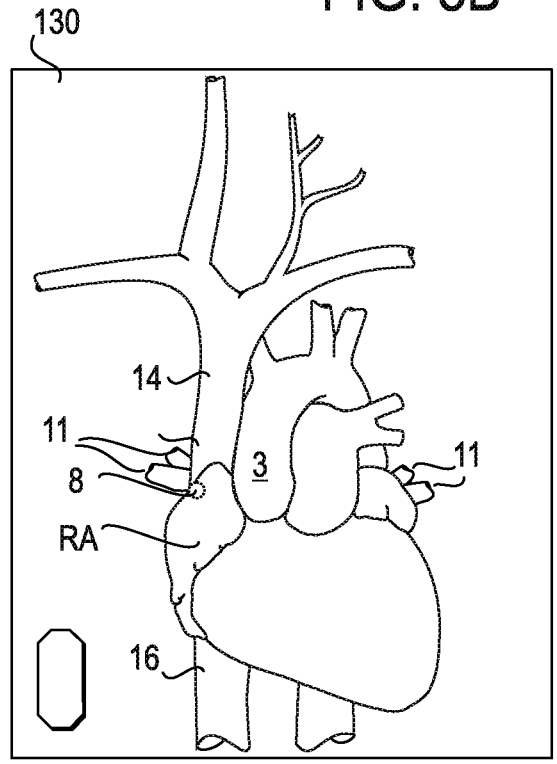

FIG. 2 also illustrates an exemplary endovascular device with an optional second endovascular electrocardiogram lead 135 on the elongate body 105. The second endovascular lead is shown in a position that, when the endovascular device 150 is in the vasculature, the second endovascular electrocardiogram lead 130 is in contact with blood. Endovascular leads 130 (and/or the corresponding electrical sensing segment or segments 135) may extend from the elongate body 105 as shown in FIGS. 2 and 3A or may be integral to or within the elongate body as shown in FIGS. 3B, 4A, 4B 5A, and 5B. In one embodiment, the electrical sensing segment 135 of the second endovascular electrocardiogram lead 130 (the proximal electrocardiogram lead 130 in FIGS. 2 and 4B) is positioned about 5 cm from the other endovascular electrocardiogram lead 130. Alternatively, electrical sensing segment 135 of the second endovascular electrocardiogram lead 130 is positioned about 5 cm from the elongate body distal end 115.

The present invention provides new methods, devices, and systems for intravascular guidance and placement of endovascular devices based on the recognition of patterns in the signals for different physiological parameters and correlation of those signal patterns. In one exemplary application, a catheter, such as a peripherally inserted central catheter (PICC) is inserted, advanced, positioned, and monitored within the vasculature based on the recognition of parameter information (e.g. blood flow patterns) and their correlation at the locations of interest. In various embodiments, the system optionally utilizes electrocardiogram signals with the above parameters.

Pre-Processing and Processing System

The present invention provides a new methods, devices and systems for intravascular guidance and placement of endovascular devices based on the recognition of patterns in the signals for different physiological parameters and correlation of those signal patterns to catheter tip locations. In addition or alternatively, neural network algorithms can be used for feature extraction, determining parameter values, and/or be used in scoring functions, as further described below.

FIG. 9 is an exemplary block diagram of at least a portion of a system in accordance with various aspects of the invention. In various respects, the system of FIG. 9 is similar to the system 100 of FIG. 1 and the same numbering will be used herein.

Various components of system 100 are similar to conventional ultrasound control systems. Examples of ultrasound control systems are described in the following patents: U.S. Pat. No. 6,896,658 to Ji et al. entitled "Simultaneous Multi-mode and Multi-band Ultrasonic Imaging"; U.S. Pat. No. 6,251,073 to Imran et al. entitled "Miniaturized Ultrasound Apparatus and Method"; U.S. Pat. No. 5,492,125 to Kim et al. entitled "Ultrasound Signal Processing Apparatus"; U.S. Pat. No. 6,561,979 to Wood et al. entitled "Medical Diagnostic Ultrasound System and Method"; and U.S. Pat. No. 5,477,858 to Norris et al. entitled "Ultrasound Blood Flow/Tissue Imaging System"; related to Doppler ultrasound U.S. Pat. No. 4,324,258 to Huebscher et al. entitled "Ultrasonic Doppler Flowmeters"; U.S. Pat. No. 4,143,650 to Hatke entitled "Directional Doppler Ultrasound Systems for Biosignal Acquisition and Method of Using the Same"; U.S. Pat. No. 5,891,036 to Izumi entitled "Ultrasonic Wave Doppler Diagnosing Apparatus"; related to guidance U.S. Pat. No. 5,220,924 to Frazin entitled "Doppler-Guided Retrograde Catheterization using Transducer Equipped Guide Wire"; U.S. Pat. No. 6,704,590 to Haldeman entitled "Doppler Guiding Catheter using Sensed Blood Turbulence Levels"; U.S. Pat. No. 5,311,871 to Yock entitled "Syringe with Ultrasound Emitting Transducer for Flow-directed Cannulation of Arteries and Veins"; U.S. Pat. No. 6,612,992 to Hossack et al. entitled "Medical Diagnostic Ultrasound Catheter and Method for Position Determination Related to Tracking Method"; U.S. Pat. No. 5,785,657 to Breyer et al. entitled "Blood Flow Measurement Device"; and related to pressure estimation U.S. Pat. No. 5,749,364 to Sliwa Jr. et al. entitled "Method and Apparatus for Mapping Pressure and Tissue Properties", the entire contents of which patents are hereby incorporated herein for all purposes.

The system 100 includes a pre-processor 139 and processor 140 configured to receive and process a signal from the non-imaging ultrasound transducer and a signal from the optional endovascular electrocardiogram lead. In the embodiment illustrated in FIGS. 6 and 9, the hardware and the software of the pre-processor are separate. The pre-processor software is implemented on the same device (e.g. a personal computer or microprocessor) as the processor software. The other pre-processing functions are handled by the hardware. The hardware may also include embedded software or firmware. In other embodiments, the preprocessor can be entirely software or entirely hardware.

Referring to FIG. 9, the system 100 includes a stylet-ECG interface 201 having one or more sensors. A programmable pulse sequence generator including a pulser 203, pulser drive 205, and pulser control 207 generates electronic signals, such as electronic pulses, that drive the ultrasound sensor. A transmit-receive switch 210 controls the interface and sends/receives signal data to and from the sensor. The transmission and reception functions are controlled by pulser 203, pulse drive 205, a field programmable gate array (FPGA) 213, and a digital signal processor 215. The exemplary signals are individually delayed depending on the mode of processing and other factors. In one example, the generated waveform for the sensors depends on the operating mode. A-scan, Doppler, etc. can be selected according to the desired mode. In an exemplary embodiment, an A-scan is generated about every 10 ms. In an exemplary embodiment, a sensor is driven with a Doppler pulse sequence fired at a frequency referred to as pulse repetition frequency (PRF). In various embodiments, the PRF is about 40 kHz. The system may make use of pulsed-wave (PW) or continuous-wave (CW) functions. Further information regarding parametric waveform generation and similar concepts are discussed in U.S. Pat. No. 6,896,658 to Ji et al for Simultaneous multi-mode and multi-band ultrasonic imaging and U.S. Pat. No. 6,551,244 to Gee for Parametric transmit waveform generator for medical ultrasound imaging system, the entire contents of which are incorporated herein for all purposes.

The transmit-receive switch 210 provides acquired data to the other components of the system. In an exemplary embodiment, the system includes a plurality of Doppler sensors and the transmit-receive switch includes a multiplexer to couple electrical signals from generator to each of the respective sensors (e.g. 120 in FIG. 2). The exemplary sensors generate a single divergent ultrasound beam by transforming the electrical energy into mechanical acoustic waves. The exemplary acoustic waves are between about 5 MHz and about 15 MHz.

The sensor receives a reflected signal (e.g. an echo) and transforms the high frequency ultrasound mechanical wave into corresponding electrical signals. These electrical signals are received through transmit-receive switch 210 and optionally multiplexed into the desired signal path. The exemplary digital signal processor receives the electrical signals and distributes them to the processing path.

In general, the pre-processor includes conventional processing capabilities to receive and process ultrasound as with conventional ultrasound signals. The conventional processing capabilities may include conventional components needed to receive, process, and store the corresponding sensor data such as analog-to-digital (A/D) conversion. In the system of FIG. 9, for example, the received signals are transferred from the interface 201 through the switch 210 to a Doppler gain 217, analog filter 219, and Doppler analog-to-digital converter (ADC) 220 where the signal is amplified, filtered, and digitized. The amplification of the signal is controlled by a programmable gain DAC/POT 222. The digital signal is then transmitted to a digital signal processing (DSP) chain on the FPGA 213. The exemplary system is a 16-bit data system and has an internal clock speed of 135 MHz.

If sensors on the elongate body are optionally used to further detect ECG activity, then appropriate electrocardiography components and processing capabilities are provided. The same is true for EEG signal processing, EMG signal processing, acoustic sensor processing, pressure sensor processing, optical sensor processing and the like. Referring to FIG. 9, a right shoulder 225 cooperates with an ECG lead 111. The ECG signal is amplified, filtered, and otherwise modified by various components including ECG gain 219 and ECG analog-to-digital converter 220. As is apparent from FIG. 9, the ECG signal processing is carried out by separate components than the Doppler signal processing.

System 100 further includes other features such as a computer processor 140 implementing the guidance and navigation processing techniques described herein and a digital-signal-processor 215 connected to a temperature sensor 227 for measuring and recording other system information.

Unlike conventional systems, pre-processor 139 and processor 140 include programming and processing capabilities to evaluate information from intravenous signals obtained from the sensors to provide specific results related to the guidance, positioning and confirmation of location as described herein. In general, the guidance system includes programming and capabilities of a pre-processor and processor adapted to extract information from the sensor signals based on desired parameters, evaluate the pre-processed information based on correlations and/or other information (e.g. knowledge of the phase of navigation), and determine a result related to the guidance, positioning and confirmation of location. Moreover, the system of the invention may be able to return a result based on in vivo non-image based ultrasound alone without the need for X-rays verification.

The exemplary device is enabled to transmit and receive signals to collect information for use in the navigation and placement process of the invention. In various embodiments, the device transmits a non-imaging ultrasound signal into the vasculature using a non-imaging ultrasound transducer on the endovascular device. The device receives a reflected ultrasound signal with the non-imaging ultrasound transducer.

In one aspect, the processor 140 is adapted and configured using software, firmware or other programming capabilities to receive and process physiological signals including, but not limited to, a venous blood flow direction, a venous blood flow velocity, a venous blood flow signature pattern, a pressure signature pattern, A-mode information, and a preferential non-random direction of flow, as well as the capability to pre-process these signals to provide parameter features as inputs to the processor. In various embodiments, the processor is optionally adapted and configured to further receive and process other signals such as an electrocardiogram signal, a P-wave pattern, a QRS-complex pattern, a T-wave pattern, an EEG signal, and an EMG signal. Further discussion of other signal information and parameters suitable for use with the system of the invention is provided below.

The exemplary processor provides an output related to the probable position of or guidance information relating to the device within the vasculature. The exemplary processor contains, for example, rules, functions, or relationships used to determine the probable location and/or movement of the device within the body. Various embodiments of the guidance system described herein apply mathematical analysis to the pre-processed inputs including, for example and without limitation, mathematical functions, moving windows, weights, adaptive weights, partitioning of a power spectrum, ratios of pre-processed inputs, iterations, updating of values, fuzzy logic, neural networks, membership functions, features, inference rules, output, and feedback, alone or in any combination.

In general, the processing of the signal information to provide a result to the output device generally includes the following operations. The first step is to extract information related to one or more desired parameters from the signal inputs (e.g. retrograde/antegrade power). Depending on the application, the information may be a numerical value derived from the Doppler signal and optional other signals (e.g. ECG signal).

Next, the processor receives the extracted information as inputs. In various embodiments, the processing of the input information involves determining its degree of membership, or membership value, to a set of predefined input membership functions or classes for catheter tip location (e.g. push the catheter in, stop and keep the current tip location, pull back the catheter, etc.). When features cannot be described as only a single membership function, a combined membership function may be introduced. Next, the processor evaluates membership values for the possible output membership functions. This may include, for example, applying a set of inference or IF-THEN rules in a fuzzy logic based algorithm, where if certain criteria are met, then a particular zone or state is indicated. Alternatively, a neural network based algorithm can be used, as described herein. Next, the processor calculates a score based on the membership functions and derives a definite result related to the tip location. In various aspects, weighting is used in the final processing of the various parameters to signify the relative impact of each and adapt the signal to the overall condition of the data set. In various respects, the processor output correlates to one of a number of predefined states. In some embodiments, a plurality of scores are generated or determined based on a plurality of features, where the higher the score, the higher the probability or likelihood of membership in a zone or state. In some embodiments, the highest score of the plurality of scores is used to determine the state or zone.

Finally, the processor output is translated into an indicator displayed on an output device. The indicator may be a unique light color, symbol, or other straightforward indication to a user.

With reference to FIGS. 1, 9, 10, and 11, the exemplary system 200 includes processing features corresponding to the sensors of the system. The exemplary processing circuitry includes circuitry 202 for processing an in vivo non-image ultrasound signal and an optional circuitry 202 for processing an exemplary ECG signal.

In the exemplary embodiment, the optional ECG signal is used as a confirmatory signal for the ultrasound signal processing. However, the guidance system and method disclosed may, and in many cases will, provide for sufficiently accurate guidance and positioning without use of a confirmation signal or other techniques for confirming position. Nonetheless, use of such other signals may be desirable for additional placement confidence, error reporting, or selective triggering of the data acquisition and processing mechanism among other reasons.

In various embodiments, the Doppler-based processing and positioning technique includes the following operations explained with reference to FIG. 11. First, convert incoming signals from a time domain to a frequency domain, as described in steps 1105, 1110, 1115 and 1120.

At step 1105, get sampled Doppler data, antegrade and retrograde flow.

Next, at step 1110, filter antegrade and retrograde flow using a band pass filter.

Next, at step 1115, in each data segment of antegrade and retrograde flow, apply Hamming window (e.g. Hanning, Rectangular, Gaussian, etc.).

Next, at step 1120, calculate frequency spectrum (e.g. Fast Fourier Transform, FFT) of each data segment.

Next, at step 1125, calculate power spectrum of antegrade and retrograde Doppler data. Numerous different features are possible. Exemplary Doppler features are further described, for example, in FIGS. 13, 14 and 15.

Figures 13, 14:
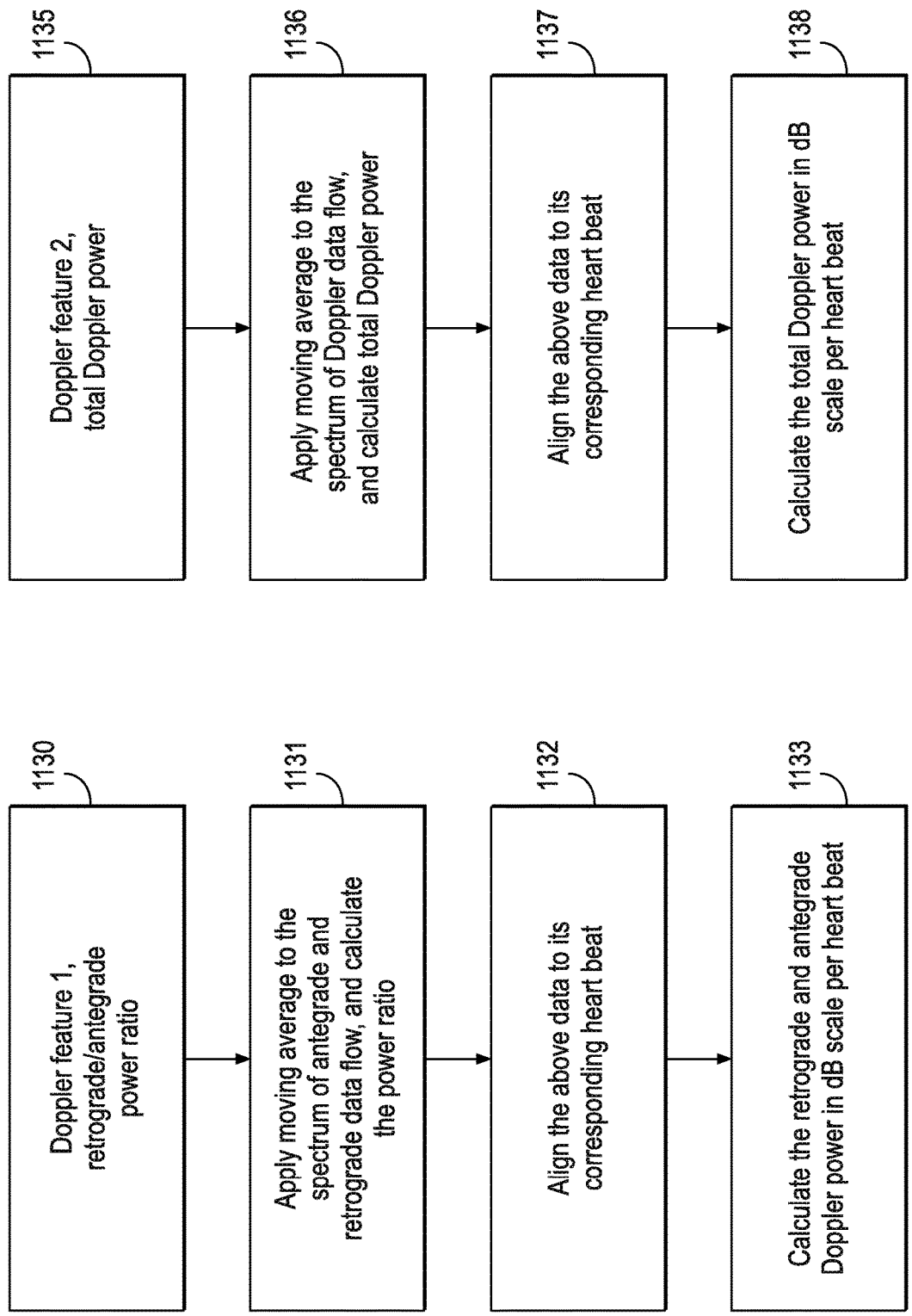
FIG. 13 is a flow chart of the pre-processing of signal data of FIG. 11 to obtain Doppler feature 1a (DF1a).
FIG. 14 is a flow chart of the pre-processing of signal data of FIG. 11 to obtain Doppler feature 2.
Figure 15:
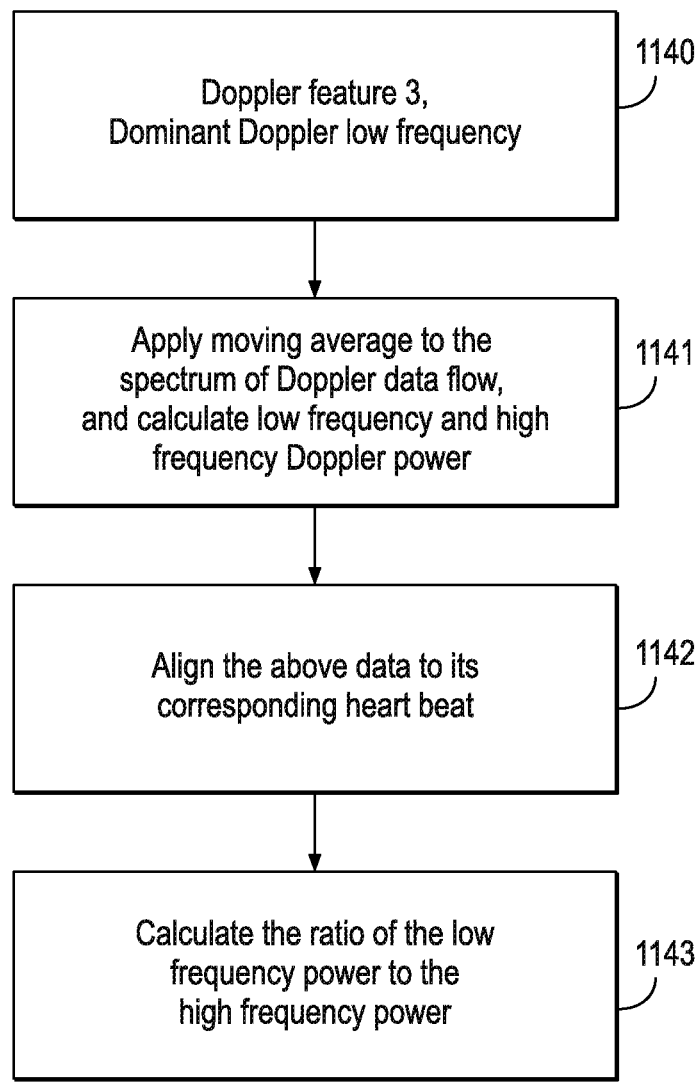
FIG. 15 is a flow chart of the pre-processing of signal data of FIG. 11 to obtain Doppler feature 3.

Next, extract features for use in processor functions. For Doppler Feature 1a (DF1a), for example in step 1130, calculate the ratio of retrograde/antegrade Doppler power in dB per heart beat, shown in FIG. 13. For Doppler Feature 2 (DF2), for example in step 1135, calculate total Doppler power, as shown in FIG. 14. For Doppler Feature 3 (DF3), for example in step 1140, calculate dominant Doppler low frequency power, as shown in FIG. 15.

Next, determine the output of each membership function using the inputted features, where the membership function provides information regarding the location of the catheter tip based on a particular feature or features. Here, a feature includes all Doppler, ECG or other feature used by the system.

Figure 16:
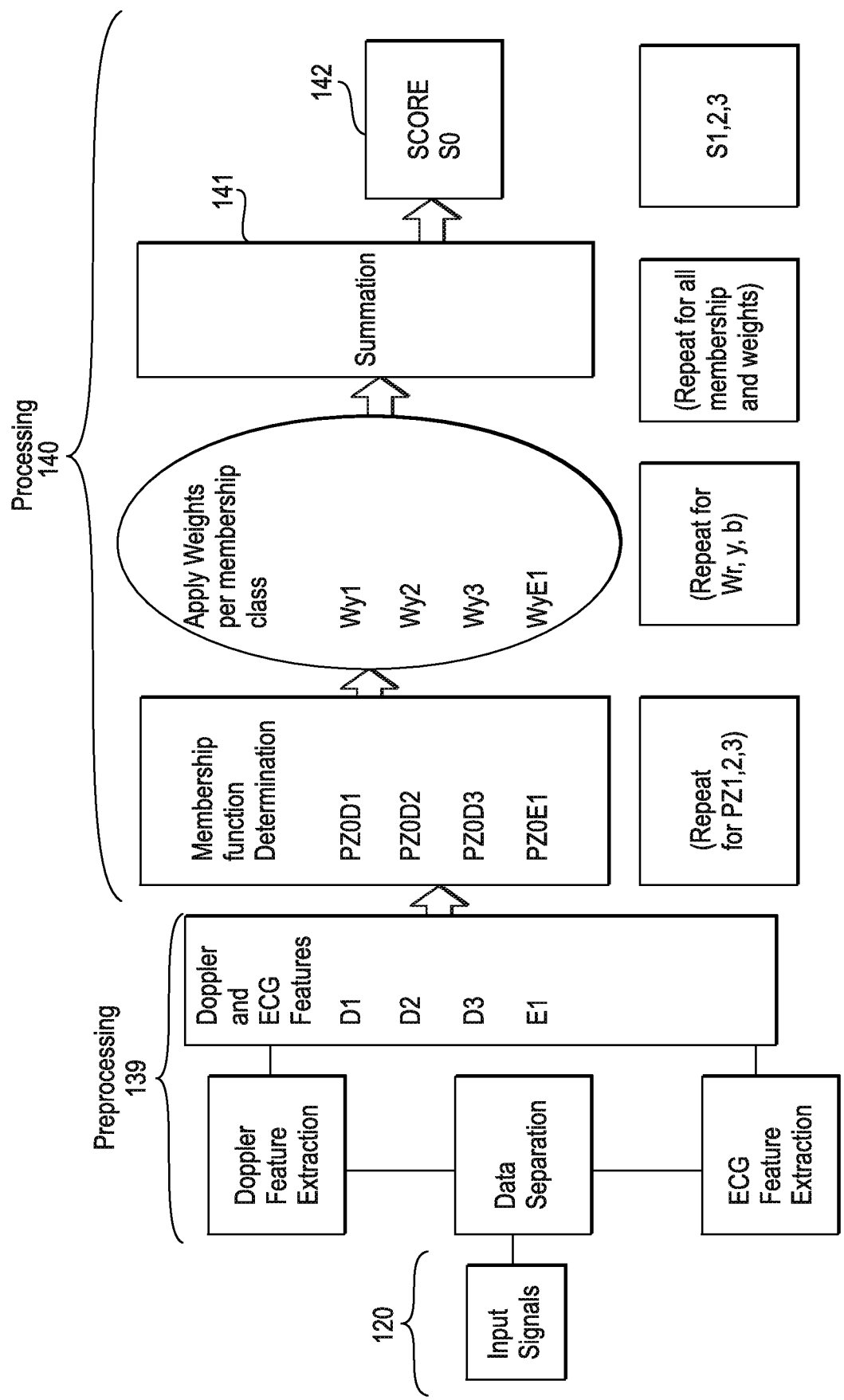
FIG. 16 is a block diagram of the system of FIG. 9, illustrating receiving information related to the pre-processed feature as inputs and providing a result based on membership functions.

Next, assign a weight to each feature based upon zone score to be calculated, shown in FIG. 16. In addition or alternatively, apply weights to membership function determinations per membership class.

Next, calculate a score for each zone based upon Doppler or ECG feature, membership function, weight, and summation, shown in FIG. 16.

Next, check if there are any exceptions. If so, select exception result.

If there are no exceptions, the zone with highest score calculation in each cycle determines which indicator to display, depending upon subsequent time average.

The overall operation of the system will now be described with reference to FIG. 16. FIG. 16 is a flow chart of the process flow used to input signals into a decision engine according to the methods and systems described herein. Based on the listing set out above, operations leading up to the calculation of probability of membership function are generally performed by a pre-processor, generally designated 139. Operations including and after the membership function determination step are generally performed by the exemplary processor 140. One will appreciate, however, that the pre-processor and processor of the invention may be modified depending on the application including adapting the components to perform more or less operations and combining all the operations into a single processing device.

In various embodiments, internal and external ECG signals are obtained and fed into the pre-processor. The optional ECG signal pre-processing may include a number of steps, such as:

1. Get a section of raw data from ECG signal train.
2. Detect QRS complex wave.
3. Detect the corresponding P wave.
4. Calculate the magnitude of P wave, P_mag, by peak detection.
5. Obtain the timing of each heart beat for Doppler (antegrade, retrograde) to align.
6. Calculate the P wave feature, pRatio, as follows:

Two P_mag: external P_mag and internal P_mag are calculated as above, and pRatio is calculated as follows: pRatio=(internal P_mag)/(external P_mag)

In general, the pRatio increases the catheter tip moves from the periphery and towards the heart. Therefore, as the catheter tip is navigated through the venous system, an increasing pRatio generally indicates that the catheter is moving towards the heart and is moving in the correct direction.

Since the P-wave in the internal ECG may elevate during the catheter insertion, the P-wave in the external ECG may optionally be used as a reference signal in the processing system. The reference value or a comparison to the reference value may be used as a feature as will be described below. In addition, detection of a P-wave with biphasic characteristics can trigger an internal software flag that may be used by the processor as a feature to determine the location status or zone of the catheter tip. For example, in some embodiments, detection of a biphasic P-wave can indicate that the tip of the catheter has passed the SA node and has entered the right atrium, which in some applications indicates that the catheter tip has been advanced too far and should be retracted. Whether the P-wave is biphasic or not is another P-wave feature.

By monitoring both the pRatio and whether the P-wave is biphasic or not, the catheter tip can be advanced towards the heart and towards the desired destination, while also detecting whether the catheter tip has been advanced past the destination.

Figure 10:
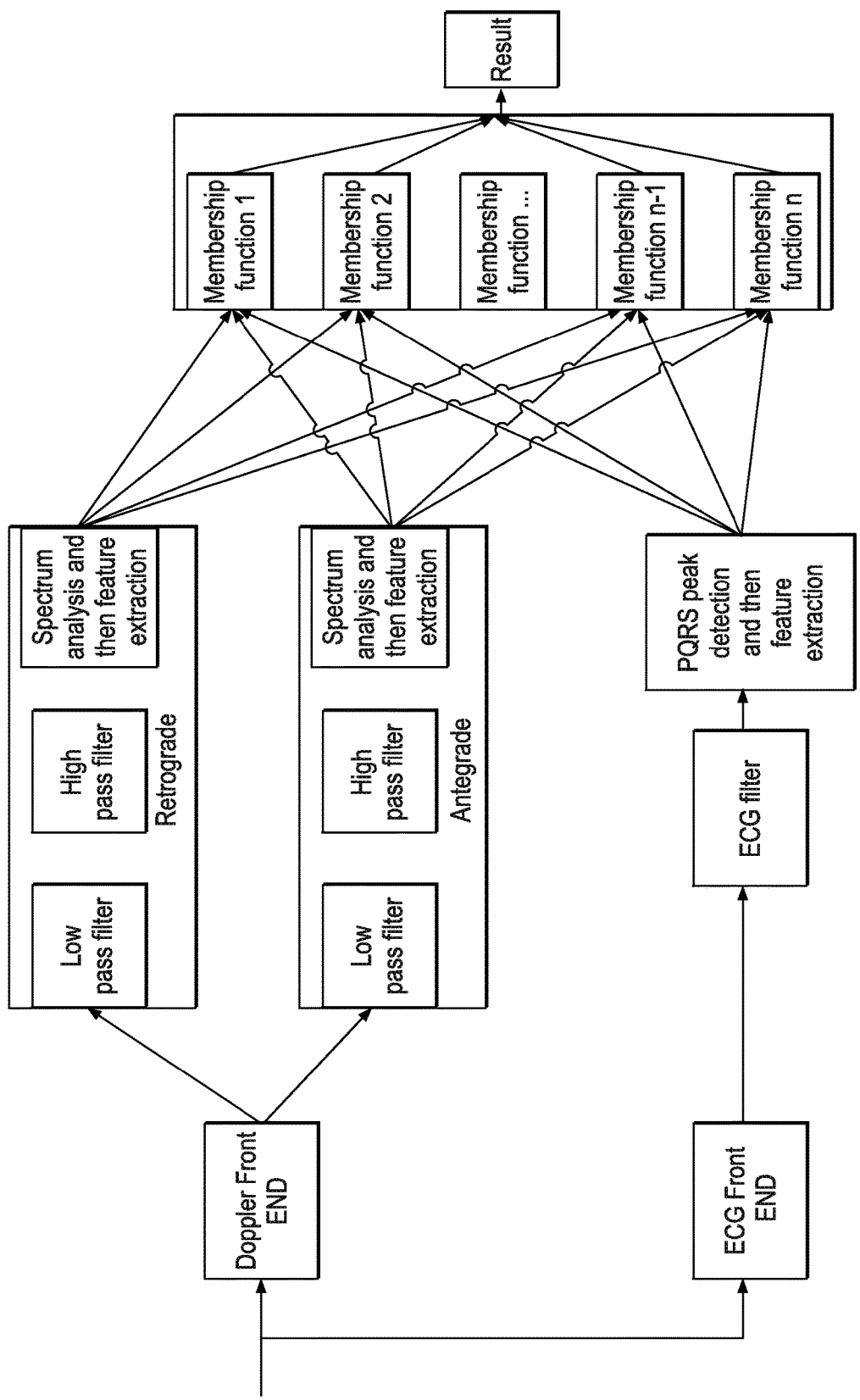
FIG. 10 is a block diagram representing the flow of data in the system of FIG. 9.
Figure 11:
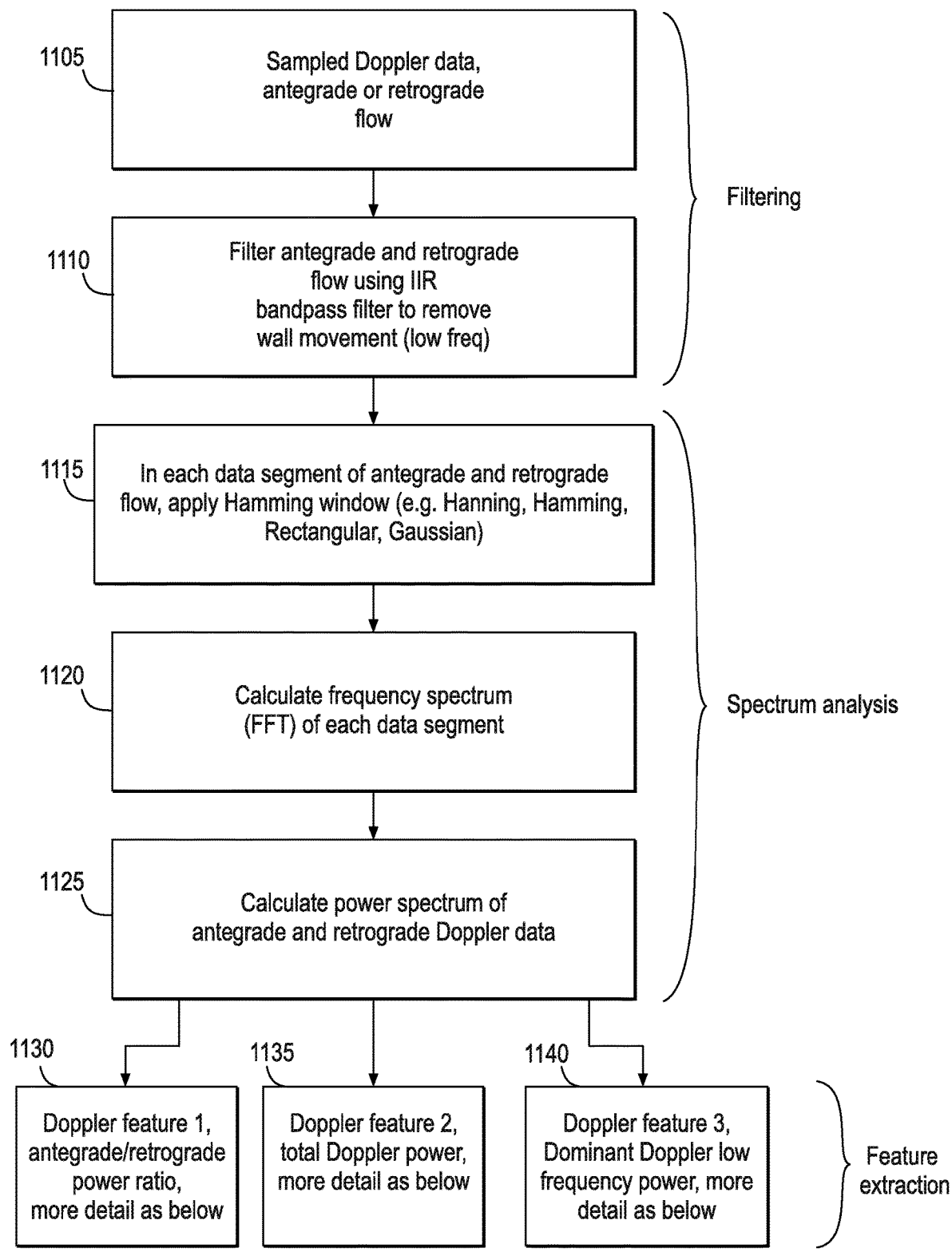
FIG. 11 is a flow chart of the pre-processing of signal data of FIG. 10 to obtain three Doppler features in accordance with the invention.

Turning to FIGS. 9, 10, and 11, the exemplary system receives sampled signal information from the one or more sensors as an input. FIG. 10 illustrates the general flow of data within the system circuitry of FIG. 9. FIG. 11 is a flow chart illustrating the flow of data for each data cycle.

The signal information from the sensors may consist of Doppler (ultrasound) signal, and optionally, other non-Doppler signals. In the exemplary embodiment, the system inputs include a Doppler signal, an intravascular ECG signal, and an extravascular ECG signal. The exemplary pre-processor algorithm includes sampling the Doppler signal at a desired frequency. In various embodiments, the frequency is between about 20 to about 50 KHz/channel. The resulting sampled data may be stored in a memory, which may be local or off-device.

The signal input (sampled data) is passed through a series of pre-processing functions to extract desired parameter information. In the illustrated example, when using optional ECG sensors, the signals are first separated between a Doppler processing path and an ECG processing path. Next, the Doppler signal and ECG signals are subjected to a number of processes to further extract desired parameter information.

In various respects, "parameter", "criterion", and "feature" are used somewhat interchangeably and refer to the desired information output by the pre-processor and utilized by the processor as discussed below. In various respects, "parameter" refers to the information after the extraction and optional mathematical operations are performed by the pre-processor.

The pre-processing generally includes separating desired parameters from the sampled data. In one example, the device extracts Doppler directional data (e.g. antegrade and retrograde or left and right channel). The data may be extracted at different memory locations if it is presented as a continuous incoming data stream from the sampler. In the illustrated example, each of the retrograde and antegrade signals are subjected to a low pass filter, high pass filter, and spectrum analysis to extract flow information in the retrograde and antegrade directions. The exemplary low pass filter removes noise associated with wall movement (low frequency). The high pass filter and spectrum analysis separate the power spectrum data as shown in FIG. 11. The data is further subjected to other operations such as Hamming, fitting (e.g. to a Gaussian curve), and Fast Fourier Transformation (FFT) to focus on a specific parameter or feature of interest.

The exemplary pre-processing identifies at least one desired parameter in the data stream. In an exemplary embodiment, the pre-processor outputs the following parameters to the processor: a ratio of the antegrade to retrograde flow, a difference between antegrade and retrograde flow velocity, Doppler signal total power, and a ratio of average low velocity power to high velocity power.

The exemplary pre-processor also performs numerical calculations on the extracted information before transmitting to the processor. The pre-processor operations may include adding, subtracting, combining (e.g. to provide a ratio), averaging, and more. As shown in FIG. 11 and further described in FIG. 13, for example, the pre-processor combines the extracted retrograde and antegrade power values to determine a ratio of retrograde/antegrade power corresponding to a desired "Doppler feature 1a." Similarly, other mathematical operations are performed to generate "Doppler feature 2" (the total Doppler power) as shown in FIG. 11 and further described in FIG. 14. Similarly, "Doppler feature 3" (dominant low frequency power) is shown in FIG. 11 and further described in FIG. 15.

Doppler Feature #1a: Ratio of Antegrade to Retrograde Doppler for both high frequency and low frequency components (DF1a). Doppler Feature #1a can be used to determine whether the catheter tip is being advanced in the right direction. In some embodiments, frequencies below 15000 Hz, 14000 Hz, 12000 Hz, 11000 Hz, 10000 Hz, 9000 Hz, 8000 Hz, 7000 Hz, 6000 Hz, 5000 Hz, 4500 Hz, 4000 Hz, 3500 Hz, 3000 Hz, 2500 Hz, 2000 Hz, 1500 Hz, 1000 Hz or 500 Hz can be used with this feature. In some embodiments, frequencies above 15000 Hz, 14000 Hz, 12000 Hz, 11000 Hz, 10000 Hz, 9000 Hz, 8000 Hz, 7000 Hz, 6000 Hz, 5000 Hz, 4500 Hz, 4000 Hz, 3500 Hz, 3000 Hz, 2500 Hz, 2000 Hz, 1500 Hz 1000 Hz, 500 Hz or 0 Hz can be used. In some embodiments, a frequency bandwidth between the high cutoff and the low cutoff can be used.

Doppler Feature #1b: Difference of Antegrade to Retrograde Doppler for a bandwidth of frequencies (DF1b). Doppler Feature #1b can be used to determine whether the catheter tip is being advanced in the right direction. In some embodiments, frequencies below 15000 Hz, 14000 Hz, 12000 Hz, 11000 Hz, 10000 Hz, 9000 Hz, 8000 Hz, 7000 Hz, 6000 Hz, 5000 Hz, 4500 Hz, 4000 Hz, 3500 Hz, 3000 Hz, 2500 Hz, 2000 Hz, 1500 Hz, 1000 Hz or 500 Hz can be used with this feature. In some embodiments, frequencies above 15000 Hz, 14000 Hz, 12000 Hz, 11000 Hz, 10000 Hz, 9000 Hz, 8000 Hz, 7000 Hz, 6000 Hz, 5000 Hz, 4500 Hz, 4000 Hz, 3500 Hz, 3000 Hz, 2500 Hz, 2000 Hz, 1500 Hz, 1000 Hz, 500 Hz or 0 Hz can be used. In some embodiments, a frequency bandwidth between the high cutoff and the low cutoff can be used.

Doppler Feature #2: Ratio of Total Doppler Power to noise floor estimate (DF2). The Total Doppler Power is related to the total blood flow. In some embodiments, frequencies below 20000 Hz, 19500 Hz, 19000 Hz, 18500 Hz, 18000 Hz, 17500 Hz, 17000 Hz, 16500 Hz, 16000 Hz, 15500 Hz, 15000 Hz, 14500 Hz, 14000 Hz, 13500 Hz, 13000 Hz, 12500 Hz, 12000 Hz, 11500 Hz, 11000 Hz, 10500 Hz or 10000 Hz, and above 0 Hz, 20 Hz, 40 Hz, 60 Hz, 80 Hz, 100 Hz, 120 Hz, 140 Hz, 160 Hz, 180 Hz, 200 Hz, 220 Hz, 240 Hz, 260 Hz, 280 Hz, 300 Hz, 320 Hz, 340 Hz, 360 Hz, 380 Hz, 400 Hz, 420 Hz, 440 Hz, 460 Hz, 480 Hz, 500 Hz, 600 Hz, 700 Hz, 800 Hz, 900 Hz or 1000 Hz can be used.

Doppler Feature #3: Ratio of low frequency power to low frequency plus high frequency power for both antegrade and retrograde Doppler (DF3). Doppler Feature #3 is related to the distance from the heart, and tends to decrease in value as the catheter tip approaches the heart. Frequencies and frequency bandwidths that can be used include low frequency bandwidths, mid frequency bandwidths and high frequency bandwidths as described above.

Doppler Feature #4: Difference of antegrade to retrograde Doppler for bandwidth of frequencies. Exemplary frequency bandwidths include for use with Doppler Feature #4 include the frequencies and frequency bandwidths as described above.

The frequency cutoffs are based on correlations with blood flow velocities. Low frequencies are associated with blood flow in the peripheral venous system, while high frequencies are associated with blood flow closer to the heart such as in the central venous system. In addition, where frequency bandwidths are used, a value or parameter can be averaged over the frequency range encompassed by the frequency bandwidth.

Additionally or alternatively, a feature may be based on a segment, a portion or a signal in an electrocardiogram. One such feature is pRatio. This feature is a ratio of internal ECG P wave to external P wave reference value. Another such feature is RS amplitude (see FIG. 12B). Still another feature is the QRS complex. Still another feature is T-wave amplitude.

With regard to step 1130 in FIG. 11 and reference to FIG. 13, exemplary Doppler feature 1 a represents retrograde/antegrade power ratio (step 1130). This feature is generated by calculating a moving average to the spectrum of antegrade and retrograde data previously extracted by the pre-processor (step 1131). The averaged value information is aligned with a respective heart beat (step 1132) as shown, for example, in FIG. 12A. Next in step 1133, the retrograde and antegrade power (dB) is calculated for the heart beat and combined into a ratio.

Doppler feature 1b (DF1b) is generated using the same values as Doppler feature 1a (DF1a). While DF1a is a ratio, DF1b is generated by taking a difference of the antegrade and retrograde data. Although the mathematical inputs are the same, the features are different.

With reference to FIG. 11 and in particular to FIG. 14, exemplary Doppler feature 2 (DF2) is used to represent total Doppler power (step 1135). This feature is generated by applying a moving average to the entire spectrum of flow data previously extracted by the pre-processor (step 1136). The averaged value information is aligned with a respective heart beat (step 1137) as shown, for example, in FIG. 12A. Next, the total power (dB) is determined for the heart beat (step 1138).

With reference to FIG. 11 and in particular to FIG. 15, exemplary Doppler feature 3 (DF3) is used to represent Dominant Doppler low frequency. This feature is generated by applying a moving average to the spectrum of data flow previously extracted by the pre-processor and calculating the low frequency power and high frequency power (step 1141). The calculated power values are aligned with a respective heart beat (step 1142) as shown, for example, in FIG. 12A. Next, the power values are combined into a ratio of low frequency power to low frequency plus high frequency power to determine the dominant low frequency power (step 1143).

In other aspects, one or more features may be combined in a different way or used as part of a different function or feature. In some embodiments, features can combine information related to multiple signal sources such as ECG, Doppler, and other sensors, such as oxygen saturation or carbon dioxide levels. In one specific aspect, one or more features may be combined or compared in order to determine a weight ratio. The weight ratio changes the importance of the Doppler signal compared the other inputted signals in the processor. In one exemplary embodiment, the weight ratio is a Doppler ECG CAJ weight ratio. This weight ratio is used to determine the significance of Doppler signal compared to ECG, in particular when the instrument is advancing within the vena cava approaching the caval-atrial junction. When the ratio is large, the processor places more emphasis on the information derived from the Doppler signal. When the ratio is low, the processor places more weight on the ECG signal features. The weighting ratio is determined at every time step since conditions may change which may affect the quality of the Doppler and ECG signals. In one exemplary embodiment, this ratio is based on Doppler Feature #2 and pRatio.

In various embodiments, the pre-processor extracts parameter information from additional non-Doppler sensors after separation from the Doppler signal. In an exemplary embodiment, the pre-processor processes an ECG signal. In an exemplary embodiment, the device includes internal and external sensors for providing an intravascular ECG signal and external (outside the body) ECG signal. The ECG signal is passed through an ECG front end, ECG filter, and PQRS peak detection element to extract information related to the PQRS peak. In an exemplary embodiment, the pre-processor outputs a correlation or ratio of the intravascular P-wave to the external P-wave as the desired ECG parameter. One will appreciate that other ECG-based features may be extracted from the ECG waveform. Examples of other features that may be extracted and used by the system include, but are not limited to, absolute peak values, average peak values, presence or absence of a peak, and time from peak-to-peak or beat-to-beat. For example, the system may extract information related to the RS peak, T-wave, S-wave, and more. The exemplary ECG parameter is output to the processor with the Doppler parameters above. In various embodiments, the features extracted from the non-Doppler signal are combined with the Doppler features as inputs in the pre-processing software.

One will appreciate from the description herein that the system may make use of signal s other than, or in lieu of, Doppler and ECG. For example, the system may make use of sensors and data related to respiration, oxygen saturation, and more. The data used by the system may be collected in real-time. The data may be acquired from memory or another source. For example, information can be collected, stored, and used later, such as by performing an assay and using information related to the assay later during navigation.

The software implementing the pre-processing techniques described can be applied in different ways. In various embodiments, the software controls are applied to the frequency domain after performing a Fast Fourier Transform (FFT) or in the time domain (no FFT). A typical number of points for the FFT are 512, 1024, 2048, and 4096. These numbers represent the length of a data vector. The signal can be averaged over time or over the number of samples both in time and frequency domains. The on-line averaging uses a filter window of variable length (e.g. between 3 and 25 samples) to average along a data vector. The multi-lines averaging computes the average of a selectable numbers of data vectors. The can spectral power can be computed in the frequency domain from the shape of the power spectrum for each of the considered signals (e.g. directional Doppler). In an exemplary embodiment, the spectral power of the directional Doppler spectra is used to differentiate between retrograde and antegrade blood flow.

Accordingly, the pre-processor receives signal information comprising information from a variety of sensors, extracts desired parameter information in successive steps, and optionally performs a number of calculations on the extracted information. The pre-processor receives the complex signal information and outputs discrete desired parameters, in the exemplary case, Doppler features 1a, 1b, 2, and 3 and an ECG feature. Thus, the signals are substantially transformed to obtain the desired parameter information. Nonetheless, the parameter information is generally representative of the sensor signal environment.

Unlike conventional systems that merely digitize a sensor signal of a single type (e.g. A/D conversion), one will appreciate from the description herein and the figures that the pre-processor of the invention performs a significant amount of processing on signal data to prepare the data for processing by the processor. The pre-processor of the invention can also receive as an input signal data consisting of a variety of types of signals such as Doppler, ECG, and more. The system of FIG. 9, for example, receives data from a Doppler sensor and ECG sensors and outputs information specifically related to antegrade power, retrograde power, total Doppler power, low frequency Doppler power, and ECG PQRS peak.

As discussed above, the pre-processing entails a number of separation and extraction operations. Although the parameter information output by the pre-processor reflects the signal input, and the sensor environment, the pre-processor outputs are directed to specific information of use by the interrelated processor. One will appreciate that the pre-processor may be configured in various manners depending on the application to receive, analyze, condition, and otherwise modify the incoming sensor data.

One will appreciate that the pre-processing may identify a variety of types of parameters. The pre-processing may extract single data points, data ranges or streams, and more. For example, the system may collect Doppler data over a segment of time, and the pre-processing may separate a segment of the Doppler data based on pattern recognition. The pre-processed parameters may be quantitative or qualitative, binary or fuzzy. More information regarding the parameters suitable for use with the device of the invention is provided below.

While described above with specific reference to Doppler and ECG, the techniques for navigation within the body are not so limited. The features used as part of a guidance system as well as the membership functions and adaptive weights applied to those functions may be altered to provide guidance to other parts of the anatomy or utilize other inputs/signals to determine location and/or position. Other signals naturally generated by the body such as electrical or acoustic signals, for example, may be utilized as part of a membership function. Additionally or alternatively, artificial signals (i.e. not generated by or within the body) may be introduced into, on, or about a region or location of the body and then utilized as part of a membership function. In still other alternatives, other instrumentation may be added to the catheter described herein, or separate devices or instruments may be utilized to provide membership function information in addition to Doppler. Other devices or capabilities include, but are not limited to, other ultrasound modes, encoded signals, acoustic signals, magnetic signatures, and the like. These signals and devices may be introduced into the body, detected, and then utilized in a membership function.

With continued reference to FIGS. 9, 10, and 11, the system 200 includes a processor for receiving the parameter information from the pre-processor as inputs. The processor is adapted and configured to process the input information and output a result related to the position, movement, or confirmation of location of the sensor in the vasculature.

Both the exemplary pre-processor and processor within the system may be adapted and configured with software, firmware, or other programming capabilities to receive and process the features as described.

In contrast to the pre-processor, the processor generally conducts higher-level, more sophisticated processing of the respective data. In part, the processor implements algorithms and makes decisions whereas the pre-processor generally extracts embedded information and performs basic mathematical operations.

In various embodiments, the positioning method includes comparing the parameters to another value. In an exemplary embodiment, the processor compares the flow energy directed away from the endovascular device to the flow energy directed towards the endovascular device. In one aspect, the system selects for comparison the flow energy related to blood flow within the range of about 2 cm/sec to about 25 cm/sec.

In various embodiments, the positioning method includes processing the reflected ultrasound signal to detect indicia of pulsatile flow in the flow pattern. The indicia of pulsatile flow may be any of a number of different parameters. The indicia of pulsatile flow may be: a venous flow pattern, an arterial flow pattern, an atrial function of the heart, and the like.

In various embodiments, the pre-processor makes use of decision processing. In various embodiments, the pre-processor separates a desired parameter from the signal data, makes a comparison, and then decides whether to store information related to the parameter for use based on the comparison.

In various embodiments, the pre-processor and/or processor include filters. Selective filtering of certain frequencies may be used to remove undesired artifacts and frequency components, e.g., high frequencies indicative of a high degree of turbulence. Selective filtering also may be used to emphasize certain frequencies as being more important in the decision making process. For example, the lowest and the highest relevant frequency of the spectrum (i.e. the lowest and the highest relevant detected blood velocity) can be associated with certain location in the vasculature and in the blood stream.

One will appreciate from the description herein that the device in accordance with the invention may be modified to perform the pre-processing and processing functions within different structures. For example, some of the pre-processing may be performed on-board a sensor. Some or all of the pre-processing may be integrated into the processor or provided as a separate unit. In addition, the order of the operations may vary depending on the application.

The processor may be configured to process the parameter inputs by adapting processing techniques understood by one of skill in the art from the description herein. In various embodiments, the processor utilizes artificial intelligence programming. Examples of artificial intelligence programming that can make use of the principles described herein include, but are not limited to, logic such as first order logic (e.g. fuzzy logic) and proposition logic, an expert system, a neural network, and an inference engine.

With continued reference to FIGS. 9 and 10, the processing platform 4 can be a generic one like a personal computer or a dedicated one containing digital signal processors (DSP). The computing platform serves two purposes. It provides the processing capabilities of the pre-processor 139 and processor 140, which allows data processing algorithms to run. The various data processing algorithms employed by the various methods of embodiments of the current invention are described in greater detail below. The other purpose of the computing platform is to provide "back-end" functionality to the system 100 including a graphical user interface, data storage, archiving and retrieval, and interfaces to other systems, e.g., printers, optional monitors, loudspeakers, networks, etc. Such interfaces can be connected in a wired or wireless configuration. Those of ordinary skill will appreciate that the conventional components, their configurations, their interoperability and their functionality may be modified to provide the signal processing and data capabilities of the guidance system 100.

Guidance and Positioning Principles

While desiring not to be bound by theory, certain aspects of the invention operate based on the principle that certain locations in the vasculature can be identified by specific blood flow parameters and correlation between these blood flow patterns at those locations. These patterns may be based on, for example, Doppler blood flow measurements. This information may be supplemented and/or confirmed based on parameters related to other sources such as an intravascular and/or extravascular electrocardiogram and blood pressure. Moreover, the direction of travel for a sensor-equipped endovascular device relative to the direction of blood flow can be derived from Doppler information. In various respects the methods and systems for intravascular guidance and placement are based on the recognition of patterns in the signals for different physiological parameters and correlation of those signal patterns.

Signals or information based on one or more of the above may be used by the pre-processor and input to the processor described herein to accurately determine a position. Alternatively, one or more principles and rules used by the processor system may be based on one or more of the above.

In various aspects of the invention, the system processes position and/or direction information in real-time using the sensors, techniques, data acquisition, and processing described herein. In the case of a Peripheral Inserted Central Catheter (PICC) line, a user receives real-time, constant feedback on advancing a guided vascular access device to allow the PICC to advance along a desired path from an insertion vein into the vena cava and towards the sinoatrial node. The system recognizes unintended entry into other veins based on the differences in flow patterns or other parameters extracted from the intravascularly placed sensor signals. As such, the system may recognize unintended entry into the right atrium, inferior vena cava, jugular vein, the subclavian vein. Additionally, the system may detect when a sensor is against the vessel wall. By monitoring and processing the data acquired from sensors positioned on the endovascular access device, the user can be notified when the device tip reaches the ideal placement in the lower third of the superior vena cava, at the caval-atrial junction (CAJ) and/or in the proximity of the sinoatrial node. The system recognizes these locations of the vena cava, and other vascular components, by analyzing sensor-acquired data to identify unique flow patterns in order to confirm placement, location and/or guidance.

In various embodiments, the sensor technology described herein is only a non-imaging ultrasound. The unique flow patterns may be discerned using non-imaging ultrasound and as such does not require all the elements that make ultrasound imaging possible, such as scanning with a moving transducer, working with phased arrays and beam forming, and the like. As such, embodiments of the present invention provide a vascular access and guidance system with a hand-held, simple, inexpensive user interface. Non-imaging ultrasound includes a number of various ultrasound techniques and processing configurations, by way of non-limiting example: A-beam ultrasound, Doppler ultrasound, continuous wave Doppler ultrasound, pulsed Doppler ultrasound, color Doppler ultrasound, power Doppler ultrasound, bi-directional Doppler ultrasound, and ultrasound techniques that provide for the determination of velocity profile based on correlation of blood flow and time.

The physiological information is analyzed in order to identify the location in the vasculature where the information was acquired. Because body functions are unique at certain corresponding unique locations in the vasculature, embodiments of the present invention can use measurements of the body functions and detect location in the body.

Figure 20:
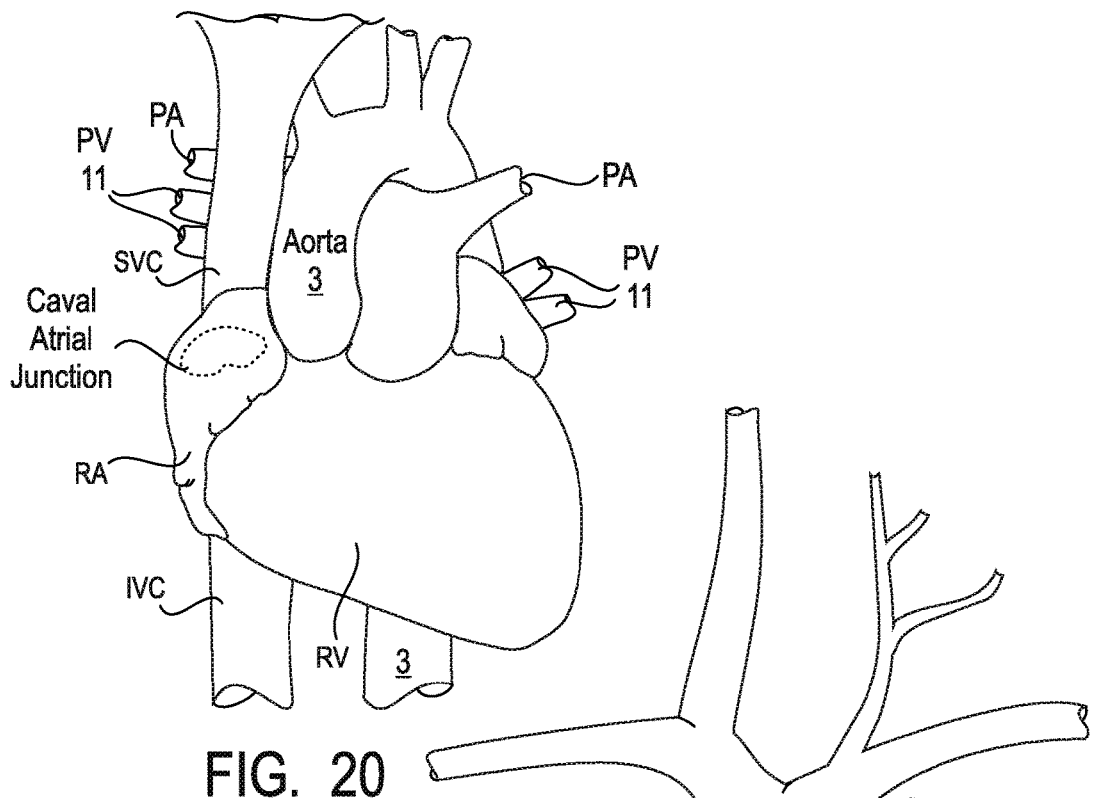
FIGS. 20 and 21 are various views of the heart and surrounding vasculature.
Figure 21:
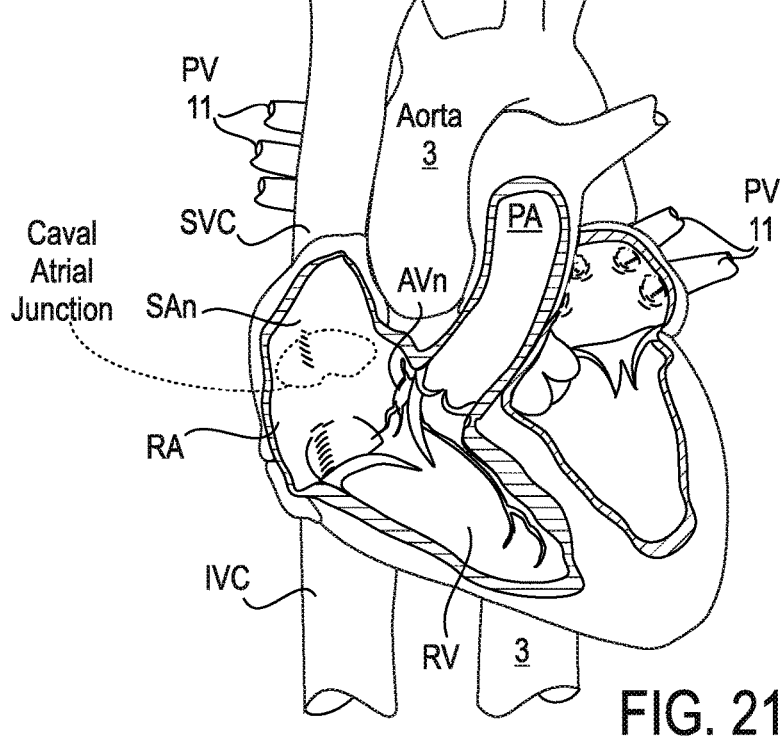

In various embodiments, the present invention relates to the use of the blood flow profile to detect the proximity of the sinoatrial node and of the caval-atrial junction. FIG. 20 illustrates the anatomical location of the caval-atrial junction at the confluence between the superior vena cava (SVC) and inferior vena cava (IVC) just before entering the right atrium (RA). FIG. 21 illustrates the anatomical location of the sinoatrial node at the caval-atrial junction (CAJ). The function of the vasculature and the function of the heart are unique at the caval-atrial junction both in terms of blood flow profile and of electrical activity of the heart.

In various embodiments, the methods, devices and systems described herein use a "multi-vector" or "multi-parameter" approach. Multi-vector approach refers to the use of multiple parameters such as the blood flow information, the electrical activity information, and the relationship between the two.

In various embodiments, the system is a multi-parameter system that uses intravascular electrocardiograms or other physiological or non-physiological sensor data in combination with the ultrasound signal. In various embodiments, the system according to the present invention identifies the blood flow profile characteristic of the caval-atrial junction and optionally identifies ECG waveform patterns characteristic of the proximity of the sinoatrial node. When both these patterns are present, the system indicates to the user that the desired target location has been reached. One benefit of this approach is that the location is accurate without the need for ECG signals and other methods. Another benefit of the exemplary approach using ECG as an optional confirmatory signal is that the blood flow and the electrical activity are independent physiological parameters and thus, by considering them together, the accuracy of the location information is further improved over any system dependent on ECG signals alone.

With particular reference to FIGS. 9, 10, and 16, the operation of the processor 140 will now be described in greater detail. As shown in FIG. 10, the processor receives the pre-processor outputs, processes the data, and provides a result 250 related to navigation and guidance of the sensor. The exemplary processor 140 sorts the parameter information from the pre-processor into membership functions.

As discussed above, the pre-processor 139 extracts and translates sensor signals into processing parameters. The processing parameters (variables) output by the illustrated pre-processor are shown in Table 1 below.

TABLE 1

Processing Variables

| Feature | Parameter/Variable |
|---|---|
| Doppler 1a (DF1a) | Ratio: antegrade flow to retrograde flow |
| Doppler 1b (DF1b) | Antegrade flow minus retrograde flow |
| Doppler 2 (DF2) | Doppler Signal Total Power |
| Doppler 3 (DF3) | Ratio: Low Velocity power to (low frequency power plus high frequency power) |
| ECG 1 (E1) | Ratio: P wave intravascular to P wave external |

The first four parameters—DF1a, DF1b, DF2, and DF3—relate to a Doppler signal. The processor also optionally receives a non-Doppler signal, E1. In one aspect, the non-Doppler signal is based on one or more portions of an electrocardiogram signal as described herein. The variables are generated by the pre-processor as explained above. The methods of extracting the parameters from the sensor signal are described above with respect to FIGS. 13-15.

The non-Doppler signal may be used for several purposes. For example, the non-Doppler signal can be used to align the Doppler parameters and/or sampling with physiological events (e.g. a heartbeat, inhalation of the lungs, or a nerve signal).

In various embodiments, the processing is carried out by recognizing flow patterns and/or signatures in the blood flow. In various embodiments, the processor compares a respective processor input (pre-processor output) to a calculated or expected value. In various embodiments, the processor compares a respective processor input to values in a look-up table. The use of a look-up table provides the advantage of reducing the number and complexity of processing operations that must be performed. In various embodiments, the processing makes use of thresholds. For example, an increase of a feature value above a threshold may indicate the catheter tip is in a specific zone or location.

The processor may make use of a computer platform programmed with software or embedded with code to perform the processing functions described herein. In various embodiments, the system utilizes standard intravascular system components and a computer program product for performing instructions related to the functions described herein.

In the exemplary case, the software is based on artificial intelligence. In various embodiments, the processor operates based on fuzzy logic. The principles and techniques for utilizing fuzzy logic systems are described in the following: European Patent Application No. 97830611.6 filed on Nov. 18, 1997 entitled "FUZZY LOGIC METHOD FOR AN INDIRECT MEASURE OF A PHYSICAL SIGNAL TO BE MONITORED, AND CORRESPONDING MEASURING DEVICE" with Publication No. EP 0917069; application Ser. No. 08/938,480 filed on Sep. 30, 1997 entitled "FUZZY LOGIC TISSUE FLOW DETERMINATION SYSTEM" granted as U.S. Pat. No. 5,857,973; Application No. PCT/US01/09115 filed on Mar. 22, 2001 entitled "METHOD AND APPARATUS FOR ASSESSING HEMODYNAMIC PARAMETERS AND BLOOD VESSEL LOCATION WITHIN THE CIRCULATORY SYSTEM OF A LIVING SUBJECT" with International Publication No. WO 01/70303; application Ser. No. 10/961,709 filed on Oct. 7, 2004 entitled "ULTRASOUND IMAGING SYSTEM PARAMETER OPTIMIZATION VIA FUZZY LOGIC with U.S. Patent Application Publication No. 2006/0079778; and application Ser. No. 10/329,129 filed on Dec. 24, 2002 entitled "METHOD AND APPARATUS FOR WAVEFORM ASSESSMENT" granted as U.S. Pat. No. 7,043,293, each of which is incorporated by reference in its entirety.

Time Intervals and Selective Acquisition and Processing

Time underlies much of the data acquisition and processing method described herein. For example, the time of acquisition, sampling frequency and PRF, and other time factors play roles in the described positioning method.

Figure 12A:
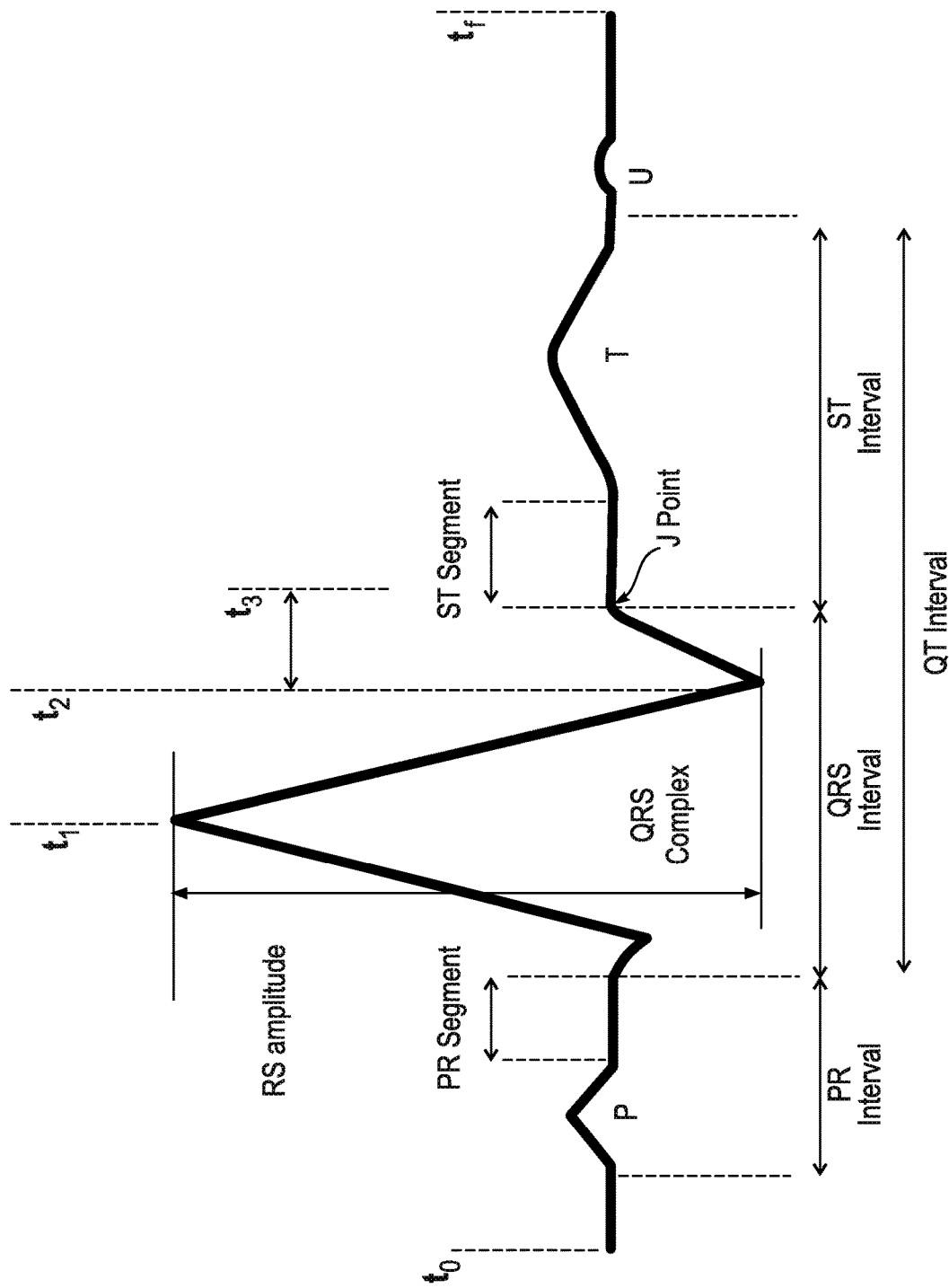
FIG. 12A illustrates an intravascular ECG signal used to correlate gating of the acquisition or processing of the blood flow information of FIG. 11 to the heart function.

In various embodiments, increasing sampling frequency (i.e. PRF) may increase resolution of the system. With reference to FIG. 12A, increasing the sampling frequency may increase the number of data points for each processing cycle between a start time, t0, and stop time, tf.

In various embodiments, the position and guidance of the sensor is broken into discrete movement increments and the sampling frequency is faster than the sensor is expected to move. Put another way, the sampling frequency may be tied to other factors than mere movement of the sensor such as the heart rate, breathing rate, and more. As the sensor moves from a location S0 to location S1, the processing system receives more than one data set. In other cases, signal data from more than one period or point of time may be bundled together.

Additionally, by analyzing the behavior of a parameter over a period of time, the system can realize several advantageous features. FIG. 12A illustrates an exemplary period of time selected by the system for analysis, which will generally be referred to here as the "processing window." The window starts at time t0 and ends at time tf.

In various embodiments, the processing windows for all or a portion of the positioning procedure are of substantially uniform length in the time domain. In various embodiments, the processing windows are shorter for increased granularity in one region than another. For example, it may be desirable to sample data faster and increase the rate of positioning analyses as the sensor approaches a desired or undesired destination. By segmenting the signal data and modifying the frequency and length of the segments, the speed and performance of the system may also be improved or adjusted. In various embodiments, the system recognizes when the signal data in one block of time is substantially similar to another and either bypasses the processing operation or deletes the subsequent block as being redundant.

Signal pre-processing and processing functions on any or all of the collected signals can be performed over time intervals. In one specific example where the signals are derived from ECG and Doppler signals, one or more time intervals could be selected to include correlation between the ECG and Doppler signals within a sub-interval of a heartbeat (shown, e.g., in FIG. 12A). Exemplary waves, points, intervals and subintervals for the heart rhythm that may be used for correlation measurements, pre-processing or processing functions include, for example, (a) any of the various waves or portions thereof such as P-wave, Q-wave, R-wave, S-wave, T-wave, or U-wave; (b) any of the various segments or portions thereof including the PR segment or ST segment; (c) any of the various intervals or portions thereof including the PR interval, the QRS interval, the QT interval, the ST interval; (d) the amplitude of any portion of the ECG waveform such as the P-wave amplitude, RS amplitude, T-wave amplitude; and (e) the use of the overall shape, amplitude or variation in a portion or sub-portion of the signal such as the QRS complex, the J point or any other inflection point in the electrocardiogram, Features that may be obtained from pre-processing operations include energy and waveforms of the ECG signals such as QRS complex ratios and antegrade and retrograde blood flow velocity signals. Features provided by collected signal pre-processing over the same time interval or at different time intervals (i.e. in synchrony with a specific portion of the QRS complex, respiratory cycle or other timing sequence imposed on the data collection and pre-processing activities) are utilized in membership functions and other aspects of the processing described herein. These optional features include, but are not limited to, ECG signal waveform, amplitude, position or other information related to the P-wave, QRS complex and the T-wave.

FIG. 12A illustrates a standard ECG wave. The ECG can be broken down into three primary components: the P-wave, QRS complex, and T-wave. These different components along with numerous other segments and values are indicated on FIG. 12A. Each of the different waves corresponds to different electrical activities of a normal heart. The P-wave may be of interest because it corresponds to atrial depolarization. As is understood in the art, the P-wave becomes distorted during atrial fibrillation. As the above illustrates, even in the case of patients with atrial fibrillation, the atrial electrical activity, which may not be seen on the regular skin ECG, becomes visible and relevant as the intravascular ECG sensor approaches the caval-atrial junction. Both the amplitude of the atrial electrical activity and its relative amplitude versus the QRS and R-waves change visibly at the caval-atrial junction in the close proximity of the sino-atrial node.

In addition to P-wave changes, various other portions of the QRS complex may be used with the positioning techniques described herein. For example, the amplitude of one or more segments may be compared to any portion of or all of an external ECG signal, an internal ECG signal or a reference ECG signal. In another alternative aspect, an ECG signal may be compared beat-to-beat or compared against earlier obtained ECG data. In one specific aspect, the amplitude of a portion or a segment of the electrocardiogram is used in the positioning process. In one alternative embodiment, the relative amplitude of a portion of the QRS complex is used. In one specific embodiment illustrated in FIG. 12B, the amplitude of the RS signal is used. FIG. 12B illustrates an exemplary ECG waveform from the brachial area (left side of the figure) and from the caval-atrial junction or CAJ area (right hand side of the figure). In this illustrative embodiment, the RS amplitude is compared against prior measured RS amplitude. FIG. 12B illustrates how the overall RS amplitude increases when advancing towards the CAJ from the brachial area. This information may be used in conjunction with positioning techniques described herein. For example, when a comparison of prior RS amplitude signals reveals that the amplitude has increased and remained consistently increased, then the processing algorithm may use that information as an additional factor for determining position of the instrument.

FIG. 12B illustrates one exemplary use of changes in amplitude of a portion of the electrocardiogram signal. Other portions of the electrocardiogram signal may also be used in a similar fashion depending upon the particular patient circumstances. Consider for example the case of a patient experiencing an irregular heart rhythm during a catheter placement procedure. In that event, the processing system may stop using one portion of the electrocardiogram made unreliable by the irregular rhythm and instead analyze a different portion of the electrocardiogram signal that is believed reliable. In addition or alternatively, the system may alter the weighting factor applied to those portions of the processing system that relies on the electrocardiogram information. By adjusting the weighting factor of the now unreliable ECG information, the processing system adapts to the reliability of ECG information.

In various embodiments, one or more parameters may be related to or aligned with Doppler signal information at a specific moment in the heart cycle. A parameter or feature that is aligned includes an average value, a summation, a truth value (e.g. has it passed a threshold value), a maximum value or a minimum value, and the like. As shown in FIG. 12A, for example, the data point or data period for the parameters may be selected based on the desired physiological event, in this case the heart pumping. This alignment may also occur by selecting the same portion of the electrocardiogram cycle for successive heartbeats. The portion of the electrocardiogram used to correlate the various signals used by the system during either or both of pre-processing and position calculations may be any of those electrocardiogram signal indications (i.e., waves, segments, intervals, points or portions) illustrated or described herein or with respect to FIGS. 12A and 12B. By example in reference to FIG. 12A, one feature may incorporate parameters obtained during times t1 (i.e., R-wave peak), t2 (i.e., S-wave peak), or both. In one specific example, Doppler feature 3 may incorporate a parameter analyzed over a period t3 (i.e., a time period corresponding to the interval from the S-wave to the J point). In the case of t3, another Doppler feature may be an average value, a summation, a truth value (e.g. has it passed a threshold value), a maximum or minimum, and the like.

Each of the exemplary features DF1 (DF1a or DF1b), DF2, and DF3 are used in combination in the analysis cycle shown in FIG. 11. When the sensor moves and/or new sample data is acquired, the cycle repeats and new DF1, DF2, and DF3 values are acquired. One will appreciate, however, that in the next cycle DF1, DF2, and DF3 will likely be acquired at slightly different times between t0 and tf and relative to each other. Alternatively, one or more of the features may be acquired at set times relative to t0, tf, or other indicia.

One will appreciate that, the feature values likely will vary when shifted to different times within a single processing window (in this example corresponding to the ECG waveform). As will be understood from the description herein, the feature values may be aligned with specific events. As described herein, features and parameters can be combined in a function or algorithm that relates the features to the parameters in order to determine a score that indicates positional information regarding the catheter tip.

In various embodiments, the properties of the ultrasound beam generated by the sensor are modified with respect to time. For example, it may be desirable to modify the operating frequency and/or the pulse repetition frequency to sample different target volumes or at different depths of penetration. The volume of the target of interest is defined as the three-dimensional region encompassed by the beam geometry and contained in the acquisition (processing) window. In various embodiments, the operating frequency is about 10 MHz to allow for a maximum penetration depth of about 20 mm. In various embodiments, the pulse repetition frequency (PRF) is about 40 kHz to allow the ultrasound wave to penetrate to a sufficient depth between pulses.

The modification of the processing based on the time function may be used to realize several unexpected advantages. For example, the period of time for inspection can be used as a quasi-filter by narrowing the analysis window to exclude undesirable data.

Aspects of the systems and methods described herein enable vascular navigation and device positioning in patients having irregular heartbeats such as arrhythmia including, for example, atrial fibrillation. If an irregular heart rate is detected or indicated, the processing system may apply a weighting function to a period of time over a specific portion of the ECG signal (e.g. the P-wave) during the signal processing and/or pre-processing. As a result, the feature produced from an irregular ECG signal may be weighted to reduce reliance on the ECG signal if the irregular aspect of the heart beat renders it unusable. If the irregular aspect of the heart beat, however, only renders a portion of the ECG signal unreliable, then the pre-processing may then be used to filter out the unreliable portion of the ECG signal. Alternatively, the irregular aspect of the heart beat may simply cause a different aspect of the ECG signal to be used based on the type of irregularity presented by the patient. Thus, in a patient suffering from arrhythmia, a ECG signal value may be different from a "normal" patient but still usable in the arrhythmic patient. As such, the signal collection and pre-processing features may be adjusted to utilize different portions of the ECG signal based on the type of arrhythmia.

Any of a wide variety of physiological characteristics of the body may be collected, pre-processed and then used with the pre-processor and processor to determine the location of the device within the body. Physiological characteristics often change depending upon location, relative movement, or proximity to structures within the body.

The signals used in the system described herein may be naturally produced by body functions, such as from electrical signals of the body like ECG, EMG or EEG. In addition or alternatively, the signal may be the result of an interaction with the body from an artificial signal or source introduced into a portion of the body. Such artificial signals include those generated through use of ultrasound, magnetic, or electric fields (e.g. through contact with the body with a probe, electrode or instrument in order to produce a signal or input at a specific, predetermined location in the body).

In various embodiments, one or both of the pre-processor and processor makes use of information related to the behavior in time of any of the parameters described herein. In one example, the behavior refers to the difference between strongly pulsatile flows present in the right atrium, in the heart in general, and/or in the arterial flow compared to the low pulsatility characteristic of venous flow. As the sensor moves, the pulsatile nature of the flow changes and the system makes a determination based on this behavioral change or pattern. The system may also take into account a periodic change in behavior of the flow profiles in comparison to the heart rate. In one example, a stronger periodic change with the heart rate or pulsatility may be indicative of the right-atrial activity.

In various embodiments, the sensor, pre-processor, and/or processor are synchronized for data acquisition and processing. The signal data can be provided as data points triggered by activation of the sensor and/or recording of a specific point in time in the data stream. The method of the invention may also use averaging, smoothing, and other techniques in connection with processing of the real-time data.

Focusing on FIG. 12a, the parameters output by the pre-processor may relate to the same point in time or different points in time within the same processing window. Referring to FIG. 12a, for example, one parameter may correspond to t1 and another parameter used in the same processing cycle may correspond to t2. In various embodiments, the system is configured to process the signal information over predetermined periods of time such as t3. The predetermined periods may be preset or may be modified by a feedback loop at the end of each analysis cycle.

The processing methods and algorithms may also identify important or unique signatures useful in guidance, localization or correlation. The method may include different or customized software or programming for processing ultrasound signal and/or other optional signal information. The processing may include processing of reflected ultrasound signal to identify the caval-atrial junction or to determine the highest average velocity of a velocity profile.

Certain of the parameters used by the system may be more reliable or more significant at different points in time. The system may make use of this fact. For example, if the antegrade flow velocity may be more significant during the strongest part of the contraction period, the system can analyze the antegrade flow velocity parameter only at this time. Other parameters may be more significant over selected periods of time than as specific periods. Yet other parameters may be more significant at peaks and valleys. Accordingly, the system may employ filters, synchronization of the sampling, recording, and processing functions, and other techniques to improve the parameter data to the processor. In various embodiments, the system weights the influence of each of the parameters. The system may employ an expert system such that the weights are changed based on expert knowledge. In various embodiments, the weights can fluctuate between zero and one such that a parameter can have no influence, complete influence, or anything in between.

In various embodiments, another sensor and signal data are provided and configured as a trigger to acquire and/or process the ultrasound information. In one aspect, the signal from one sensor is the trigger for acquisition or processing of a signal from another sensor. In this manner, the data from two different physiologic sensors may be correlated in time and to the trigger signal. Alternatively, rather than triggering acquisition data from the triggered sensor, all sensor data could be collected and/or stored and the trigger could instead result in the processing of only the subset of the data based on the trigger data. In either triggering scheme, the trigger sensor data and the triggered sensor data are processed together to yield the benefits described below. One will appreciate that the triggering method described may be used to correlate the data acquisition to the points in time when particular parameters are more or less significant.

In various embodiments, the optional intravascular electrocardiograph (ECG) signal is used for selective (gated) acquisition and processing of the blood flow information, depending upon the specific characteristics of the electrocardiogram signal being utilized. For example, when the electrocardiogram signal is produced by the heart, the gating acquisition may be based on one or more integrals of the heart cycle. In this example, detection of the P-wave detection from an electrocardiogram sensor may be triggering signal for acquiring ultrasound data from an ultrasound sensor. As described herein, the unique P-wave signal detected when an electrocardiogram lead is positioned in the superior vena cava near the sino-atrial node 8 can be used to confirm the detection of the unique blood flow pattern that also occurs in this area of the vasculature. In this way, the existence of both unique physiological signals from two different physiological systems increases the accuracy of the guidance system embodiments described herein. This selective approach may increase the accuracy of determining blood flow patterns corresponding to locations in the vasculature.

In various embodiments, a feature may be derived from a Doppler signal waveform, amplitude, position, or other aspect. In various embodiments, the selective acquisition and processing is based on muscular or physiological events such as those corresponding to:
1. Retrograde flow from atrial contraction;
2. Antegrade flow during systole, tricuspid valve closure and/or atrium fill
3. Retrograde flow at end of systole, capacitance of atrium goes to zero and negative pressure wave reverses flow in superior vena cava, and
4. Antegrade flow during diastole, filling of both atrium and ventricle In various embodiments, the selective acquisition and processing are triggered by acoustic signals from the body such as valve closing or filling of a passage.

In various embodiments, the method of positioning an endovascular device in the vasculature of a body includes processing the reflected ultrasound signal to detect indicia of pulsatile flow in the flow pattern. The indicia of pulsatile flow may be any of a number of different features. The indicia of pulsatile flow may be: a venous flow pattern; an arterial flow pattern or an atrial function of the heart. Likewise, the processing may be based on indicia of other events or features.

Input Features for Navigation and Guidance

The above description provides a better understanding of the pre-processor outputs and nature and quality of the feature information utilized by the processor. Although the exemplary system is described in terms of three specific Doppler parameters, DF1a, DF1b, DF2, and DF3, and one ECG signal, E1, one will appreciate that a variety of features may be used in accordance with the invention.

As described above, the pre-processor may be configured to extract and transmit a number of feature values to the processor. The feature information will now be described in greater detail.

In various embodiments, the pre-processor is configured to receive a signal from the non-imaging ultrasound transducer and extract a feature including, but not limited to, a venous blood flow direction, a venous blood flow velocity, a venous blood flow signature pattern, a pressure signature pattern, A-mode information, a preferential non-random direction of flow, and others.

Additional features useful in assessing location in the vasculature based on Doppler information are described below. Examples of some of the other features that can be used to determine sensor location in the vasculature from the blood flow velocity profiles include, but are not limited to: a) comparing energy (e.g. as measured by spectral power in frequency domain) of each of the directions of bidirectional flow; b) bidirectional flow patterns in lower velocity range to detect the caval-atrial junction; c) pulsatility to detect atrial activity; and d) the highest meaningful average velocity of the velocity profile and others described herein.

In another example, one feature used for correlating the Doppler frequency (velocity) distributions to the anatomical locations relates to the spectral power or the area under a specific Doppler frequency curve (the integral computed of the frequency spectrum) in conjunction with the uniformity of differences in frequencies over the entire frequency range. The sensor may be positioned in the superior vena cava looking towards the heart and with the main blood flow stream moving away from the sensor towards the heart. Based on the Doppler frequency curves (e.g. the relative areas under each curve correlated to the relative amount of flow) over the whole range of Doppler frequencies (velocities), the system can make a determination, for example, the catheter tip has been pushed into the jugular vein. Consequently, if the blood velocity profile shows larger spectral power in one direction it can be inferred that this is the predominant direction of flow of the blood stream.

Another feature is related to the distribution of the low velocities in two directions—towards and away from the sensor. In a vein, the blood velocities are different than in the right atrium. Therefore, most of the relevant spectral energy will be present in the low velocity range. Typically, low blood flow velocity range is from 2 cm/sec to 25 cm/sec.

Another feature is the similarity between the antegrade velocity curve and the retrograde velocity curve. At the caval-atrial junction (shown in FIG. 19) the curves are almost identical with similar areas (similar energy or the area under curves) and with similar velocity distributions (similar velocity profiles or shape of the curves). This is indicative of the similar inferior vena cava (IVC) and superior vena cava (SVC) flow streams joining together from opposite directions when entering the right atrium.

Another feature is the amplitude of the antegrade and retrograde velocity curves. The higher the amplitude at a certain frequency, the higher the signal energy (i.e. the more blood flows at the velocity corresponding to that particular frequency).

Another feature is the amplitude of the highest useful velocity contained in the antegrade and retrograde velocity profiles. In one example, useful velocity is defined as one being at least 3 dB above the noise floor and showing at least 3 dB of separation between directions. The highest useful velocity may be an indication of the highest average velocity of the blood stream because the exemplary device intends to measure volumetric (average) velocities.

The correlation between the shape, amplitude, and other characteristics of the intravascular waveforms and relative changes can also be used as the feature information for positioning, guiding, or confirming sensor location in accordance with the invention.

As described above, the system may also make use of non-Doppler information for different purposes, including, but not limited to, confirmation and error reporting.

Membership Functions

Turning back to FIGS. 10 and 16, the processing operation in accordance with the invention will now be described in greater detail. As shown in FIG. 16, the Doppler signal and other optional signals are input to the pre-processor 139 where they are separated. The pre-processor outputs the desired feature information and transmits the feature information to the processor 140.

Various aspects of the system are based on the recognition of patterns in the sensor signals for different physiological features and correlation of those signal patterns. The pre-processor extracted information relates to the different, desired physiological features, and the processor identifies patterns and correlations among the pre-processed information.

Various aspects of the system and method of the invention correlate the features to the phase of intravascular navigation. For purposes of illustration, one example of the system and method in accordance with the invention will be described with reference to FIG. 16.

Referring to FIG. 16, the exemplary processor sorts each of the Doppler features into membership functions 230 (also shown in Table 2 below). Given each feature value (shown in Table 1 above), the membership function value, similar to a conventional probability function, is calculated for each zone. The achieved purpose of the exemplary system is to indicate the position of the catheter tip with plus or minus about 3 cm, 2 cm, or 1 cm accuracy at the cavial atrial junction of the human heart.

Various aspects of the system and method of the invention correlate the parameters to the phase of intravascular navigation. To that end, the processor utilizes inference rules governing the use of parameter information in the various "states" of navigation. The rules and principles used with the present navigation technique will be understood from the description herein.

In order to determine the probable location of or recommended movement of the device, the exemplary guidance system utilizes the features of Doppler signals in each state. The exemplary system uses an optional ECG signal to increase the confidence level. FIG. 23 briefly describes the rules governing the use of features in each state.

The exemplary states of navigation include state 0 (weak or low usefulness of the parameter), state 1 (ECG P-wave is not elevated), state 2 (ECG P-wave is elevated), and state 3 (ECG signal is not elevated or ECG P-wave is elevated, and ECG p wave shows biphasic).

The states illustrated in FIG. 23 are based on known information about the behavior of the Doppler parameter and optional ECG parameter in various states or phases of navigation. For example, as is generally understood in the art, the flow will generally flip from predominantly antegrade to retrograde if the sensor improperly enters the atrium. Thus, the exemplary state 3 corresponds to predominating of the retrograde flow.

Additionally, the processor may take into account previous location information. For example, state 3 may only be achieved after passing through one or more of states 0, 1, and 2. State 3 would only be expected to be reached after the device is properly positioned in and navigates the venous vasculature.

The exemplary system also makes use of the ECG signal for confirmation of location. In state 3, the ECG signal is expected to be low or the P-wave is elevated, and ECG P-wave shows biphasic. Thus, the states of FIG. 23 incorporate known information about the environment of specific states of navigation and current and prior navigation.

With continued reference to FIG. 16, next exemplary processor 140 translates the parameter features (e.g. DF1 (DF1a, DF1b), DF2, DF3, and E1) from the pre-processor into membership functions 230 for further processing of the probability that the device is in or not in a particular state of navigation. Table 2 illustrates the membership functions. For a feature DF1, for example, the membership functions are PZ0D1, PZ1D1, PZ2D1, and PZ3D1. These membership functions correspond to the parameter value in each of zones 0, 1, 2, and 3, respectively.

TABLE 3

| Membership Functions | |
| --- | --- |
| Membership Function | Feature |
| PZ0D1 | DF1 |
| PZ1D1 | DF1 |
| PZ2D1 | DF1 |
| PZ3D1 | DF1 |
| PZ0D2 | DF2 |
| PZ1D2 | DF2 |
| PZ2D2 | DF2 |
| PZ3D2 | DF2 |
| PZ0D3 | DF3 |
| PZ1D3 | DF3 |
| PZ2D3 | DF3 |
| PZ3D3 | DF3 |
| PZ0E1 | EF1 |
| PZ1E1 | EF1 |
| PZ2E1 | EF1 |
| PZ3E1 | EF1 |

In general, the exemplary processor calculates a membership score for each state of navigation (shown in Table 4 below) based on a specific set of rules to calculate the state with the highest probability (which corresponds to the result). The exemplary system makes use of the rules described in FIG. 23 above.

Table 3 lists the weighting matrix for each of the Doppler parameters in each of the states of function. Thus, as shown in Table 3 and FIG. 16, for example, DF2 will be weighted by a factor of Wy3 in state 0. In state 1, the weighting will change to Wg3.

The rules governing the use of the parameter information in the various "states" of navigation described herein inform the weighting of the calculation and balancing of the contribution of the various parameters. The weighting is determined based on the contribution of each parameter/feature to each class.

Additionally, Table 3 indicates that the each feature has a weight for each state (zone). In fact, the weights can be zero for some zones or states based on the current condition or strength of the Doppler and ECG signals. For example, State 1 uses all four Doppler features and pRatio (ECG1). By contrast, State 0 (yellow) only looks at DF2 and pRatio. In some embodiments, not every feature is used to determine the score. In still other embodiments, the relative strength of a signal may be used to adjust a weight. For example, a weak signal can be weighted less than a strong signal or have its weight decreased, while a strong signal can be weighed more than a weak signal or have its weight increased. This is one example of adaptive weighting which allows the algorithm to adjust to the patient and/or changing conditions during use.

TABLE 4

Weights

| | | Feature | | |
|---|---|---|---|---|
| State | Doppler 1 (DF1) | Doppler 2 (DF2) | Doppler 3 (DF3) | ECG 1 |
| 0 | Wy1 | Wy2 | Wy3 | Wye1 |
| 1 | Wg1 | Wg2 | Wg3 | Wge1 |
| 2 | Wb1 | Wb1 | Wb3 | Wbe1 |
| 3 | Wr1 | Wr2 | Wr3 | Wre1 |

Table 4 illustrates an indicator score matrix for each of factors 1, 2, 3, and 4. In general, the factor score represents the weighted likelihood of the device being in any of states 0, 1, 2, and 3.

In general, the factor score is equal to the sum of the respective weights shown in Table 3 multiplied by the respective membership function shown in Table 2 for each of states 0, 1, 2, and 3. As the device is expected to be in one of the states, the sum of all the weights in each class is equal to 1. The summation function is shown as element 141 in FIG. 16.

TABLE 5

Indicator Score

| Score | Factor 1 | Factor 2 | Factor 3 | Factor 4 |
|---|---|---|---|---|
| S0 | Wy1*PZ0D1 | Wy2*PZ0D2 | Wy3*PZ0D3 | Wye1*PZ0E1 |
| S1 | Wg1*PZ1D1 | Wg2*PZ1D2 | Wg3*PZ1D3 | Wge1*PZ1E1 |
| S2 | Wb1*PZ2D1 | Wb1*PZ2D2 | Wb3*PZ2D3 | Wbe1*PZ2E1 |
| S3 | Wr1*PZ3D1 | Wr2*PZ3D2 | Wr3*PZ3D3 | Wre1*PZ3E1 |

Table 5 illustrates the calculation of a probability or membership score for each of the parameters in the different states. Referring to FIG. 16, the processor calculates a score 142 as described. The final score of each "class" is a weighted sum of the output scores from all the parameter membership functions (i.e. membership functions for DF1, DF2, DF3, and E1).

The weighted sum of the output scores from all the feature membership functions for one class is as follows:

$$S_R = \sum_n w_R(n) \cdot S_R(n)$$

The above equation represents one of the output scores for red (state 3 in FIG. 23). "n" refers to the number of parameter features. Generally, the scores for each of the classes corresponding to the different states increase and decrease in likelihood with the membership function.

TABLE 6

Score Calculation

S = Factor 1 + Factor 2 + Factor 3 + Factor 4

As shown in FIG. 16, final scores 142 are output by the processor 140. The processor then determines the state of navigation based on the highest score. In other words, the highest score corresponds to the highest likelihood, and the device is determined to be in the most likely location determined by the processor. In the above example, if SR is the highest score, the processor outputs a result related to State 3. In another example, if the highest score corresponds to state 0, the processor provides an output to the output device to display a yellow arrow.

The exemplary system includes exceptions to the above processing output. The exceptions may be based on expert knowledge, thresholds, or the like. In various embodiments, the system includes two exceptions to the results from above, which can be handled using a fuzzy logic based algorithm. The two exemplary exceptions include:

IF there are a number of consecutive heart beats in State 0 (Yellow), and the State 2 score (Blue Bull's Eye) is greater than State1 and State 3 scores, then output "State 2".

IF detect atrial fibrillation, or other ECG abnormalities (e.g. if ECG P Waves becomes bi-phasic), then default to State 3.

IF detect dominant retrograde flow, then default to State 3.

The selection of parameters and weighting play a significant role in the accurate positioning and guidance of the system of the invention. An exemplary device configured similar to the above has been found to have a high, clinically-acceptable level of accuracy with respect to positioning and location confirmation. The catheter tip was located at the cavial atrial junction with repeated accuracy without the need for X-ray guidance.

Moreover, acquisition, conversion, processing and correlation steps, components, and capabilities may be included in the system 100 as needed depending upon the type and number of sensors employed on the endovascular device 150.

Intravascular Placement and Positioning

Figure 17:
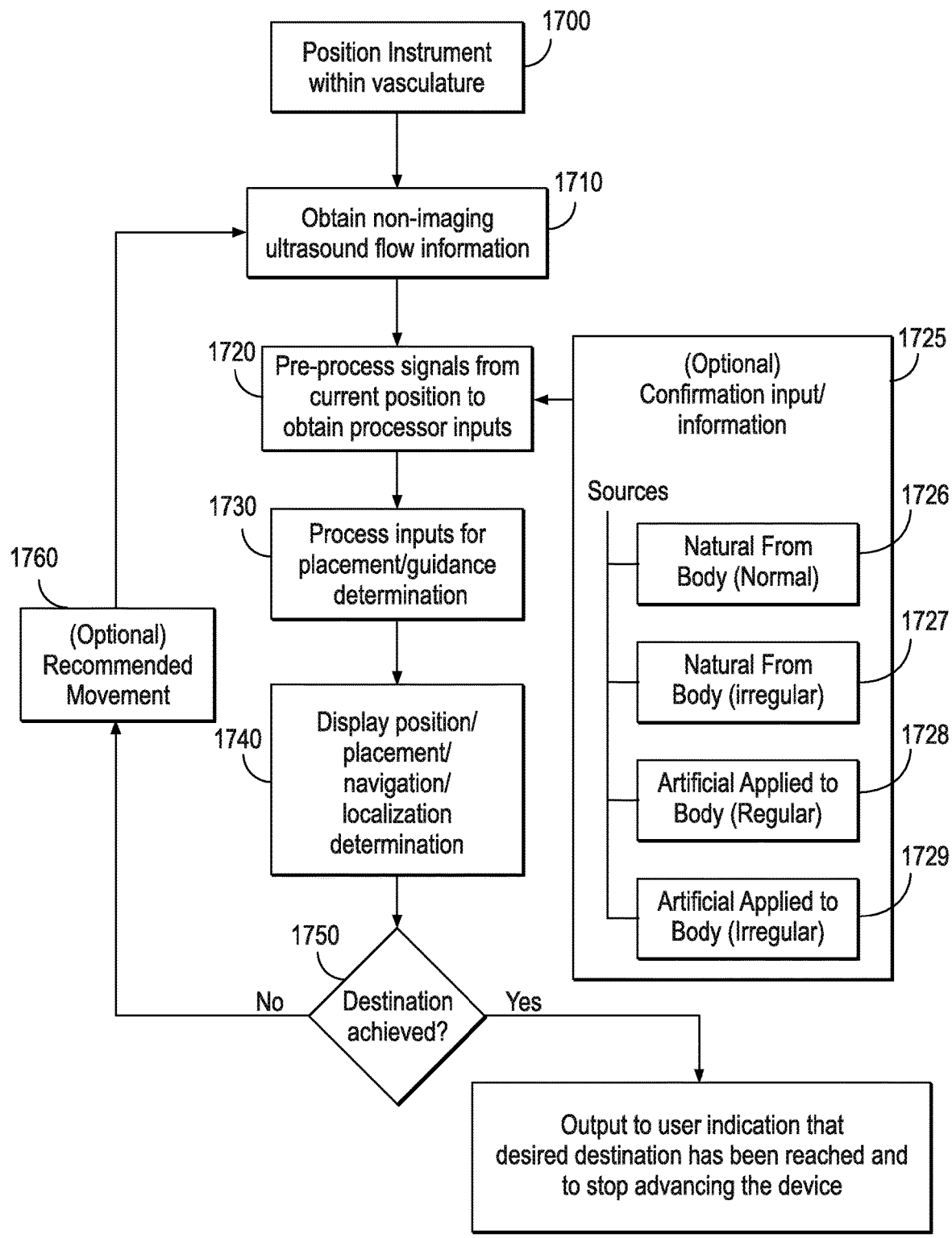
FIG. 17 is a flow chart of the method of using the system of FIG. 9 to guide an endovascular device to a desired destination in accordance with the invention.
Figure 18:
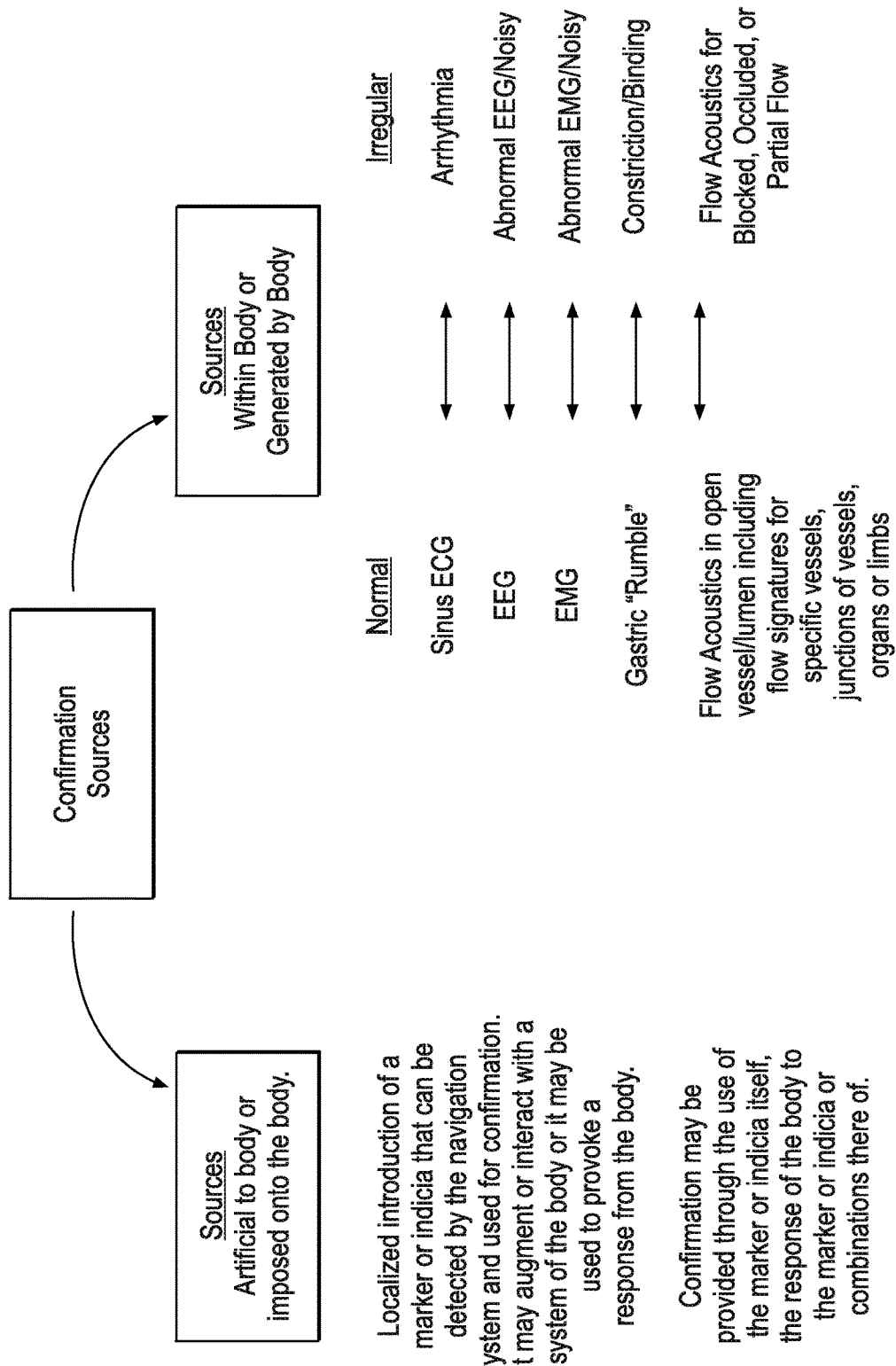
FIG. 18 is a block diagram of optional confirmation sources that may be input to the pre-processor according to the method of FIG. 17.
Figure 19:
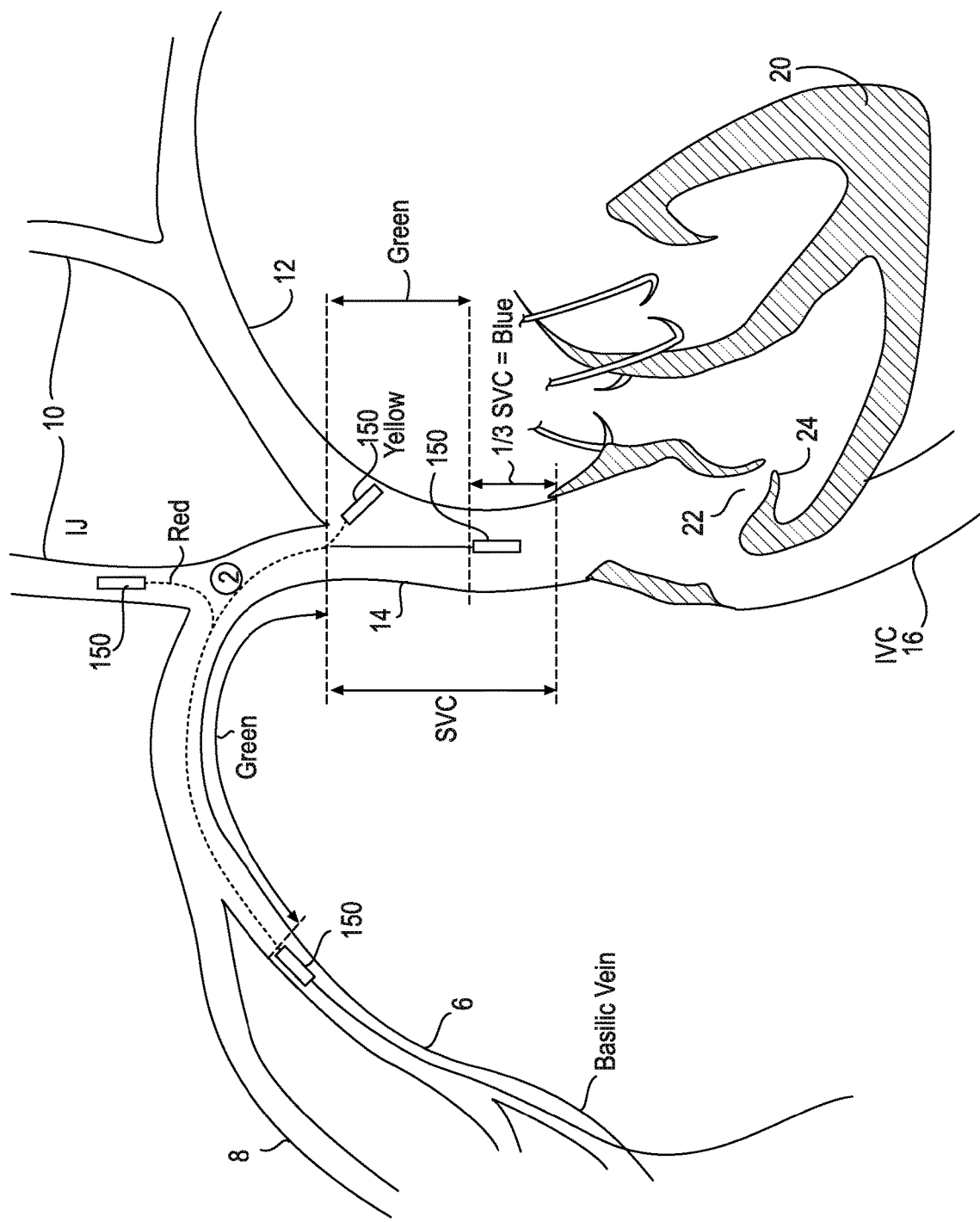
FIG. 19 illustrates an endovascular device within the vasculature at various locations according to the method of FIG. 17.

Turning to FIGS. 17-19, the method of using a system in accordance with the invention will now be described. The exemplary system is configured similarly to FIG. 1. As discussed above, the methods for intravascular guidance and placement of endovascular devices disclosed herein are generally based on the recognition of patterns in the signals for different physiological parameters and correlation of those signal patterns.

Various aspects of invention relate to a method to substantially increase the accuracy and reduce the need for imaging related to placing an intravascular catheter or other devices. The method generally relates to the guidance, positioning, and placement confirmation of intravascular devices such as catheters, stylets, guidewires and other elongate bodies that are typically inserted percutaneously into the venous or arterial vasculature, including flexible elongate bodies.

According to one embodiment of the present invention, there is provided a method for positioning an instrument in the vasculature of a body using the instrument to determine a location to secure a device within the vasculature of a body; and securing the device to the body to maintain the device in the location determined by the instrument. After the passage of some period of time (as is common with patients who wear catheters for an extended period of time), the instrument may be used to calculate the current position of the device. Next, using the known original position and the now determined current position, the system can determine if the device has moved from the original position.

FIG. 17 illustrates an exemplary method 300 of catheter placement. This example is for illustration purposes only. Similar conventional catheter, guide wire, or device introduction procedures may be tailored for the requirements of other therapeutic devices such as, for example, placement of hemodialysis catheters as well and placement of laser, RF, and other catheters for percutaneous treatment of varicose veins.

From top to bottom, FIG. 17 represents a single analysis or processing cycle. The cycle is repeated for each newly-acquired sample signal data. In general, the exemplary cycle is performed over and over until a desired destination is achieved.

In this example, the method 300 describes how a user would place a PICC catheter using a guided vascular device with guidance information displayed on an output device similar to that described above. The exemplary catheter is similar in many respects to the device 150 described above and includes one or more sensors. The output device 130 indicates a navigation direction or position of the device based on the collection, processing, and use of information related to the signal data collected by the exemplary device.

In general, the exemplary system operates by collecting and manipulating a reflected ultrasound signal to determine a position of the device. In an exemplary embodiment, the desired destination of the device is where two or more vessels join. However, one will appreciate that this method may be practiced in any of a wide variety of vascular junctions and other locations in both the venous and arterial vasculature. Other exemplary positions where two or more vessels join include the junction between a superior vena cava and an inferior vena cava and a junction between an inferior vena cava and a renal vein.

While the techniques described herein may be practiced in a number of clinical settings, the placement method 300 will be described in relation to bedside catheter placement. The workflow presented in catheter placement method 300 begins with preparing the device for placement. A user prepares the device in a conventional manner and as described in greater detail above.

The medical professional next inserts the catheter into the vessel at step 1700. This step is similar to the catheter introduction currently performed by medical professionals. One exemplary insertion point is the basilic vein 6 as shown in FIG. 19.

At step 1700, the user holds the devices in position in the vessel until the output device provides an indication of positive placement. As described above, the indication may be a change from a blinking green light to a solid green light. In the exemplary case of navigating the venous vasculature, the output indicator provides a clear indication to the user that the device is positioned in a vein.

Once in position in the vessel, the user holds the device in position or slowly moves the device forward for a few seconds. This step ensures that the signal processing algorithm can calibrate the data acquisition and pattern recognition to the current patient data. Additionally, the processing system will analyze the sensor date to confirm that the sensor is placed in a vein not an artery. If the guidance system includes other optional signal acquisition and evaluation, such as use of an ECG signal as described below, this may also be an appropriate time to establish and record a baseline. In some embodiments, the processing system can record the external ECG during the baseline. The P wave magnitude can be extracted and the external P wave magnitude can be used in the pRatio to determine if the catheter tip is at the CAJ at every time step. The processing system can also record information about the patient (age, gender, heart conditions, etc) to further tune and customize the algorithm more to the patient.

After receiving confirmation from the system that the sensor/catheter has been introduced into a vein, the clinician may start advancing the catheter. The clinician navigates and positions the device as described above, for example, in relation to FIG. 19. The underlying operation of the guidance system is described in greater detail above.

Turning to step 1710, the device is enabled to transmit and receive signals to collect information for use in the navigation and placement process of the invention. In various embodiments, the device transmits a non-imaging ultrasound signal into the vasculature using a non-imaging ultrasound transducer on the endovascular device. The device receives a reflected ultrasound signal with the non-imaging ultrasound transducer. One will appreciate that other signals may also be provided with the addition of sensors and other mechanisms in accordance with the invention.

At Step 1720, the system pre-processes the reflected ultrasound signal received by the non-imaging ultrasound transducer and the optional additional sensors. The pre-processing technique is described in greater detail above with respect to FIGS. 9 to 16. In general, the pre-processing involves data acquisition from the sensors and extracting of designated information parameters. In some respects, the extracted information represents the real-time sensor environment.

The method of using the exemplary device may optionally include a confirmation subroutine to verify the location of the device. Although the method described above involves reliable placement of the device in the vasculature, for various reasons a user may wish to use additional techniques to further increase the reliability and accuracy of the method.

Accordingly, at optional Step 1725, the system includes additional non-Doppler sensors for providing a confirmation signal as an input to the pre-processor. The confirmation signal may be derived from a natural source or an artificial source. Because the system does not use these other sources as the primary location information, the natural and artificial sources may be normal (regular) or irregular. Examples of natural and artificial sources, both regular and irregular, are shown in FIG. 18, and include a regular, natural source from the body 1726, a irregular natural source from the body 1727, a regular artificial source applied to the body 1728, and an irregular artificial source applied to the body 1729.

A natural source is a source that naturally occurs within the body or is naturally generated by the body. A normal or regular natural source includes sinus ECG, RS amplitude, EEG, EMG, a gastric rumble, and flow acoustics in an open vessel or lumen including flow signatures for specific vessel, junctions of vessels, organs or limbs. An irregular natural source includes arrhythmia, abnormal EEG that can be noisy, abnormal EMG that can be noisy, and flow acoustics for blocked, occluded or partial flow through a vessel.

An artificial source is a source that artificial and not naturally occurring in the body or is something imposed onto the body. An artificial source can be introduced to the body by localized introduction of a marker or indicia that can be detected by the navigation system and used for confirmation. The artificial source may augment or interact with a system of the body or it may be used to provoke a response from the body. Confirmation can be provided through the use of the marker or indicia itself, the response of the body to the marker or indicia or combinations thereof.

One will appreciate from the description herein how to incorporate a number of conventional placement verification techniques in conjunction with the present method. In one example, a medical professional will approximate a necessary length of catheter prior to the procedure. In use, the professional can verify that the amount of length that has been inserted reasonably corresponds to what is expected for the position indicated by the output device. In this manner, conventional, non-electronic positioning techniques can be used to verify proper working of the guidance system.

The method may also make use of other confirmatory techniques as would be appreciated by one of skill in the art from the description herein. For example, the method may make use of confirmatory signals described above and illustrated in FIG. 18.

In step 1730, the pre-processed signal information is provided as inputs to a processor that implements artificial intelligence. As will be understood from the description herein, the pre-processing of the signal information plays an important role in the function of the processor and the ultimate results of the system provided to the user.

In general, the pre-processor processes the signal data and outputs parameter information. The processor than uses the pre-processor outputs to make a determination and provide a result. For example, the pre-processor may receive streams of raw Doppler data and output corresponding total power values, ratios of antegrade/retrograde flow, and ratios of low velocity power to high velocity power. The processor then uses the outputs to make a determination with respect to the sensor(s), for example, that the sensor is moving in a direction with the blood flow or that the sensor is located in a particular position. Accordingly, the pre-processing and processing are interrelated to provide accurate results to the clinician. The operation of the processor of the invention in conjunction with the pre-processor will be described in more detail above with respect to FIGS. 9 to 16.

In various embodiments, the processor makes use of the parameter information by recognizing flow patterns and/or signatures in the flow. In various embodiments, the processor compares a respective processor input to another input or to a calculated value. In various embodiments, the processor compares a respective processor input to values in a look-up table. The use of a look-up table provides the advantage of reducing the number and complexity of processing operations that must be performed.

At step 1740, the processor provides an output to the output device based on the processor determination. The output displays an indication to the user regarding movement or positioning of the sensor.

Next, at step 1750, the user reads the output device and stops advancing the catheter if the output device indicates that the catheter is in the desired destination. Otherwise, the user continues advancing the catheter and the process continues.

In an exemplary embodiment, the guidance system is configured to guide a catheter to the superior vena cava (SVC). In the region near the entry to the SVC, the output device displays a red light if the catheter/sensor is determined to be in the jugular or other vein instead of the SVC. In FIG. 19, this position is labeled "Red" and the catheter is shown in the internal jugular vein. In this situation the blood stream flowing towards the heart comes towards the device.

The system may also be configured to determine the proximity of the catheter/sensor to a structure. For example, if the catheter is facing a vessel wall and cannot be advanced, the output device displays a yellow light (marked "yellow" in FIG. 19). Further, the exemplary output device displays a blue light to indicate that the desired destination has been reached.

The method includes an optional Step 1760. The exemplary system is configured to determine a recommended direction of movement to reach the desired destination and indicate the direction via the output device. In various embodiments, the system uses the historical position information, present information, and/or other information to determine a recommended direction. In turn, the output device may include a symbol, color, graphic or other indicator to convey the recommendation to the user in Step 1760.

It should be understood that various alternatives to the embodiments of the invention described herein may be employed in practicing the invention. For example if the target device position where in the brain for example, then the processing algorithms and outputs could be changed to indicate that movement into the jugular is the correct direction (green indicator) and that movement towards the heart would be an incorrect direction (red indicator). The system indications and parameters can be altered depending upon the location of and access route taken to various different target sites in the vasculature.

The method of positioning an endovascular device in the vasculature of a body may also include additional or modified steps according to the specific application or process being performed. Numerous additional alternative steps are possible and may be used in a number of combinations to achieve the guidance and positioning results described herein. Additional steps may include verifying that the length of the endovascular device inserted into the body is equivalent to the estimated device length prior to the procedure and/or inputting into the system the length of the endovascular device inserted in the body.

Figure 22:
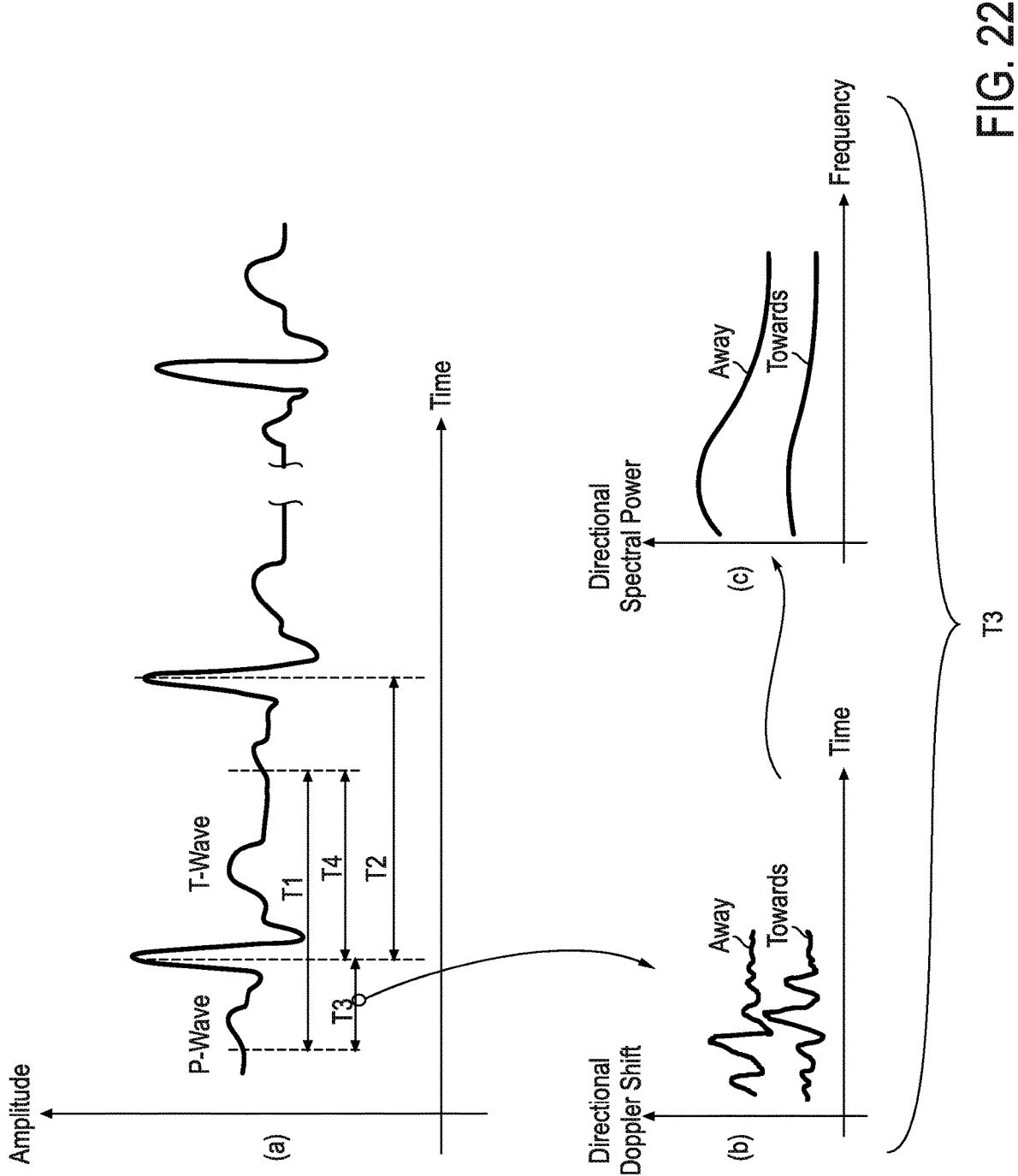
FIG. 22 illustrates the optional use of an intravascular ECG signal to gate or trigger the acquisition or processing of the blood flow information.

The method of positioning may also make use of various non-Doppler signals for selective acquisition and processing. FIG. 22 illustrates how the endovascular electrical signal can be use to trigger and gate the processing of the ultrasound signals. The electrical signal acquired from the endovascular sensor is periodic and related to the heart cycle (10*a*). It is similar in shape with a known diagnostic ECG signal. By analyzing the waveforms, e.g., P-wave, QRS complex and the T-wave, a number of events and time segments can be defined in the heart cycle. The P-wave event occurs when the P-wave amplitude is at its peak. The-R-wave event occurs when the R-wave amplitude is at its peak. Other events can be defined, e.g., when the R-wave amplitude is one third lower than the peak. Between such events time intervals can be defined. T1 is the time interval between 2 consecutive P-waves and indicates the heart rate. T2 is the time interval between two R-waves and similarly indicates the heart rate. T3 is the time interval between the P and the R waves. T4 is the time interval between the R-wave and the subsequent P-wave. Other time intervals can be defined, as well. These intervals can be defined in reference to a peak value of a wave, the beginning or end of such a wave, or any other relevant change in the electric signal. The events defined in a heart cycle can be used to trigger selective acquisition and/or processing of physiological parameters through the different sensors, e.g., blood flow velocity information through the Doppler sensor. The time intervals can be used to gate the acquisition and processing of physiological parameters like blood velocity, e.g., only in the systole or only in the diastole. Thus more accurate results can be provided for guiding using physiological parameters. Graphs 10b and 10c illustrate exemplary ultrasound data triggered on the T3 interval.

One will appreciate that other triggers may be used. For example, variations in blood flow as identified by the Doppler signal can be used to trigger and gate signal acquisition and processing based on the respiratory activity of the patient. The flow patterns as indicated by the Doppler power spectrum change with the patient's respirations. Certain cardiac conditions like regurgitation also cause changes in the flow patterns with respiration. Such changes with respirations can be identified, in particular when the strength of a certain pattern changes with respirations. These identified changes can then be used to trigger and gate the acquisition and processing of physiological parameters relative to the respiratory activity of the patient. Thus more accurate results can be provided for guiding using physiological parameters.

Other features of the ECG waveform may also be used to trigger signal acquisition. For example, the relative changes in the QRS complex can be used to identify proximity of the sinoatrial node even in patients with atrial fibrillation, i.e., patients without a significant P-wave detected by diagnostic ECG. In patients with atrial fibrillation, the P-wave cannot be typically seen with current diagnostic ECG systems. However, changes (i.e., significant increases in the QRS complex amplitude as identified by an endovascular sensor) may be indicative of the proximity of the sino-atrial node. In addition, an endovascular device can measure electrical activity which is not detected by a standard ECG system (e.g. the atrial electrical activity in a patient thought to have atrial fibrillation). Such changes in the waveform of the endovascular electrical signal can be used to position the sensor and the associated endovascular device at desired distances with respect to the sino-atrial node including in the lower third of the superior vena cava or in the right atrium.

The methods, devices, and systems of the invention provide many advantages over conventional guidance and positioning systems and techniques. One benefit of the new apparatus and method introduced herein is that it increases the probability of correct placement of an endovascular device in a placement procedure performed at the bedside. Moreover, because of the accuracy and redundancy of the positioning methods described herein, it is believed that the use of the inventive methods, devices, and systems will allow for endovascular device placement without the need for imaging guidance, in particular without X-ray imaging and/or imaging for confirmation of placement and lack of device migration. Another benefit of the new apparatus and method may be it provides for correct placement of an endovascular device in a placement procedure on a larger group of patient's such as those experiencing an aneurysm. Yet another benefit of the new apparatus and method introduced herein may be that it allows the detection of blood clots in the vasculature or in catheters such as identifying the cause for a mal-functioning catheter, e.g., a central line.

Yet another benefit is related to the fact that the guided vascular access devices and the systems described herein may be inserted into the existing healthcare workflow for placing endovascular devices into the vasculature. More specifically, embodiments of the invention provide new sensor-based endovascular devices, systems, and methods for intravascular guidance and placement of, for example, sensor-based catheters and/or guide wires. The properly-positioned, sensor-based endovascular device is then used to guide the deployment of other endovascular devices or facilitate the performance of other diagnostic or therapeutic procedures in the body such as, for example: (a) location of heart valves for replacement heart valve procedures; (b) identification of the renal veins for therapy in those veins or in the kidneys; (c) identification of renal veins and/or the inferior vena cava for IVC filter placement; (d) location of coronary sinus for placement of pacing leads or mitral valve modification devices; and (e) location of pulmonary veins for sensor placement and/or performance of therapy such as ablation treatment for atrial fibrillation. A wide variety of other diagnostic or therapeutic procedures may also benefit from the placement of device or performance of therapy at specific locations in the vasculature identified by the sensor correlation techniques described herein.

In some embodiments, the systems and methods of embodiments of the inventive guidance system described herein are utilized to locate, guide and position catheters and/or guide wires equipped with sensors described herein within the vessels of the venous system. The embodiments described herein may also be utilized in the vessels of the arterial system as well. In one aspect, the guided vascular access devices described herein may be used for the guidance, positioning, and placement confirmation of intravascular catheters used in a wide number of clinical applications. Exemplary clinical applications that would benefit from embodiments of the invention include the placement of, for example, central venous access catheters (PICC), hemodialysis catheters and the placement of catheters, positioning of endovascular devices in the vasculature of the brain for treatment of stroke, placement of leads or other brain based therapy or therapy devices or treatment systems for percutaneous treatment of varicose veins. Moreover, particular muscles or muscle groups may be selected for EMG stimulation and/or senor collection in support of one of more methods and devices described herein where the EMG signals are used to confirm and/or correlate a position in the vasculature. This aspect may be particularly helpful when identifying portions of the vasculature in the legs for localization of varicose veins, localization of the femoral veins or positioning of a vessel harvesting device within the great saphenous vein, for example.

Other System Features

In various embodiments, all or some of the operations of the above method are automated. In various embodiments, the system is remotely controlled, networked, or transfers information through a wireless interface. Such information can be coordinated with a central location via, for example, a wireless network.

In many clinical applications, endovascular devices are required to have the device tip (distal end) to be placed at a specified location in the vasculature. For example, CVC and PICC lines are required to have their tip placed in the lower third of the superior vena cava. However, for example, due to lack of a guidance system at the patient's bedside, users currently place the catheters into the patient's body blindly, often relying on x-ray to confirm the location of the catheter a couple of hours after initial placement. Since the CVC or a PICC line can be released for use only after tip location confirmation, the patient treatment is delayed until after X-ray confirmation has been obtained. Ideally, users should be able to place the catheter at the desired location with high certainty and with immediate confirmation of tip location. Building a user-friendly, easy-to-use system which integrates electrical activity information with other types of guiding information, devices and techniques described herein.

While the simplified user interface provides a clear indication to a clinician the position and direction of the distal end of the device, it may be desirable to store the guidance information during the procedure. The position information, and in particular the processor results, can be digitally recorded so that it can be used to print a report for the patient's chart. Storing of patient information, exporting the data to a standard medium like a memory stick, and printing this information to a regular printer may be especially useful when the device and system disclosed in the current invention are used without chest X-ray confirmation to document placement at the cavo-atrial junction of the endovascular device.

In some embodiments, with respect to the descriptions and figures provided herein, such as FIGS. 9-18 which disclose manipulating acoustic and electrical signals during preprocessing and processing steps, a computer readable storage medium having embodied thereon a program can be used with the devices, systems and methods disclosed herein. The program can be executed by a processor to perform a method for positioning an endovascular instrument in a vasculature, the method comprising manipulating a reflected acoustic signal from a sensor on the instrument positioned within a blood vessel to extract one or more acoustic features from the acoustic signal; manipulating an electrical signal from a lead on the instrument positioned within a blood vessel to extract one or more electrical features from the electrical signal; generating an output related to guidance or a position of the instrument within the blood vessel using a computer readable set of rules to evaluate the one or more extracted features; and displaying one of a predetermined number of indications of guidance or position corresponding to the output.

In some embodiments, the computer readable set of rules on the computer readable medium comprises one or more predefined membership functions that indicate one or more positional states of the instrument. The computer readable storage medium further comprises instructions for inputting the extracted features into the one or more predefined membership functions and for generating one or more scores that indicate the likelihood of membership in one or more positional states. The computer readable storage medium can further comprise instructions for weighting the extracted features or one or more membership functions before generating one or more scores, wherein weighting the extracted features or one or more membership functions comprises applying weighting factors to the extracted features or one or more membership functions, wherein the weighting factors apply less weight to an extracted feature or one more membership function based on a weak acoustic or electrical signal, wherein the weighting factors apply more weight to an extracted feature or one more membership function based on a strong acoustic or electrical signal.

In some embodiments, extracted acoustic features used by the program relate to, for example, the direction of movement of the instrument relative to flow in the vasculature, the overall flow energy in the vasculature measured by the sensor, the overall flow velocity in the vasculature measured by the sensor, a ratio of a low frequency flow power to a high frequency flow power, an acoustic signal obtained during a portion of a heartbeat, the portion of a heart beat during the occurrence of retrograde flow produced by atrial contraction, the portion of a heart beat during the occurrence of retrograde flow at the end of systole, and/or the portion of a heart beat during the occurrence of antegrade flow during diastole.

In some embodiments, extracted electrical features used by the program relate to, for example, a portion of an QRS complex, a ratio of a magnitude of a P-wave measured by the sensing electrode and a magnitude of a P-wave measured by an external electrode, and/or an indication of the presence of a biphasic P-wave.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method of determining a position of a medical device in vasculature of a patient, the method comprising:
   receiving an electrical signal from an electrode on the medical device;
   extracting one or more ECG features from the electrical signal;
   calculating a first indicator score by inputting the one or more ECG features into a first indicator equation;
   calculating a second indicator score by inputting the one or more ECG features into a second indicator equation;
   identifying a positional state of the medical device by comparing the first and second indicator scores; and
   displaying an indicator on an output device indicating the positional state.

2. The method of claim 1, wherein the one or more ECG features includes a plurality of ECG features.

3. The method of claim 1, wherein the one or more ECG features corresponds to one or more of:
   a portion of a QRS complex;
   a ratio of a magnitude of a P-wave measured by the electrode on the medical device and a magnitude of a P-wave measured by an external electrode; and/or
   an indication of a presence of a biphasic P-wave.

4. The method of claim 1, further comprising:
   receiving a reflected ultrasound signal;
   extracting an ultrasound feature from the reflected ultrasound signal;
   inputting the ultrasound feature into the first indicator equation; and
   inputting the ultrasound feature into the second indicator equation.

5. The method of claim 1, wherein the one or more ECG features infer a distinct position in the vasculature.

6. The method of claim 1, wherein the first and second indicator equations represent positioning probabilities.

7. The method of claim 1, wherein the first and second indicator equations correspond to membership functions.

8. The method of claim 1, wherein calculating the first indicator score includes applying a weighting factor to the one or more ECG features.

9. The method of claim 1, wherein identifying the positional state further comprises selecting the positional state that corresponds to a higher or highest indicator score.

10. The method of claim 1, wherein calculating the first indicator score and the second indicator score further comprises solving the first and second indicator equations based on a correlation between the one or more ECG features and a probability of a particular position or state of navigation of the medical device.

11. A non-transitory computer readable storage medium including a program configured to be executed by a processor to perform a method of determining a position of a medical device in vasculature of a patient, the method comprising:
    receiving an electrical signal from an electrode on the medical device;
    extracting one or more ECG features from the electrical signal;
    calculating a first indicator score by inputting the one or more ECG features into a first indicator equation;
    calculating a second indicator score by inputting the one or more ECG features into a second indicator equation;
    identifying a positional state of the medical device by comparing the first and second indicator scores; and
    displaying an indicator on an output device indicating the positional state.

12. The non-transitory computer readable storage medium of claim 11, wherein the one or more ECG features includes a plurality of ECG features.

13. The non-transitory computer readable storage medium of claim 11, wherein the one or more ECG features corresponds to one or more of:
    a portion of a QRS complex;
    a ratio of a magnitude of a P-wave measured by the electrode on the medical device and a magnitude of a P-wave measured by an external electrode; and/or
    an indication of a presence of a biphasic P-wave.

14. The non-transitory computer readable storage medium of claim 11, wherein the method further comprises:
    receiving a reflected ultrasound signal;
    extracting an ultrasound feature from the reflected ultrasound signal;
    inputting the ultrasound feature into the first indicator equation; and
    inputting the ultrasound feature into the second indicator equation.

15. The non-transitory computer readable storage medium of claim 11, wherein the one or more ECG features infer a distinct position in the vasculature.

16. The non-transitory computer readable storage medium of claim 11, wherein the first and second indicator equations represent positioning probabilities and/or correspond to membership functions.

17. The non-transitory computer readable storage medium of claim 11, wherein calculating the first indicator score includes applying a weighting factor to the one or more ECG features.

18. The non-transitory computer readable storage medium of claim 11, wherein identifying the positional state further comprises selecting the positional state that corresponds to the highest indicator score.

19. The non-transitory computer readable storage medium of claim 11, wherein calculating the first indicator score and the second indicator score further comprises solving the first and second indicator equations based on a correlation between the one or more ECG features and a probability of a particular position or state of navigation of the medical device.

20. A system configured to determine a position of a medical device in vasculature of a patient, the system comprising:
    a pre-processor configured to:
        receive an electrical signal from an electrode on the medical device, and
        extract one or more ECG features from the electrical signal
    a processor configured to:
        receive the one or more extracted ECG features from the pre-processor,
        calculate a first indicator score by inputting the one or more ECG features into a first indicator equation,
        calculate a second indicator score by inputting the one or more ECG features into a second indicator equation, and
        identify a positional state of the medical device by comparing the first and second indicator scores; and
    an output device configured to display an indicator indicating the positional state.

* * * * *